United States Patent
Shepherd

(10) Patent No.: US 7,399,867 B2
(45) Date of Patent: Jul. 15, 2008

(54) SELECTIVE ESTROGEN RECEPTOR MODULATORS CONTAINING A PHENYLSULFONYL GROUP

(75) Inventor: Timothy Alan Shepherd, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 667 days.

(21) Appl. No.: 10/521,896

(22) PCT Filed: Jul. 16, 2003

(86) PCT No.: PCT/IB03/03349

§ 371 (c)(1),
(2), (4) Date: Jan. 18, 2005

(87) PCT Pub. No.: WO2004/009086

PCT Pub. Date: Jan. 29, 2004

(65) Prior Publication Data

US 2006/0183736 A1    Aug. 17, 2006

Related U.S. Application Data

(60) Provisional application No. 60/450,233, filed on Feb. 25, 2003, provisional application No. 60/397,869, filed on Jul. 22, 2002.

(51) Int. Cl.
C07D 211/06    (2006.01)
(52) U.S. Cl. ..................... 546/206
(58) Field of Classification Search .......... 546/206
See application file for complete search history.

(56) References Cited

U.S. PATENT DOCUMENTS 4,418,068 A    11/1983    Jones

FOREIGN PATENT DOCUMENTS

| EP | 639567 | 2/1995 |
|----|--------|--------|
| EP | 729951 | 6/1999 |
| EP | 1113013 | 7/2001 |
| EP | 791591 | 8/2001 |
| EP | 791591 B1 | 8/2001 |
| EP | 835868 | 8/2001 |
| EP | 802183 | 10/2001 |
| EP | 826680 | 10/2001 |
| EP | 826679 | 11/2001 |
| EP | 703228 | 3/2002 |
| EP | 703231 | 5/2002 |
| EP | 826670 | 5/2002 |
| EP | 747054 | 8/2002 |
| EP | 838464 | 9/2003 |
| EP | 826683 | 10/2004 |
| WO | WO 95/10513 | 4/1995 |
| WO | WO 96/21656 | 7/1996 |

OTHER PUBLICATIONS

Clinical Summary, Individual Study Information for LY2066948, IND No. 70,513, Protocol No. H8Q-LC_GQAC, Clinical Phase: I, Protocol Title: Multiple-Dose Safety Study in Premenopausal Women, Annual Report, 2007.

Grese, Timothy A. *Structure-Activity Relationships of Selective Estrogen Receptor Modulators: Modifications to the 2-Arylbenzothiophene Core of Raloxifene*, J. Med. Chem., 1997, vol. 40, pp. 146-167.

*Primary Examiner*—Taofiq Solola
(74) *Attorney, Agent, or Firm*—Gilbert T. Voy

(57) ABSTRACT

The present invention relates to a selective estrogen receptor modulator of formula I or a pharmaceutical acid addition salt thereof; useful, e.g., for treating endometriosis and/or uterine leiomyoma/leiomyomata.

(I)

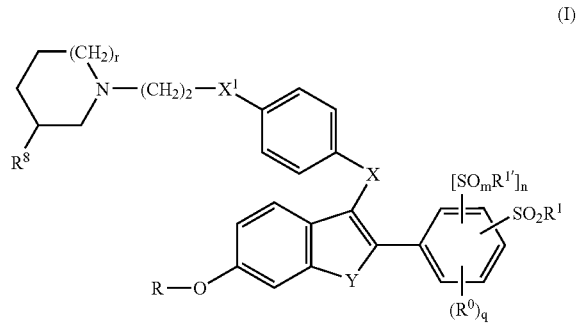

2 Claims, No Drawings

SELECTIVE ESTROGEN RECEPTOR MODULATORS CONTAINING A PHENYLSULFONYL GROUP

This application claims the benefit under 35 U.S.C. §120 of International Application No. PCT/IB2003/003349 filed Jul. 16, 2003, which claims the benefit under 35 U.S.C. § 119(e) of U.S. Ser. No. 60/450,233, filed Feb. 25, 2003 and U.S. Ser. No. 60/397,869, filed July 22, 2002.

BACKGROUND OF THE INVENTION

Uterine leiomyoma/leiomyomata (uterine fibroid disease) is a clinical problem that goes under a variety of names, including uterine fibrosis, uterine hypertrophy, uterine leiomyomata, myometrial hypertrophy, fibrosis uteri, and fibrotic metritis. Essentially, uterine fibrosis is a condition where there is an inappropriate deposition of fibroid tissue on the wall of the uterus. This condition is a cause of dysmenorrhea and infertility in women.

Endometriosis is a condition of severe dysmenorrhea, which is accompanied by severe pain, bleeding into the endometrial-masses or peritoneal cavity and often leads to infertility. The symptoms' cause appears to be ectopic endometrial growths that respond inappropriately to normal hormonal control and are located in inappropriate tissues. Because of the inappropriate locations for endometrial growth, the tissue-seems to initiate local inflammatory-like responses causing macrophage infiltration and a cascade of events leading to initiation of the painful response. Evidence suggests that a cause of uterine fibrosis and endometriosis is an inappropriate response of fibroid tissue and/or endometrial tissue to estrogen.

Many publications have appeared within the last ten years disclosing selective estrogen receptor modulators (SERMs), e.g., U.S. Pat. Nos. 5,484,795, 5,484,798, 5,510,358, 5,998,401 and WO 96/09040. Many of these SERMs, generally speaking, have been found to have a beneficial estrogen agonist activity in the bone and cardiovascular systems with a concomitant beneficial estrogen antagonist activity in the breast. A small, particularly useful subset of such compounds has also been found to have an estrogen antagonist effect in the uterus. A compound with this SERM profile holds particular promise in treating uterine fibroid disease and/or endometriosis.

However, the clinical use of such SERM compounds for the treatment of uterine fibroid disease and/or endometriosis, particularly in pre-menopausal women, has been hampered by the propensity of said compounds to have significant ovarian stimulatory effects. A great need currently exists, therefore, for new SERM compounds that behave as estrogen antagonists in the uterus that do not significantly stimulate the ovaries.

SUMMARY OF INVENTION

The present invention relates to a compound of formula I:

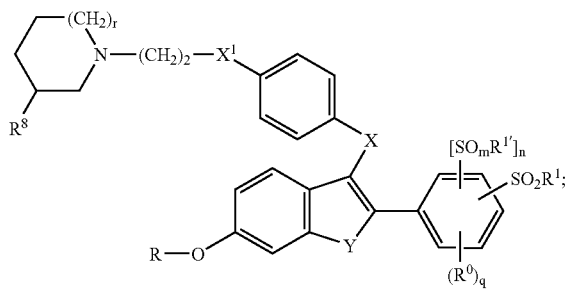

(I)

wherein:

m, q and r are independently 0, 1 or 2;

n is 0 or 1;

R is H or $COR^2$;

$R^0$ is independently at each occurrence OH, $CF_3$, halo, $C_1$-$C_6$ alkyl or $C_1$-$C_6$ alkoxy;

$R^1$ and $R^{1'}$ are independently $C_1$-$C_6$ alkyl, $C_1$-$C_6$ alkoxy, $NR^3R^{3a}$, $CF_3$ or $CH_2CF_3$; or when n and q are 0, the —$SO_2R^1$ moiety may combine with the phenyl ring to which it is attached to form a moiety of formula (a) or (b):

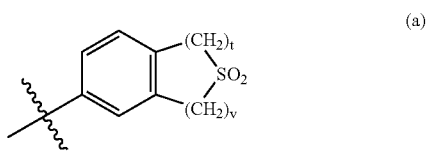

(a)

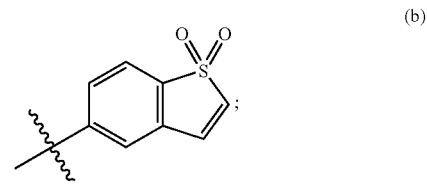

(b)

wherein t and v are 0, 1 or 2 provided that the sum of t+v must be 2;

$R^2$ is $C_1$-$C_6$ alkyl; $C_1$-$C_6$ alkoxy; $NR^4R^4$; phenoxy; or phenyl optionally substituted with halo;

$R^3$ is $C_1$-$C_6$ alkyl or phenyl;

$R^{3a}$ and $R^4$ are independently at each occurrence H, $C_1$-$C_6$ alkyl or phenyl;

X is O, $CH_2$ or CO;

$X^1$ is O or $NR^5$;

$R^5$ is H or $C_1$-$C_6$ alkyl;

$R^8$ is H or methyl provided that if r is 1 or 2, then $R^8$ must be H and that if r is 0, then $R^8$ must be methyl; and Y is S, $CH_2CH_2$ or CH=CH; or a pharmaceutical acid addition salt thereof.

The present invention also relates to a pharmaceutical composition that comprises a compound of formula I, or a pharmaceutical acid addition salt thereof, and a pharmaceutical carrier. In another embodiment, the pharmaceutical composition of the present invention may be adapted for use in treating endometriosis and/or uterine fibrosis.

The present invention also relates to methods for treating endometriosis and/or uterine fibrosis employing a compound of formula I, or a pharmaceutical acid addition salt thereof.

In addition, the present invention relates to a compound of formula I, or a pharmaceutical acid addition salt thereof, for use in treating endometriosis and/or uterine fibrosis. The present invention is further related to the use of a compound of formula I, or a pharmaceutical acid addition salt thereof, for the manufacture of a medicament for treating endometriosis and/or uterine fibrosis.

The present invention further relates to a compound of formula II:

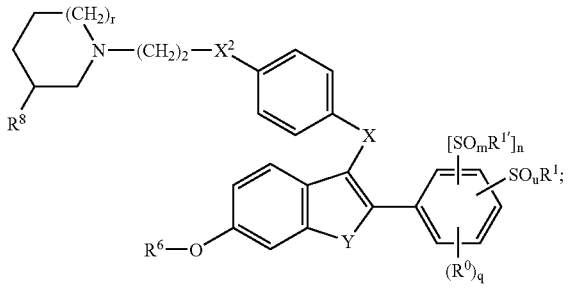

wherein:
  m, n, q, r, $R^0$, $R^1$, $R^{1'}$, $R^8$ and X and Y are as described above for the formula I compound;
  u is 0, 1 or 2;
  $R^6$ is H, $C_1$-$C_6$ alkyl, benzyl or $COR^2$ wherein $R^2$ is as described above for the formula I compound;
  $X^2$ is O or $NR^7$; and
  $R^7$ is H, $C_1$-$C_6$ alkyl or $CO_2$($C_1$-$C_6$ alkyl); provided that u can only be 2 when $R^6$ is $C_1$-$C_6$ alkyl or benzyl; or an acid addition salt thereof; provided that the compound of formula II is not:

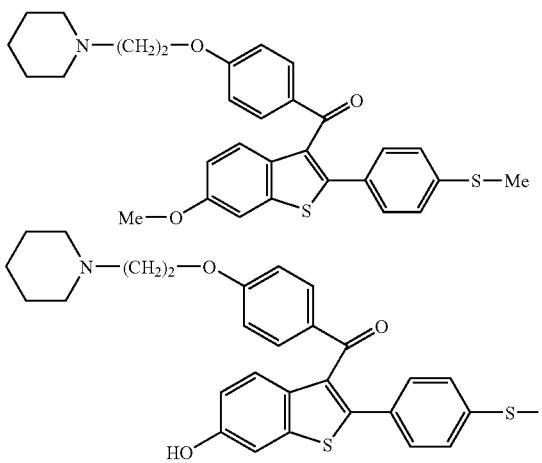

useful, e.g., as chemical intermediates to the formula I compounds.

DETAILED DESCRIPTION

For the purposes of the present invention, as disclosed and claimed herein, the following terms are defined below.

The term "halo" refers to fluoro, chloro, bromo and iodo. The term "$C_1$-$C_6$ alkyl" represents a straight, branched or cyclic hydrocarbon moiety having from one to six carbon atoms, e.g., methyl, ethyl, n-propyl, isopropyl, cyclopropyl, n-butyl, isobutyl, sec-butyl, t-butyl, cyclobutyl, pentyl, cyclopentyl, hexyl, cyclohexyl and the like. Moieties such as a cyclobutylmethylenyl are also included within the scope of a $C_1$-$C_6$ alkyl group. The term "$C_1$-$C_4$ alkyl" refers specifically to methyl, ethyl, n-propyl, isopropyl, cyclopropyl, n-butyl, isobutyl, sec-butyl, t-butyl, cyclopropylmethyl and cyclobutyl. A "$C_1$-$C_6$ alkoxy" group is a $C_1$-$C_6$ alkyl moiety connected through an oxy linkage.

The term "pharmaceutical" when used herein as an adjective means substantially non-deleterious.

Preferred Compounds (Embodiments) of the Invention

Certain compounds of the invention are particularly interesting and are preferred. The following listing sets out several groups of preferred compounds. It will be understood that each of the listings may be combined with other listings to create additional groups of preferred compounds.
  a) m is 0 or 2;
  b) m is 0;
  c) m is 2;
  d) n is 0;
  e) n is 1;
  f) q is 0 or 1;
  g) q is 0;
  h) r is 1;
  i) r is 2;
  j) R is H;
  k) R is $COR^2$;
  l) $R^0$ is OH, methoxy, $CF_3$, fluoro, chloro, methyl or ethyl;
  m) $R^0$ is OH, $CF_3$, fluoro, chloro, methyl or ethyl;
  n) $R^0$ is $CF_3$ or fluoro;
  o) the —$SO_2R^1$ moiety is at the para-position of the phenyl ring to which it is attached;
  p) the —$SO_2R^1$ moiety does not combine with the phenyl ring to which it is attached to form a moiety of formula (a) or (b);
  q) $R^1$ is $C_1$-$C_4$ alkyl or $CF_3$;
  r) $R^1$ is methyl, ethyl, n-propyl, isopropyl, cyclopropyl, n-butyl, isobutyl, sec-butyl, t-butyl, cyclobutyl or $CF_3$;
  s) $R^1$ is methyl, ethyl, cyclopropyl or $CF_3$;
  t) $R^1$ is methyl, ethyl or $CF_3$;
  u) $R^1$ is methyl;
  v) $R^1$ is ethyl;
  w) $R^1$ is cyclopropyl;
  x) $R^1$ is $CF_3$;
  y) $R^{1'}$ is $C_1$-$C_4$ alkyl or $CF_3$;
  z) $R^{1'}$ is methyl, ethyl, n-propyl, isopropyl, cyclopropyl, n-butyl, isobutyl, sec-butyl, t-butyl, cyclobutyl or $CF_3$;
  aa) $R^{1'}$ is methyl, ethyl, cyclopropyl or $CF_3$;
  bb) $R^{1'}$ is methyl, ethyl or $CF_3$;
  cc) $R^1$ is methyl;
  dd) $R^{1'}$ is ethyl;
  ee) $R^{1'}$ is cyclopropyl;
  ff) $R^1$ is $CF_3$;
  gg) $R^2$ is $C_1$-$C_6$ alkyl or phenyl;
  hh) $R^2$ is $C_1$-$C_6$ alkyl, $NHCH_3$ or phenyl;
  ii) $R^2$ is $C_1$-$C_4$ alkyl, $NHCH_3$ or phenyl;
  jj) $R^5$ is H, methyl or ethyl;
  kk) $R^5$ is H;
  ll) X is O;
  mm) $X^1$ is O;
  nn) $X^1$ is $NR^5$;
  oo) Y is S;
  pp) Y is CH=CH;
  qq) Y is $CH_2CH_2$;
  rr) the compound of formula I is the hydrochloride salt.

Synthesis

The compound of formula I may be prepared as described in the following Schemes, Preparations and Examples.

Scheme 1

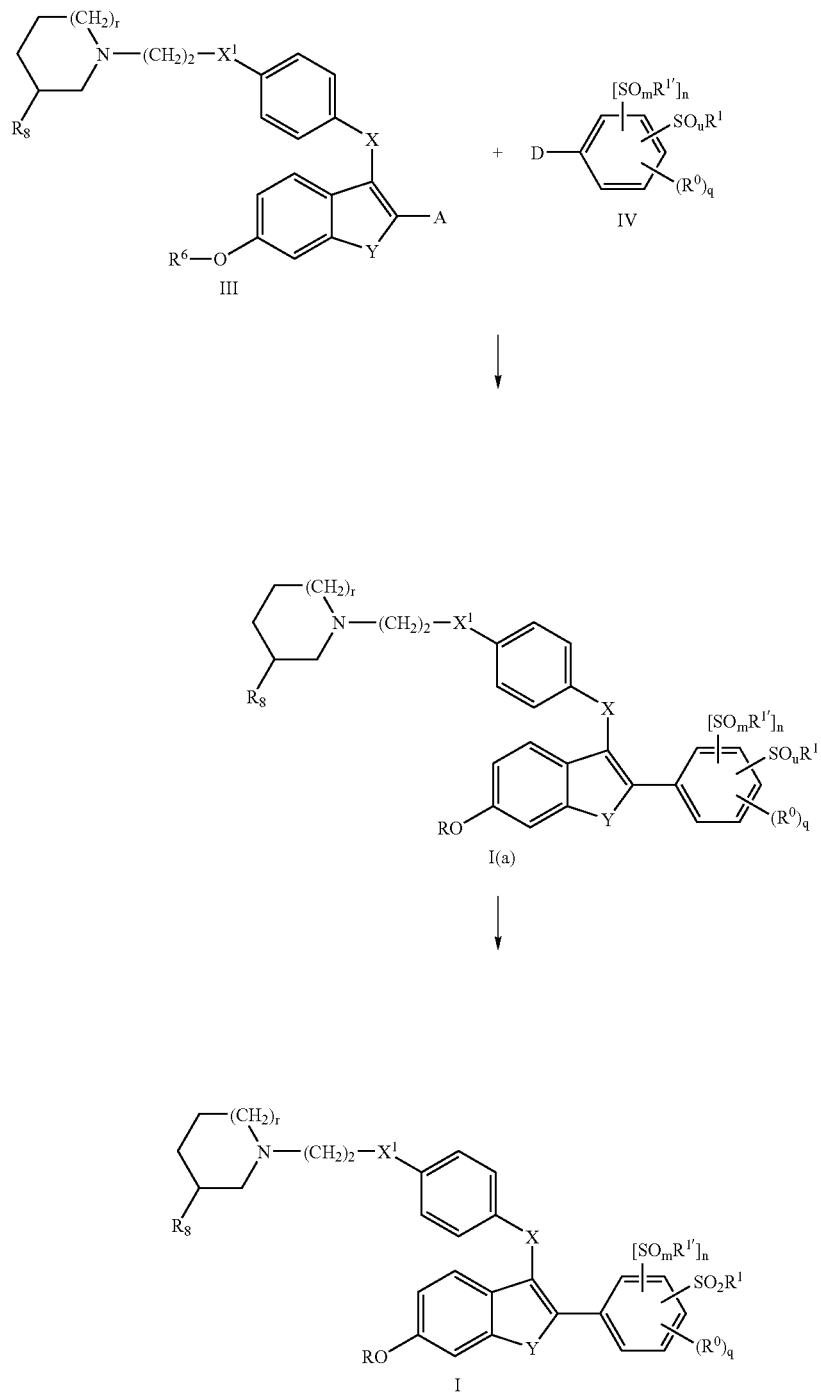

In Scheme 1, a compound of formula IV is reacted with a compound of formula III under usual "Suzuki" or "Stille" reaction conditions, i.e., wherein one of substituent "A" or "D" is a boronic acid/ester or alkyl stannane moiety and the other is a leaving group, e.g., chloro, bromo or iodo or a sulfonate group such as trifluoromethyl sulfonate. When $R^6$ is alkyl (preferably methyl) or benzyl, said $R^6$ groups may be removed under standard conditions (see, e.g., the procedures that follow or the latest edition of Greene, Protective Groups in Organic Synthesis, John Wiley & Sons, New York, N.Y.) to provide the compound of formula I where R is H. When u is 0 or 1, the coupled product may be oxidized under standard conditions (see preparations below) to prepare the corresponding mono or bis-sulfone of formula I(a) where m is 2. A formula I or I(a) compound where R is H may then be further derivatized to prepare a compound of formula I where R is $COR^2$.

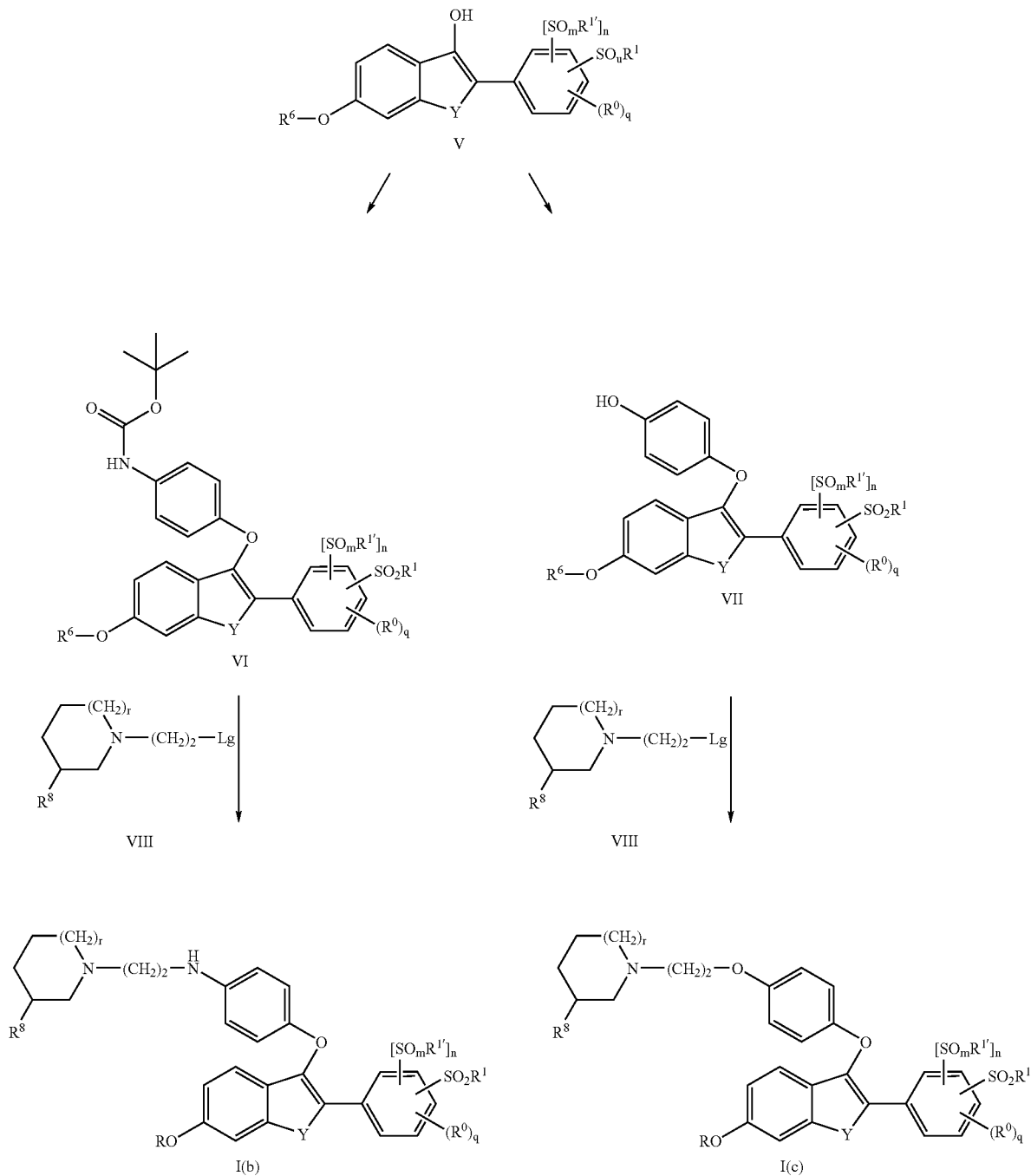

In Scheme 2, the compound of formula I(b) is formed by first reacting a compound of formula VI (prepared essentially as taught in U.S. Pat. No. 5,929,090 which is incorporated herein by reference) with a compound of formula VIII under standard nucleophilic displacement conditions to give a product compound that may be deprotected and further derivatized as described supra to give the compound of formula I(b).

The compound of formula I(c) may also be prepared from a compound of formula V as depicted in Scheme 2. The compound of formula VII may be prepared by first reacting the compound of formula V with a base followed by the addition of 4-fluoro-benzaldehyde. The product aldehyde may be converted to the corresponding hydroxy/sulfonyl compound of formula VII by reaction, e.g., first with hydrogen peroxide followed by reaction with sodium perborate monohydrate. The compound of formula VII may then be reacted with a compound of formula VIII under standard nucleophilic displacement conditions to give a product compound that may be deprotected and further derivatized as described supra to give the compound of formula I(c).

Scheme 3

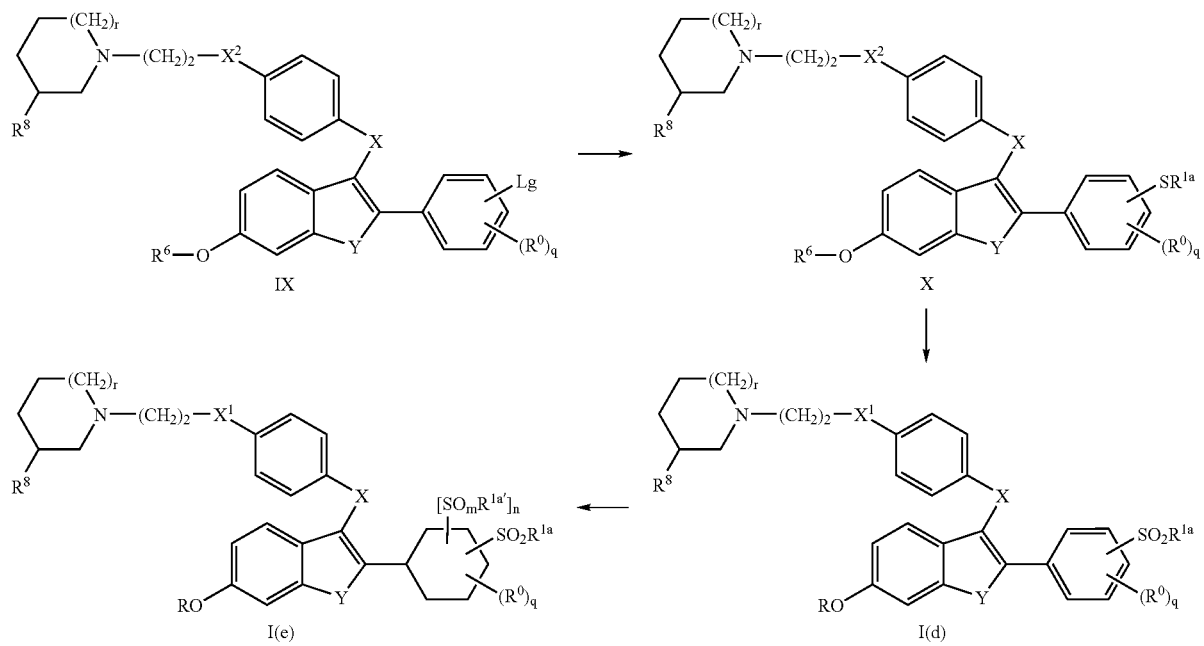

In Scheme 3, an alternative preparation of a compound of formula I where $R^1$ and $R^{1'}$ are independently $C_1$-$C_6$ alkyl, $CF_3$ or $CH_2CF_3$ and the $SO_2R^1$ moiety does not combine with the $R^0$ moiety is shown. A compound of formula IX (prepared in an analogous fashion to the reaction of a compound of formula III with a compound of formula IV described in Scheme 1) may be reacted with the thiolate of a compound of the formula $HSR^{1a}$ where $R^{1a}$ is $C_1$-$C_6$ alkyl $CF_3$ or $CH_2CF_3$, e.g., sodium methanethiolate which results in displacement of the "Lg" substituent(s). The "Lg" moiety found in the compound of formula IX is a substituent that activates the phenyl group to which it is attached toward nucleophilic aromatic substitution. The thioether formula X product may then be oxidized to form the corresponding sulfone (or sulfoxide) compound that may be deprotected and further derivatized as described supra to give the compound of formula I(d). When more than Lg substituent may be introduced into a compound of formula IV, the methodology of Scheme 3 is especially adaptable to prepare a compound of formula I(e) where n is 1 and m is 0 or 1.

Compounds of formula III, IV and VIII may be prepared as shown below or by procedures analogous to those found in the art. Compounds of formula V may be prepared by analogous procedures to those described in U.S. Pat. No. 5,929,090 or as described below. Compounds of formula $HSR^{1a}$ are, in general, commercially available or can be prepared by procedures readily available to the ordinarily skilled synthetic organic chemist.

General Experimental Details

Electrospray mass spectra is obtained, e.g., on a Finnigan LCQ Duo instrument using a mobile phase of 50% acetonitrile, 25% methanol, and 25% 2 mM aqueous ammonium acetate.

Preparative HPLC is performed, e.g., on a Gilson Preparative System with Unipoint Software and dual wavelength detection at 220 and 254 nm as well as Finnigan aQa MS. A 20-mm×250-mm ODS-AQ column with a particle size of 15 microns may be used as the stationary phase. The eluent is a binary system of bottle A (0.1% trifluoroacetic acid (TFA), 1% isopropyl alcohol (IPA) in water) and bottle B (0.05% TFA, 1% IPA in acetonitrile). The standard method is a gradient of 30-95% B unless otherwise indicated. The compounds purified by this method were isolated as TFA salts.

Preparative HPLC's may also be performed on a Biotage ParallelFlex system with proprietary dual wavelength detection and software. A 30-mm×150-mm or 19-mm×250 mm Xterra column with a particle size of 10 microns is used as the stationary phase and 10 mM $NH_4^+HCOO^-$/10 nM $NH_4OH$ is used as mobile phase A and 100% acetonitrile is used as a mobile phase B.

Preparation 1

Trifluoro-methanesulfonic acid 6-methoxy-1-[4-(2-piperidin-1-yl-ethoxy)-phenoxy]-naphthalen-2-yl ester Add 6-methoxynaphthalene-2-ol (20 g, 114.8 mmol) to dimethylformamide (DMF, 250 mL) at ambient temperature followed by N-bromosuccinimide (BS, 21.5 g, 120 mmol) over a 30 minute period. After 45 minutes, dilute with water (800 mL), collect and dry the precipitate to provide 25.5 g (87%) of 1-bromo-6-methoxy-naphthalen-2-ol.

Add 1-bromo-6-methoxy-naphthalen-2-ol (66.7 g, 264 mmol), potassium carbonate ($K_2CO_3$, 40.0 g, 290 mmol) and benzyl bromide (49.6 g, 290 mmol) to DMF (800 mL). Stir the mixture at ambient temperature for 1 hour. Add water (400 mL) to precipitate the product. Collect the precipitate and wash the filter cake with heptane (3×125 mL) then dry to provide 83.7 g of 2-benzyloxy-1-bromo-6-methoxy-naphthalene (86.2%).

Combine toluene (200 mL), 2-benzyloxy-1-bromo-6-methoxy-naphthalene (30 g, 87.4 mmol), 4-(2-piperidin-1-yl-ethoxy)phenol (23.2 g, 105 mmol) and cesium carbonate (34.4 g, 105 mmol), heat the mixture to reflux. Remove a portion of the toluene (100 mL). Add ethyl acetate (390 mg, 4.37 mmol) and copper triflate benzene complex (2.20 g, 4.37 mmol) to the reaction mixture and stir for 5 minutes. Remove the solvent by distillation and heat the resulting residue to 174° C. for 1.5 hours. Dissolve the residue in a mixture of ethyl acetate (200 mL) and aqueous HCl (1 N, 90 mL). Separate and concentrate the organics to a residue. Column chromatograph the residue to give 12.4 g of 1-{2-[4-(2-benzyloxy-6-methoxy-naphthalen-1-yloxy)-phenoxy]-ethyl}-piperidine (30%).

Add 1-{2-[4-(2-benzyloxy-6-methoxy-naphthalen-1-yloxy)-phenoxy]-ethyl}-piperidine (12.4 g, 25.5 mmol) to a methanol/ethyl acetate mixture (1:1, 490 mL) and heat to form a solution. Remove the heat and add ammonium formate (4.83 g, 76.6 mmol) and Pd(OH)$_2$ on Carbon (20% ww, 1.58 g, 1.12 mmol). Reflux for 50 minutes then filter the mixture. Concentrate the filtrate to provide 9.9 g of 6-methoxy-1-[4-(2-piperidin-1-yl-ethoxy)-phenoxy]-naphthalene-2-ol (98.5%).

Cool dichloromethane (290 mL), triethylamine (3.08 g, 30.4 mmol) and 6-methoxy-1-[4-(2-piperidin-1-yl-ethoxy)-phenoxy]-naphthalene-2-6l (9.2 g, 23.4 g) to –50° C. and add trifluoromethanesulfonic acid anhydride (7.26 g, 25.7 mmol). Stir the resulting mixture at –50° C. for 2 hours then allow the mixture to warm to ambient temperature before stirring an additional hour. Add brine (150 mL) and separate the organics. Wash the organics with NaHCO$_3$ then dry before concentrating to a residue. Crystallized the residue with ethyl ether-hexanes to provide 11.2 g of the title compound (90.9%).

Preparation 2

Trifluoro-methanesulfonic acid 6-hydroxy-1-[4-(2-piperidin-1-yl-ethoxy)-phenoxy]-naphthalen-2-yl-ester Add 2M hydrogen chloride in ether (1.5 mL, 3 mmol) to a solution of the compound of Preparation 1 (1.07 g, 2.04 mmol) in dichloromethane (20 mL) and remove solvent under vacuum. Dissolve the hydrochloride salt in dichloromethane (40 mL) and cool in ice bath. Add boron tribromide (0.58 mL, 6.12 mmol), stir for 3.5 hours, warm to ambient temperature and stir for 15 minutes, cool in ice bath and quench with ice cold saturated aqueous sodium bicarbonate. Extract aqueous layer with dichloromethane, combine organic layers and dry with magnesium sulfate, remove solvent under vacuum and chromatograph on silica gel using dichloromethane/methanol mixtures to give 990 mg of the title compound (95%).

Preparation 3

Trifluoro-methanesulfonic acid 6-benzyloxy-1-[4-(2-piperidin-1-yl-ethoxy)-phenoxy]-naphthalen-2-yl ester Combine trifluoromethanesulfonic acid 6-hydroxy-1-[4-(2-piperidin-1-yl-ethoxy)-phenoxy]-naphthalen-2-yl ester (247 mg, 0.48 mmol), triphenylphosphine (190 mg, 0.725 mmol), benzyl alcohol (0.075 mL, 0.725 mmol) and tetrahydrofuran (5 mL) in a flask placed in an ice bath. Add diisopropyl azodicarboxylate (0.14 mL, 0.725 mmol), stir for 1 hour, warm to ambient temperature and stir for 30 minutes. Dilute with ethyl acetate and wash with 50% saturated aqueous sodium bicarbonate, saturated aqueous sodium chloride, dry with magnesium sulfate and remove solvent under vacuum. Chromatograph on silica gel with dichloromethane/methanol mixtures to give 213 mg of the title compound (73%).

EXAMPLE 1

1-(2-{4-[2-(4-Methanesulfonyl-phenyl)-6-methoxy-naphthalen-1-yloxy]-phenoxy}-ethyl)-piperidine

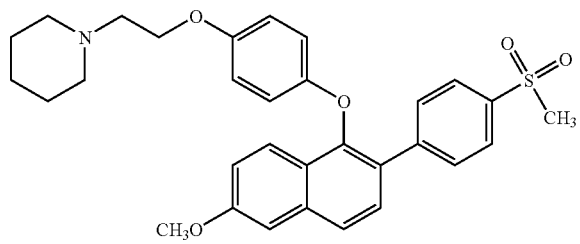

Combine 4-(methanesulfonyl)phenylboronic acid (6.8 g, 34 mmol), the compound of Preparation 1 (6.6 g, 12.6 mmol), cesium fluoride (17.2 g, 113 mmol) and acetonitrile (130 mL) in a 500 mL flame-dried flask fitted with a reflux condenser. In a separate flask combine palladium (II) acetate (283 mg, 1.26 mmol) and tricyclohexylphosphine (530 mg, 1.9 mmol). Add acetonitrile (65 mL) and sonicate for 10 minutes under nitrogen. Add the catalyst slurry to the mixture of substrates and heat in a 90° C. oil bath for 30 minutes. Cool the suspension to room temperature and filter through packed celite. Rinse the celite with ethyl acetate and wash the filtrate with a 50:50 mixture of water and saturated aqueous Na$_2$CO$_3$, saturated aqueous NH$_4$Cl, and brine. Dry the organic layer (Na$_2$SO$_4$), filter, and evaporate to obtain 10 grams of crude material. Treat this crude material with a solution of 1% methanol (MeOH) in CH$_2$Cl$_2$ and remove the resulting white solid impurity (400 mg) by filtration. Concentrate the filtrate and pre-adsorb the crude product on to silica gel. Chromatograph the residue on a SiO$_2$ column eluting the material with methanol in dichloromethane (0 to 10%) to give 5.2 grams of the title compound (78%). Concentrate the crude fractions, evaporate, and recrystallize from ethyl acetate to obtain another 1.2 grams of the title compound (18%):mass spectrum (ion spray): m/z=532.3 (M+H).

EXAMPLE 2

1-(2-{4-[2-(4-Methanesulfonyl-phenyl)-6-methoxy-naphthalen-1-yloxy]-phenoxy}-ethyl)-piperidine Hydrochloride Dissolve the product of Example 1 (6.4 g, 12.1 mmol) in a mixture of ethyl acetate, dichloromethane, and methanol (300 mL; 2.5:2.5:1). Cool the resulting solution in an ice bath and treat with 2M HCl in diethyl ether (9.1 mL, 18.2 mmol). Concentrate the solution in vacuo and dry at 50° C. (<2 mm of Hg) for 18 hours to give 6.6 grams of the title compound (96%):mass spectrum (ion spray): m/z=532.3 (M+H—HCl).

EXAMPLE 3

6-(4-Methanesulfonyl-phenyl)-5-[4-(2-piperidin-1-yl-ethoxy)-phenoxy]-naphthalen-2-ol Dissolve the product of Example 2 (6.45 g, 11.4 mmol) in dichloromethane (200 mL) and cool to 3° C. in an ice bath. Treat this solution with neat BBr$_3$ (5.4 mL, 57 mmol), dropwise over 5 minutes, and stir for 3 hours at 0 to 10° C. Slowly pour the reaction mixture into a 1-liter separatory funnel containing saturated aqueous NaHCO$_3$ (300 mL) and ice. Dilute the two-phase mixture with a solution of 7.5% MeOH in ethyl acetate (EtOAc, 400 mL) and brine (100 mL). Separate the layers and back extract the aqueous layer with 5% MeOH in EtOAc (2×150 mL). Wash the combined organic layers with brine (100 mL), dry (Na$_2$SO$_4$), filter and evaporate to obtain 5.3 g of crude product. Chromatograph the residue on a SiO$_2$ column eluting the material with methanol in dichloromethane (2.5 to 12%) to give 4.99 grams of the title compound (85%). Dry at 45° C. (<2 mm of Hg) for 18 hours:mass spectrum (ion spray): m/z=518.3 (M+H).

EXAMPLE 4

6-(4-Methanesulfonyl-phenyl)-5-[4-(2-piperidin-1-yl-ethoxy)-phenoxy]-naphthalen-2'-ol Hydrochloride Slurry the product of Example 3 (2.8 g, 5.4 mmol) in a mixture of ethyl acetate, ethyl ether, and methanol (50 mL; 5:1:4). Cool the mixture in an ice bath and treat with 2M HCl in diethyl ether (4.1 mL, 8.2 mmol). Collect the resulting solid on filter paper, rinse with diethyl ether and dry at 45° C. (<2 mm of Hg) for 18 hours to give 2.84 grams of the title compound (95%): mass spectrum (ion spray): m/z=518.3 (M+H—HCl).

EXAMPLE 5

2,2-Dimethyl-propionic acid 6-(4-methanesulfonyl-phenyl)-5-[4-(2-piperidin-1-yl-ethoxy)-phenoxy]-naphthalen-2-yl ester Hydrochloride

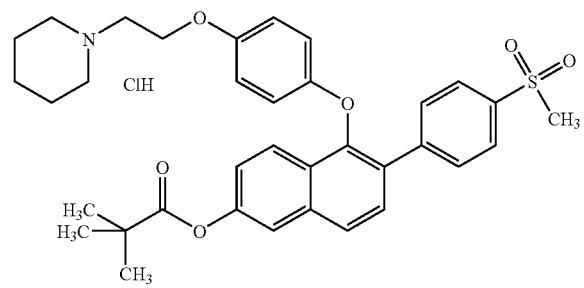

Dissolve the product of Example 3 (220 mg, 0.43 mmol) in pyridine (5 mL) and treat sequentially with trimethylacetyl chloride (0.144 mL, 1.17 mmol) and dimethylaminopyridine (DMAP, catalytic amount). Stir at ambient temperature for 18 hours and evaporate pyridine. Re-constitute the residue in ethyl acetate and wash with saturated aqueous NH$_4$Cl, saturated aqueous NaHCO$_3$, and brine. Dry the organic layer (Na$_2$SO$_4$), filter, and evaporate to obtain 277 mg of crude material. Pre-adsorb onto silica gel and chromatograph on a SiO$_2$ column eluting the material with methanol in dichloromethane (0 to 6%) to give 235 mg of 2,2-dimethyl-propionic acid 6-(4-methanesulfonyl-phenyl)-5-[4-(2-piperidin-1-yl-ethoxy)-phenoxy]-naphthalen-2-yl ester. Dissolve the free base in a mixture of ethyl acetate and diethyl ether (20 mL; 1:1). Cool in an ice bath and treat with 2M HCl in diethyl ether (0.3 mL, 0.6 mmol). Collect the precipitate on filter paper and rinse with diethyl ether to obtain 220 mg of the title compound (80%): mass spectrum (ion spray): m/z=602.4 (M+H—HCl).

EXAMPLE 6

Benzoic acid 6-(4-methanesulfonyl-phenyl)-5-[4-(2-piperidin-1-yl-ethoxy)-phenoxy]-naphthalen-2-yl ester Hydrochloride

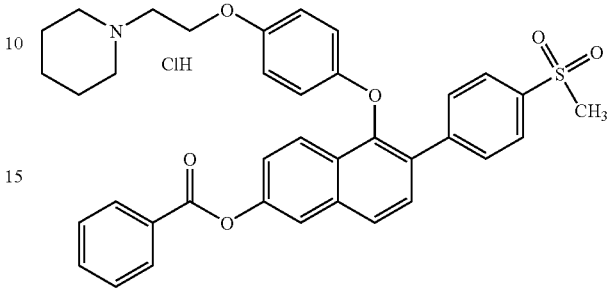

Dissolve the product of Example 3 (220 mg, 0.43 mmol) in pyridine (5 mL) and treat sequentially with benzoyl chloride (0.067 mL, 0.58 mmol), and DMAP (catalytic amount). Stir at ambient temperature for 18 hours and evaporate pyridine. Partition between saturated aqueous NH$_4$Cl and ethyl acetate (containing 8% MeOH). After separation of the layers extract the aqueous layer with ethyl acetate (containing 5% MeOH) and combine the two organic layers. Wash with saturated aqueous NaHCO$_3$ and brine. Dry the organic layer (Na$_2$SO$_4$), filter, and evaporate to obtain 276 mg of crude free base material. Pre-adsorb on to silica gel and chromatograph on a SiO$_2$ column eluting with methanol in dichloromethane (0 to 6%) to give 260 mg of benzoic acid 6-(4-methanesulfonyl-phenyl)-5-[4-(2-piperidin-1-yl-ethoxy)-phenoxy]-naphthalen-2-yl ester. Dissolve the free base in hot ethyl acetate (20 mL) and dilute with diethyl ether (20 mL). Cool in an ice bath and treat with 2M HCl in diethyl ether (0.31 mL, 0.62 mmol). Collect the precipitate on filter paper and rinse with diethyl ether to obtain 255 mg of the title compound (91%): mass spectrum (ion spray): m/z=622.3 (M+H—HCl).

EXAMPLE 7

4-Fluoro-benzoic acid 6-(4-methanesulfonyl-phenyl)-5-[4-(2-piperidin-1-yl-ethoxy)-phenoxy]-naphthalen-2-yl ester

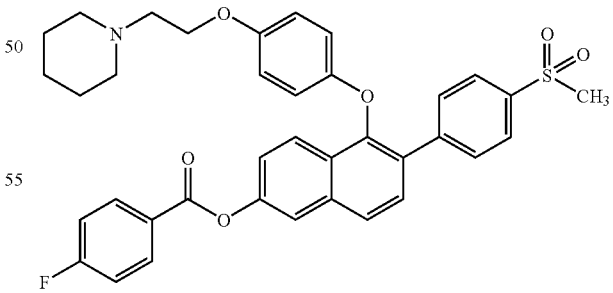

Dissolve the compound of Example 3 (111 mg, 0.21 mmol) in dichloromethane (2 mL). Add 4-fluorobenzoyl chloride (30 μL, 0.25 mmol) dropwise. After stirring for 10 minutes, pour the reaction-mixture into saturated aqueous sodium bicarbonate (10 mL) and extract with dichloromethane (10 mL). Dry the organic layer with sodium sulfate, filter and concentrate in vacuo. Chromatograph the residue on a SiO$_2$ column eluting with methanol in dichloromethane (0 to 3%) to give 99 mg of the title compound (73%): mass spectrum (ion spray): m/z=640.3 (M+H).

EXAMPLE 8

4-Fluoro-benzoic acid 6-(4-methanesulfonyl-phenyl)-5-[4-(2-piperidin-1-yl-ethoxy)-phenoxy]-naphthalen-2-yl ester Hydrochloride Dissolve the compound of Example 7 (99 mg, 0.15 mmol) in dichloromethane (3 mL) and add 2M HCl in ether (400 μL, 0.8 mmol). Remove the solvent in vacuo to yield 111 mg of the title compound (100%): mass spectrum (ion spray): m/z=640.3 (M+H—HCl).

EXAMPLE 9

Carbonic acid isobutyl ester 6-(4-methanesulfonyl-phenyl)-5-[4-(2-piperidin-1-yl-ethoxy)-phenoxy]-naphthalen-2-yl ester

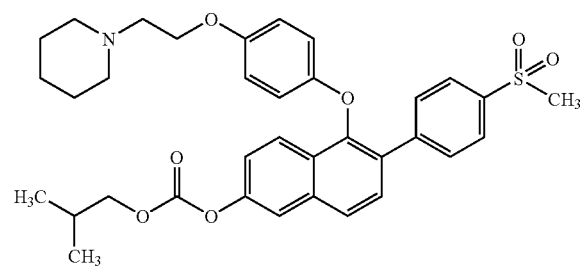

Dissolve the compound of Example 3 (120 mg, 0.23 mmol) in dichloromethane (3 mL) and add isobutylchloroformate (38 μL, 0.30 mmol) dropwise. After stirring for 10 minutes, pour the reaction into vigorously stirred ether (10 mL) and filter. Dissolve the solids in dichloromethane (10 mL) and wash with saturated aqueous sodium bicarbonate. Dry the organic layer with sodium sulfate, filter and concentrate in vacuo. Chromatograph the residue on a SiO$_2$ column eluting with methanol in dichloromethane (4%) to give 104 mg of the title compound (73%): mass spectrum (ion spray): m/z=618.4 (M+H).

EXAMPLE 10

Carbonic acid isobutyl ester 6-(4-methanesulfonyl-phenyl)-5-[4-(2-piperidin-1-yl-ethoxy)-phenoxy]-naphthalen-2-yl ester Hydrochloride Dissolve the compound of Example 9 (104 mg, 0.17 mmol) in dichloromethane (3 mL) and add 2M HCl in ether (400 μL, 0.8 mmol). Remove the solvent in vacuo to yield 81 mg of the title compound (73%): mass spectrum (ion spray): m/z=618.3 (M+H—HCl).

EXAMPLE 11

Methyl-carbamic acid 6-(4-methanesulfonyl-phenyl)-5-[4-(2-piperidin-1-yl-ethoxy)-phenoxy]-naphthalen-2-yl ester

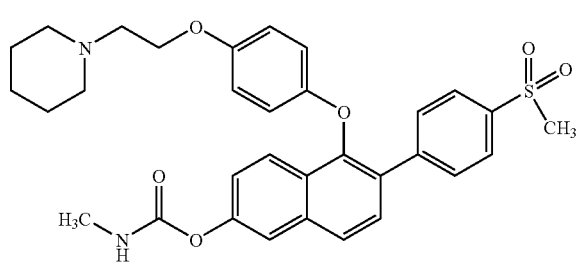

Dissolve the compound of Example 3 (201 mg, 0.38 mmol) in dichloromethane (4 L) and add triethylamine (0.50 mL, 3.5 mmol) followed by methylisocyanate (500 mg, 8.7 mmol). After stirring for 30 minutes, pour the reaction mixture into saturated aqueous sodium bicarbonate and extract with dichloromethane. Dry the organic layer with sodium sulfate, filter and concentrate in vacuo. Chromatograph the residue on a SiO$_2$ column eluting with methanol in dichloromethane (0 to 4%) to give 130 mg of the title compound (60%): mass spectrum (ion spray): m/z=575.3 (M+H) and 518.3 (M-MeNCO).

EXAMPLE 12

Methyl-carbamic acid 6-(4-methanesulfonyl-phenyl)-5-[4-(2-piperidin-1-yl-ethoxy)-phenoxy]-naphthalen-2-yl ester Hydrochloride Dissolve the compound of Example 11 (130 mg, 0.23 mmol) in dichloromethane (3 mL) and add 2M HCl in ether (400 μL, 0.8 mmol). Remove the solvent in vacuo to yield 81 mg of the title compound (73%): mass spectrum (ion spray): m/z=575.3 (M+H—HCl) and 518.3 (M+H—HCl-MeNCO).

EXAMPLE 13

1-(2-{4-[2-(4-Ethanesulfonyl-phenyl)-6-methoxy-naphthalen-1-yloxy]-phenoxy}-ethyl)-piperidine Hydrochloride Combine 4-(ethanesulfonyl)phenyl)boronic acid (1.83 g, 8.6 mmol), the compound of Preparation 1 (1.5 g, 2.86 mmol), cesium fluoride (3.9 g, 25.7 mmol) and acetonitrile (32 mL) in a 100 mL flame-dried flask fitted with a reflux condenser. In a separate dried flask combine palladium (II) acetate (65 mg, 0.29 mmol) and tricyclohexylphosphine (120 mg, 0.43 mmol). Add acetonitrile (16 mL) and sonicate for 10 minutes under nitrogen. Add the catalyst slurry to the mixture of substrates and heat in a 90° C. oil bath for 30 minutes. Cool the suspension to room temperature and filter through packed celite. Rinse the celite with ethyl acetate and wash the filtrate with a 50:50 mixture of water and saturated aqueous $Na_2CO_3$, saturated aqueous $NH_4Cl$, and brine. Dry the organic layer ($Na_2SO_4$), filter, and evaporate to obtain 2 grams of crude material. Pre-adsorb the crude material onto silica gel and chromatograph on a $SiO_2$ column eluting with methanol in dichloromethane (0 to 10%) to give 1.5 grams of 1-(2-{4-[2-(4-ethanesulfonyl-phenyl)-6-methoxy-naphthalen-1-yloxy]-phenoxy}-ethyl)-piperidine. Dissolve the free base in a mixture of ethyl acetate and diethyl ether (60 mL; 1:1). Cool in an ice bath and treat with 2M HCl in diethyl ether (2 mL, 4 mmol). Collect the precipitate on filter paper and rinse with diethyl ether to obtain 1.5 grams of the title compound (90%): mass spectrum (ion spray): m/z=546.3 (M+H).

EXAMPLE 14

6-(4-Ethanesulfonyl-phenyl)-5-[4-(2-piperidin-1-yl-ethoxy)-phenoxy]-naphthalen-2-ol Hydrochloride Using the product from Example 13 (1.5 g, 2.58 mmol) and the procedure described in Example 3, prepare 1.35 grams of 6-(4-ethanesulfonyl-phenyl)-5-[4-(2-piperidin-1-yl-ethoxy)-phenoxy]-naphthalen-2-ol. Dissolve the free base in a mixture of ethyl acetate and diethyl ether (60 mL; 1:1). Cool in an ice bath and treat with 2M HCl in diethyl ether (2 mL, 4 mmol). Collect the precipitate on filter paper, rinse with diethyl ether and dry at 50° C. (<2 mm of Hg) for 18 hours to give 1.3 grams of the title compound (89%): mass spectrum (ion spray): m/z=532.3 (M+H).

EXAMPLE 15

1-(2-{4-[2-(3-Methanesulfonyl-phenyl)-6-methoxy-naphthalen-1-yloxy]-phenoxy}-ethyl)-piperidine

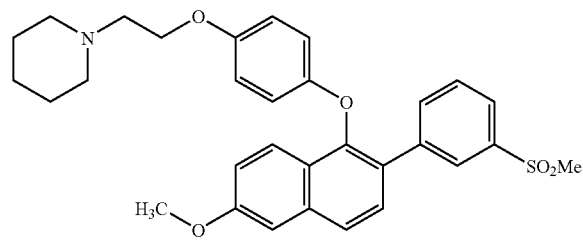

Combine palladium (II) acetate (17 mg, 0.076 mmol), tricyclohexylphosphine (PCy$_3$, 32 mg, 0.11 mmol) and acetonitrile (4 mL). Sonicate the mixture for 5 minutes. Combine the compound of Preparation 1 (400 mg, 0.76 mmol), cesium fluoride (1.00 g, 6.62 mmol) 3-(methanesulfonyl)phenylboronic acid (460 mg, 2.30 mmol) and acetonitrile (12 mL). Add the sonicated Pd/PCy$_3$ suspension to the reaction vessel and heat to 90° C. for 30 minutes. Cool to room temperature and filter through a pad of Celite and evaporate the solvent. Dissolve the residue in ethyl acetate (20 mL) and wash with saturated aqueous NaHCO$_3$ (10 mL). Separate the layers, wash the organic layer with brine (10 mL), dry with MgSO$_4$, filter, and concentrate in vacuo. Chromatograph the residue on a SiO$_2$ column eluting with methanol in dichloromethane (0 to 5%) to give 270 mg of title compound (67%): mass spectrum (ion spray): m/z=532.3 (M+H).

EXAMPLE 16

6-(3-Methanesulfonyl-phenyl)-5-[4-(2-piperidin-1-yl-ethoxy)-phenoxy]-naphthalen-2-ol Hydrochloride Dissolve the product of Example 15 in ethyl acetate (10 mL) and diethyl ether (5 mL). Add 2M HCl in diethyl ether (1 mL, 2.0 mmol). Concentrate the slurry and dry in vacuo. Dilute the residue in dichloromethane (5.0 mL) and blanket with nitrogen. Cool the solution to 0° C. with an external ice bath and add 1M BBr$_3$ in dichloromethane (1.0 mL, 1.0 mmol). After 20 minutes, dilute the reaction mixture with ethyl acetate (25.0 mL) and add saturated aqueous NaHCO$_3$ in parts (2×10 mL). Separate the layers, wash the organic layer with brine (10 mL), dry with MgSO$_4$, filter, and concentrate in vacuo. Chromatograph the residue on a SiO$_2$ column eluting 6-(3-methanesulfonyl-phenyl)-5-[4-(2-piperidin-1-yl-ethoxy)-phenoxy]-naphthalen-2-ol with a step gradient of methanol in dichloromethane (0 to 5%). Dissolve the free base in diethyl ether (5.0 mL), ethyl acetate (6.0 mL) and methanol (1.0 mL) and add 2M HCl in diethyl ether (1 mL, 2.0 mmol). Collect the precipitate on filter paper, rinse with diethyl ether and dry in vacuo (<2 mm of Hg) at 65° C. for 48 hours to give 73 mg of the title compound (26%): mass spectrum (ion spray): m/z=518.5 (M[free base]+1).

Preparation 4

3-Fluoro-4-(methanesulfonyl)phenyl boronic acid

Combine 4-bromo-2-fluorothioanisole (U.S. Pat. No. 6,307,047, 2.7 g, 12 mmol), oxone (38 g, 62 mmol) and methanol (200 mL) and stir for 12 hours. Filter through a pad of silica gel and elute with ethyl acetate (500 mL). Evaporate solvent and partition between dichloromethane (200 mL) and water (100 mL). Separate the layers, wash the organic layer with saturated aqueous NaHCO$_3$ (10 mL), brine (10 mL), dry with MgSO$_4$, filter, and concentrate in vacuo. Wash the crude solid with hexane (20 mL), ether (10 mL) and dry in vacuo to obtain 2.4 g of 4-bromo-2-fluoro-1-methanesulfonyl-benzene (78%).

Combine 4-bromo-2-fluoro-1-methanesulfonyl-benzene (1.7 g, 6.7 mmol), [1,1'-bis(diphenylphosphino)ferrocene]dichloropalladium(II) complex with dichloromethane (Pd(dppf)Cl$_2$.CH$_2$Cl$_2$, 164 mg, 0.20 mmol), bis(pinacolato)diboron (1.79 g, 7.0 mmol), potassium acetate (2 g, 20 mmol) and dimethylsulfoxide (DMSO, 100 mL). Heat the reaction mixture at 90° C. for 1 hour. Cool to room temperature and dilute with ethyl acetate (20 mL). Wash with brine (10 mL), dry with MgSO$_4$, filter, and concentrate in vacuo. Chromatograph the residue on a SiO$_2$ column eluting the material with ethyl acetate in hexane (30%) to give 1.74 g (80%) of 2-(3-fluoro-4-methanesulfonyl-phenyl)-4,4,5,5-tetramethyl-[1,3,2]dioxaborolane.

Combine 2-(3-fluoro-4-methanesulfonyl-phenyl)-4,4,5,5-tetramethyl-[1,3,2]dioxaborolane (222 mg, 0.74 mmol), NaIO$_4$ (474 mg, 2.2 mmol), tetrahydrofuran (THF, 4 mL) and water (1 mL). Stir for 2 hours and add 2M HCl in diethyl ether (0.2 mL). Stir another 12 hours and filter away the solid. Wash the filtrate with brine (10 mL), dry with MgSO$_4$ and evaporate the solvent. Wash the solid with hexane (2×10 mL) and ether (10 mL). Dry the solid under vacuum to obtain 68 mg of the title compound (42%).

EXAMPLE 17

1-(2-{4-[2-(3-Fluoro-4-methanesulfonyl-phenyl)-6-methoxy-naphthalen-1-yloxy]-phenoxy}-ethyl)-piperidine

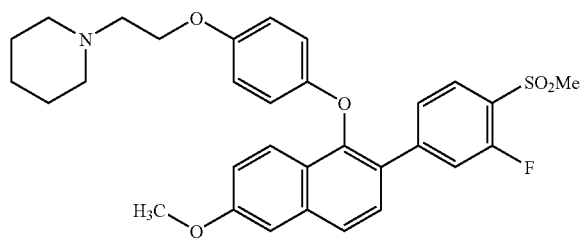

Combine palladium (II) acetate (4.2 mg, 0.019 mmol), tricyclohexylphosphine (10 mg, 0.036 mmol), the compound of Preparation 1 (92 mg, 0.18 mmol), cesium fluoride (201 mg, 1.33 mmol) 3-fluoro-4-(methanesulfonyl)phenyl boronic acid (68 mg, 0.31 mmol) and acetonitrile (10 mL). Heat to 90° C. for 1 hour. Cool to room temperature and dilute the solution with ethyl acetate (20 mL) and wash with saturated aqueous NaHCO$_3$ (10 mL). Separate the layers, wash the organic layer with brine (10 mL), dry with MgSO$_4$, filter, and concentrate in vacuo. Chromatograph the residue on a SiO$_2$ column eluting with methanol in dichloromethane (2 to 4%) to give 69 mg of title compound (72%): mass spectrum (ion spray): m/z=550.4 (M+H).

EXAMPLE 18

6-(3-Fluoro-4-methanesulfonyl-phenyl)-5-[4-(2-piperidin-1-yl-ethoxy)-phenoxy]-naphthalen-2-ol Hydrochloride Dissolve the product of Example 17 in ethyl acetate (10 mL) and diethyl ether (5 mL). Add 2M HCl in diethyl ether (1 mL, 2.0 mmol). Concentrate the slurry and dry in vacuo. Dilute the residue in dichloromethane (5.0 mL) and blanket with nitrogen. Cool the solution to 0° C. with an external ice bath. Add 1M BBr$_3$ in dichloromethane (0.1 mL, 1.1 mmol) and stir for 1 hour. Add water (1.0 mL) and dichloromethane (10 mL). Separate the layers, wash the organic layer with saturated aqueous NaHCO$_3$ (10 DE) and brine (10 mL), dry with MgSO$_4$, filter, and concentrate in vacuo. Chromatograph the residue on a SiO$_2$ column eluting 6-(3-fluoro-4-methanesulfonyl-phenyl)-5-[4-(2-piperidin-1-yl-ethoxy)-phenoxy]-naphthalen-2-ol with a step gradient of methanol in dichloromethane (0 to 5%). Dissolve the free base in diethyl ether (5.0 mL), ethyl acetate (6.0 mL) and methanol (1.0 mL) and add 2M HCl in diethyl ether (1 mL, 2.0 mmol). Collect the precipitate on filter paper, rinse with diethyl ether and dry in vacuo (<2 mm of Hg) at 65° C. for 48 hours to give 19 mg of the title compound (26%): mass spectrum (ion spray): m/z=536.3 (M+H).

Preparation 5

2-(4-Trifluoromethanesulfonyl-phenyl)-4,4,5,5-tetramethyl-[1,3,2]dioxaborolane

Dissolve 1-bromo-4-trifluoromethyl sulfide (2.5 g, 9.7 mmol) in dichloromethane (100 mL) in a 250 mL flask equipped with a reflux condenser. Add meta-chloroperbenzoic acid (mCPBA, 6.1 g, 24.3 mmol, 68%) and heat the reaction to reflux for 3 days. Cool the reaction to room temperature and wash the organic layer with 1N aqueous NaOH (100 mL). Separate and dry the organic layer with sodium sulfate. Filter and concentrate in vacuo to yield 2.5 g of 1-bromo-4-trifluoromethanesulfonyl-benzene (90%).

Charge a flame-dried flask with 1-bromo-4-trifluoromethanesulfonyl-benzene (500 mg, 1.73 mmol), bis(pinacolato)diboron (523 mg, 2.07 mmol), [1,1'-bis(diphehylphosphino)ferrocene]dichloropalladium(II), complex with dichloromethane (1:1) (42 mg, 0.05 mmol) and potassium acetate (467 mg, 5.2 mmol). Dissolve the solids with dimethylsulfoxide (9 mL) and heat to 80° C. under nitrogen for 4 hours. Cool the reaction to room temperature and dilute with benzene (50 mL). Wash the organic layer with water (20 mL) and brine (20 mL). Dry the organic layer with sodium sulfate, filter and concentrate in vacuo. Chromatograph the resultant oil on a SiO$_2$ column eluting with ethyl acetate in hexanes (20%) to yield 560 mg of the title compound (96%).

EXAMPLE 19

1-(2-{4-[6-Methoxy-2-(4-trifluoromethanesulfonyl-phenyl)-naphthalen-1-yloxy]-phenoxy}-ethyl)-piperidine

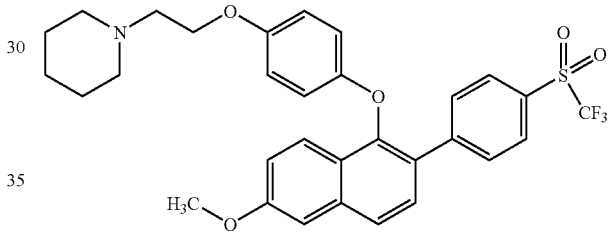

Combine 2-(4-trifluoromethanesulfonyl-phenyl)-4,4,5,5-tetramethyl-[1,3,2]dioxaborolane (560 mg, 1.67 mmol), the compound of Preparation 1 (300 mg, 0.57 mmol) and cesium fluoride (433 mg, 2.85 mmol) in a flame-dried flask fitted with a reflux condenser. In a separate dried flask combine palladium (II) acetate (25 mg, 0.11 mmol) and tricyclohexylphosphine (48 mg, 0.17 mmol). Add dry acetonitrile (6 mL) and sonicate for 10 minutes under nitrogen. Add the catalyst mixture to the solids and plunge the flask into a 90° C. oil bath. After 25 minutes cool the black suspension to room temperature and filter through celite with dichloromethane. Concentrate the filtrate in vacuo. Chromatograph the resultant residue on a SiO$_2$ column eluting with 2.5% methanol in dichloromethane with 0.2% ammonium hydroxide to give 254 mg of the title compound (76%): mass spectrum (ion spray): m/z=586 (M+H).

EXAMPLE 20

5-[4-(2-Piperidin-1-yl-ethoxy)-phenoxy]-6-(4-trifluoromethanesulfonyl-phenyl)-naphthalen-2-ol Dissolve the compound of Example 19 (250 mg, 0.42 mmol) in dichloromethane (5 mL). Add 2M HCl in ether (0.42 mL, 0.84 mmol) and stir for 1 minute. Remove the solvent in vacuo and place on a high vacuum pump for 10 minutes. Dissolve the foam in dry dichloromethane (5 mL), cool to 0° C. and add BBr$_3$ (0.20 mL, 2.1 mmol), dropwise. After 25' minutes, slowly pour into saturated aqueous sodium bicarbonate (10 mL) and extract with dichloromethane (2×10 mL). Dry the combined organic layers with sodium sulfate and concentrate in vacuo. Chromatograph the residue on a SiO$_2$ column eluting with methanol (3 to 5%) in dichloromethane with 0.2% ammonium hydroxide to yield 196 mg of the title compound (81%): mass spectrum (ion spray) m/z=572.3 (M+H).

EXAMPLE 21

5-[4-(2-Piperidin-1-yl-ethoxy)-phenoxy]-6-(4-trifluoromethanesulfonyl-phenyl)-naphthalen-2-ol Hydrochloride Dissolve the compound of Example 20 (196 mg, 0.34 mmol) in ethyl acetate (1 mL) and diethyl ether (9 mL). Add 2M HCl in diethyl ether (340 μl, 680 μmol) to the stirred solution. Allow the suspension to stir for 10 minutes. Filter the solids through a Buchner funnel. Dry the solids overnight at 45° C. in a vacuum oven to yield 98 mg of the title compound (47%): mass spectrum (ion spray) m/z=572.3 (M+H—HCl).

Preparation 6

2-(1,1-Dioxo-2,3-dihydro-1H-1λ$^6$-benzo[b]thiophen-5-yl)-4,4,5,5-tetramethyl-[1,3,2]dioxaborolane Dissolve 5-bromo-2,3-dihydro-benzo[b]thiophene (*J. Am. Chem. Soc*, 1973, 1916-1925, 4.3 g, 20 mmol) in MeOH (100 mL) and add oxone (36.9 g, 60 mmol). Stir the reaction mixture at room temperature overnight, and then remove the solid by filtration. Concentrate the filtrate and purify the residue by flash column chromatography (silica gel, 20-40% EtOAc/Hexane) to give 4.24 g of 5-bromo-2,3-dihydro-benzo[b]thiophene 1,1-dioxide (86%).

Dissolve 5-bromo-2,3-dihydro-benzo[b]thiophene 1,1-dioxide (2.0 g, 8.1 mmol) in DMSO (60 mL). Add bis(pinacolato)diboron (2.26 g, 8.9 mmol), PdCl$_2$(dppf).CH$_2$Cl$_2$ (330 mg, 0.41 mmol), and potassium acetate (KOAc, 2.38 g, 24.3 mmol). Flush the flask with N$_2$, and then heat the reaction mixture to 80° C. with stirring. Continue to heat the reaction mixture for 3 hours, and then cool to room temperature. Add water (100 mL) and extract the aqueous layer with EtOAc (3×100 mL). Combine the organic layers and dry with Na$_2$SO$_4$, filter, concentrate and purify by flash column chromatography (silica gel, 10 to 50% ethyl acetate in hexanes) to give 1.4 g (59%) of the title compound.

EXAMPLE 22

1-(2-{4-[2-(1,1-Dioxo-2,3-dihydro-1H-1λ$^6$-benzo[b]thiophen-5-yl)-6-methoxy-naphthalen-1-yloxy]-phenoxy}-ethyl)-piperidine

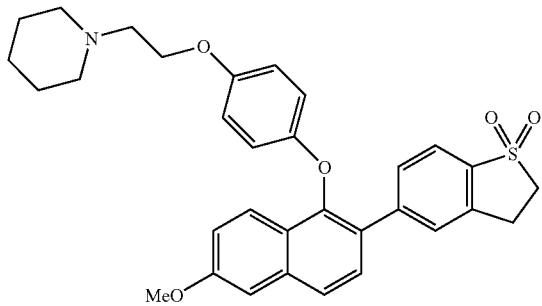

Dissolve 2-(1,1-dioxo-2,3-dihydro-1H-1λ$^6$-benzo[b]thiophen-5-yl)-4,4,5,5-tetramethyl-[1,3,2]dioxaborolane (590 mg, 2.02 mmol) and the compound of Preparation 1 (350 mg, 0.67 mmol) in CH$_3$CN (8 mL). Add palladium (II) acetate (Pd(OAc)$_2$, 15 mg, 0.007 mmol), tricyclohexylphosphine (28 mg, 0.1 mmol), and CsF (910 mg, 6 mmol). Flush the flask with N$_2$, and then heat the reaction mixture to 90° C. with stirring. Continue to heat the reaction mixture for 6 hours, and then cool to room temperature. Add water (50 mL) and extract the aqueous layer with CH$_2$Cl$_2$ (3×25 mL). Combine the organic layers and dry with Na$_2$SO$_4$, filter, concentrate and purify by flash column chromatography (silica gel, 0-4% MeOH—NH$_4$OH (10/1, v/v)/CH$_2$Cl$_2$) to give 160 mg of the title compound (44%): mass spectrum (ion spray): m/z=544.3 (M+H).

EXAMPLE 23

6-(1,1-Dioxo-2,3-dihydro-1H-1λ$^6$-benzo[b]thiophen-5-yl)-5-[4-(2-piperidin-1-yl-ethoxy)-phenoxy]-naphthalen-2-ol Hydrochloride Dissolve the compound of Example 22 (160 mg, 0.29 mmol) in CH$_2$Cl$_2$ (5 mL) and cool the solution to −78° C. Add HCl (0.2 mL, 2.0 M in diethyl ether (Et$_2$O)) and stir the reaction mixture for 10 minutes. Remove the solvent under reduced pressure and then dissolve the solid in CH$_2$Cl$_2$ (5 mL) under N$_2$. Cool the solution to 0° C. and add BBr$_3$ (370 mg, 1.46 mmol). Stir the reaction for one hour and add water (20 mL). Extract the aqueous layer with CH$_2$Cl$_2$ (3×20 mL). Combine the organic layers and dry with Na$_2$SO$_4$, filter, concentrate and purify by flash column chromatography (silica gel, 2-8% MeOH—NH$_4$OH (10/1, v/v)/CH$_2$Cl$_2$) to give 6-(1,1-dioxo-2,3-dihydro-1H-1λ$^6$-benzo[b]thiophen-5-yl)-5-[4-(2-piperidin-1-yl-ethoxy)-phenoxy]-naphthalen-2-ol. Dissolve the free base in CH$_2$Cl$_2$ (5 mL) and cool to −78° C. Add HCl (0.5 mL, 2.0 M in Et$_2$O) and stir the solution for 10 minutes. Remove the solvent under reduced pressure to give a solid. Dry the solid at 40° C., overnight, in vacuo to give 42 mg of the title compound (21%): mass spectrum (ion spray): m/z=530.3 (M+H).

Preparation 7

(2,2-Dioxo-2,3-dihydro-1H-2λ$^6$-benzo[c]thiophen-5-yl)-trimethyl-stannane

Dissolve 4-bromo-1,2-bis-bromomethyl-benzene (*J. Org. Chem*., 1418-1421, 1985; 3.42 g, 9.96 mmol) in a 2 to 1 mixture of ethanol (EtOH) and THF (1196 mL) and heat the solution to 70° C. with stirring. Add a solution of Na$_2$SO$_9$H$_2$O (2.63 g, 10.96 mmol) in water (40 mL), dropwise, over 10 hours using a syringe pump. Continue to heat and stir for another 10 hours. Cool to room temperature and remove the organic solvent under reduced pressure. Add water (200 mL) to the residue and extract the aqueous layer with EtOAc (3×200 mL). Combine the organic layers and dry with Na$_2$SO$_4$, filter, concentrate and purify by flash column chromatography (silica gel, hexanes) to give 1.27 g of 5-bromo-1,3-dihydro-benzo[c]thiophene (59%).

Dissolve 5-bromo-1,3-dihydro-benzo[c]thiophene (1.25 g, 5.79 mmol) in methanol (25 mL) and add oxone (10.7 g, 17.4 mmol). Stir the reaction mixture for 2 hours at 0° C. and then add a 1M aqueous sodium bisulfite solution (100 mL). Stir the reaction mixture for 10 minutes and add saturated NaHCO$_3$ solution (200 mL). Extract the aqueous layer with CH$_2$Cl$_2$ (3×100 mL). Combine the organic layers and dry with Na$_2$SO$_4$, filter, concentrate and purify by flash column chromatography (silica gel, 0-5% MeOH/CH$_2$Cl$_2$) to give 930 mg of 5-bromo-1,3-dihydro-benzo[c]thiophene 2,2-dioxide (65%).

Dissolve 5-bromo-1,3-dihydro-benzo[c]thiophene (860 mg, 3.50 mmol) and hexamethylditin (3 eq.) in toluene and add tetrakis(triphenylphosphine)palladium(0) (Pd(PPh$_3$)$_4$, 0.1 eq.). Flush the flask with N$_2$ and then heat the mixture to 120° C. with stirring. Continue to heat the mixture for 5 hours and then cool to room temperature. Add water (50 mL) and extract aqueous layer with EtOAc (3×50 mL). Combine the organic layers and dry with Na$_2$SO$_4$, filter, concentrate and purify by flash chromatography (silica gel, 10-30% EtOAc/hexane) to give 1.22 g of the title compound (100%).

EXAMPLE 24

1-(2-{4-[2-(2,2-Dioxo-2,3-dihydro-1H-2λ$^6$-benzo[c]thiophen-5-yl)-6-methoxy-naphthalen-1-yloxy]-phenoxy}-ethyl)-piperidine

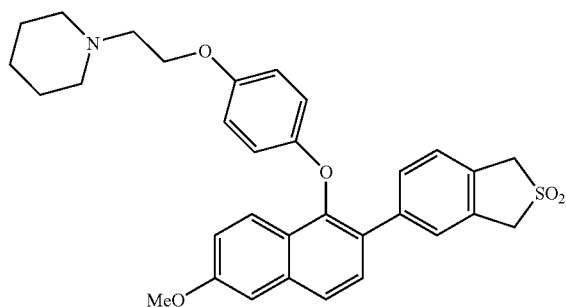

Dissolve (2,2-dioxo-2,3-dihydro-1H-2λ$^6$-benzo[c]thiophen-5-yl)-trimethyl-stannane (1.19 g, 3.6 mmol, 2.7 eq.) and the compound of Preparation 1 (630 mg, 1.2 mmol) in CH$_3$CN. Add Pd(OAc)$_2$ (0.1 eq.), tricyclohexylphosphine (0.15 eq.), and CsF (4 eq.). Flush the flask with N$_2$ and then heat the reaction mixture to 90° C. with stirring. Continue to heat the reaction mixture for one hour and then cool to room temperature. Add water (100 mL), separate, and extract the aqueous layer with CH$_2$Cl$_2$ (3×100 mL). Combine the organic layers and dry with Na$_2$SO$_4$, filter, concentrate and purify by flash column chromatography (silica gel, 0-5% MeOH—NH$_4$OH (10/1, v/v)/CH$_2$Cl$_2$) to give 140 mg of the title compound (22%): mass spectrum (ion spray): m/z=544.2 (M+H).

EXAMPLE 25

6-(2,2-Dioxo-2,3-dihydro-1H-2λ$^6$-benzo[c]thiophen-5-yl)-5-[4-(2-piperidin-1-yl-ethoxy)-phenoxy]-naphthalen-2-ol Hydrochloride Demethylate 1-(2-{4-[2-(2,2-dioxo-2,3-dihydro-1H-2λ$^6$-benzo[c]thiophen-5-yl)-6-methoxy-naphthalen-1-yloxy]-phenoxy}-ethyl)-piperidine (140 mg, 0.26 mmol) with BBr$_3$ and salify in a procedure similar to that used in Example 23 to give 130 mg (94%) of the title compound: mass spectrum (ion spray): m/z=530.2 (M+H—HCl).

Preparation 8

(4-Methanesulfonyl-3-methoxy-phenyl)-trimethyl-stannane

Dissolve 6-hydroxy-1,3-benzoxathiol-2-one (16.8 g, 0.1 mol) in THF (1650 mL) and cool to 0° C. Sequentially add benzyl alcohol (16.2 g, 0.15 mol), triphenylphosphine (PPh$_3$, 39.3 g, 0.15 mol), and diisopropylazodicarboxylate (30.3 g, 0.15 mol). Stir the reaction mixture at room temperature overnight. Add water (1500 mL) and extract the aqueous layer with EtOAc (3×1500 mL). Combine the organic layers and dry with Na$_2$SO$_4$, filter, concentrate and purify by flash column chromatography (silica gel, 10-25% of EtOAc/hexane) to give 24.33 g of 6-benzyloxy-benzo[1,3]oxathiol-2-one (94%).

Dissolve 6-benzyloxy-benzo[1,3]oxathiol-2-one (24.33 g, 94.29 mmol) in dioxane (1000 mL) and add a KOH solution (94.29 mL, 188 mmol, 2M in water) with stirring. Flush the flask with N$_2$ and then heat the reaction mixture to 80° C. for 2 hours. Cool the reaction mixture to room temperature and remove the solvent under reduced pressure. Adjust the pH to <2 with HCl (200 mL, 1.0 M in water). Extract the aqueous layer with EtOAc (3×500 mL). Combine the organic layers and dry with Na$_2$SO$_4$, filter and concentrate to give 17.8 g of 5-benzyloxy-2-mercapto-phenol (81.4%).

Dissolve 5-benzyloxy-2-mercapto-phenol (17.8 g, 76.72 mmol) in DMF (300 mL) and add K$_2$CO$_3$ (31.8 g, 0.23 mol) and MeI (32.7 g, 0.23 mol). Stir the reaction mixture at room temperature overnight. Add water (800 mL) and extract the aqueous layer with EtOAc (3×800 mL). Combine the organic layers and dry with Na$_2$SO$_4$, filter, concentrate and purify by flash column chromatography (silica, 5-20% of EtOAc/hexane) to give 13.5 g of 4-benzyloxy-2-methoxy-1-methylsulfanyl-benzene (68%).

Dissolve 4-benzyloxy-2-methoxy-1-methylsulfanyl-benzene (5.2 g, 20 mmol) in CH$_2$Cl$_2$ (250 mL) and treat with m-CPBA (15.2 g, 60 mmol, 68%). Stir the reaction mixture at room temperature for 6 hours. Add saturated K$_2$CO$_3$ (200 mL), and extract the aqueous layer with EtOAc (3×200 in mL). Combine the organic layers and dry with Na$_2$SO$_4$, filter, concentrate and purify by flash column chromatography (silica gel, 20-50% of EtOAc/hexane) to give 5.57 g of 4-benzyloxy-1-methanesulfonyl-2-methoxy-benzene (96%).

Dissolve 4-benzyloxy-1-methanesulfonyl-2-methoxy-benzene (5.57 g, 19.09 mmol) in MeOH (200 mL), under N$_2$, and add 5% Pd—C (900 mg). Evacuate the reaction vessel and flush with hydrogen gas (3 times). Stir the reaction mixture at room temperature for 3 hours, under 1 atmosphere of hydrogen gas. Filter, concentrate, and purify the reaction mixture by flash column chromatography (silica gel, 30-60% of EtOAc/hexane) to give 3.24 g of 4-methanesulfonyl-3-methoxy-phenol (100%).

Dissolve 4-methanesulfonyl-3-methoxy-phenol (3.24 g, 19.04 mmol), 2,6-lutidine (4.08 g, 38.08 mmol) and DMAP (230 mg, 1.9 mmol) in CH$_2$Cl$_2$ (190 mL). Cool the solution to −78° C. and then add trifluoromethanesulfonic acid anhydride (Tf$_2$O, 6.44 g, 22.85 mmol), dropwise. Stir the reaction mixture for 6 hours. Add water (200 mL) and extract the aqueous layer with EtOAc (3×200 mL). Combine the organic layers and dry with Na$_2$SO$_4$, filter, concentrate and purify by flash column chromatography (silica gel, 10-30% of EtOAc/hexane) to give 4.6 g of trifluoro-methanesulfonic acid 4-methanesulfonyl-3-methoxy-phenyl ester (72%).

Dissolve trifluoro-methanesulfonic acid 4-methanesulfonyl-3-methoxy-phenyl ester (3 g, 9 mmol) in toluene (180 mL) and add hexamethylditin (14.7 g, 44.9 mmol) and Pd(PPh$_3$)$_4$ (1.04 g, 0.9 mmol). Heat the reaction mixture to 120° C. with stirring for 4 hours and then cool to room temperature. Add water (250 mL) and extract the aqueous layer with EtOAc (3×250 mL). Combine the organic layers and dry with Na$_2$SO$_4$, filter, concentrate and purify by flash column chromatography (silica gel, 5-40% of EtOAc in hexane) to give 1.9 g of the title compound (61%).

EXAMPLE 26

1-(2-{4-[2-(4-Methanesulfonyl-3-methoxy-phenyl)-6-methoxy-naphthalen-1-yloxy]-phenoxy}-ethyl)-piperidine

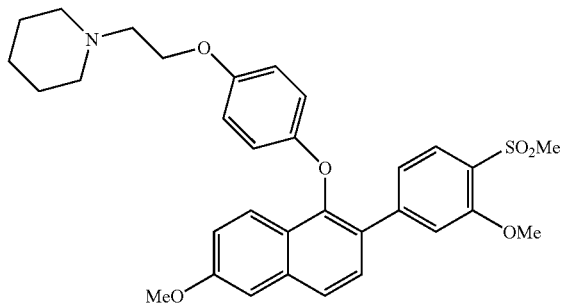

Add (4-methanesulfonyl-3-methoxy-phenyl)-trimethylstannane (300 mg, 0.86 mmol, 1.5 eq.) and the compound of Preparation 1 (300 mg, 0.57 mmol) to a suspension of cesium fluoride (2.9 eq.) in acetonitrile (40 mL). Combine palladium (II) acetate (0.2 eq.) and tricyclohexylphosphine (0.3 eq.) in acetonitrile (15 mL) and sonicate for 10 minutes before adding to the above mixture. Heat the reaction mixture to 90° C. for 18 hours. Concentrate in vacuo and partition residue between ethyl acetate (50 mL) and saturated aqueous NaHCO$_3$ (50 mL). Wash the organic layer with saturated aqueous NH$_4$Cl (50 mL) and brine (50 mL). Dry with Na$_2$SO$_4$, filter, and concentrate in vacuo. Chromatograph the residue on a SiO$_2$ column eluting with methanol in dichloromethane to give 180 mg of the title compound (56%): mass spectrum (ion spray): m/z=562.4 (M+H).

EXAMPLE 27

6-(3-Hydroxy-4-methanesulfonyl-phenyl)-5-[4-(2-piperidin-1-yl-ethoxy)-phenoxy]-naphthalen-2-ol Trifluoroacetate Demethylate 1-(2-{4-[2-(4-methanesulfonyl-3-methoxy-phenyl)-6-methoxy-naphthalen-1-yloxy]-phenoxy}-ethyl)-piperidine (240 mg, 0.43 mmol) with BBr$_3$ in a procedure similar to that used in Example 23 to give 220 mg of crude product as a white solid (95%). Purify the impure product by preparative HPLC (Gilson) to give 120 mg of the title compound (46%): mass spectrum (ion spray): m/z=534.3 (M+H-TFA).

Preparation 9

4-Bromo-2-chloro-1-methanesulfonyl-benzene

Combine 2-chloromethyl-benzenethiol (10 mL, 88 mmol), potassium carbonate (25 g, 180 mmol), iodomethane (11 mL, 177 mmol) and DMF (100 mL). Stir for 12 hours. Filter the suspension through a pad of silica gel and elute with ethyl acetate (500 mL). Evaporate half of the solvent and wash the remaining solution with 10% aqueous LiCl (100 mL). Dry with MgSO$_4$ and evaporate the solvent. Chromatograph the residue on a SiO$_2$ column eluting with hexane to give 13 g of 1-chloro-2-methylsulfanyl-benzene (93%).

Combine 1-methylsulfanyl-2-chloromethyl-benzene (3.7 g, 23 mmol), iron (~130 mg, 2.3 mmol), bromine (1.2 mL, 238 mmol), and dichloromethane (150 mL). Stir for 2 hours. Add water (10 mL), aqueous saturated sodium thiosulfate (100 mL) and ethyl acetate (100 mL). Separate the organic layer and wash with brine, dry with MgSO$_4$, filter and concentrate in vacuo. Chromatograph the residue on a SiO$_2$ column eluting with hexane to give 4.8 g of 4-bromo-2-chloro-1-methylsulfanyl-benzene (87%).

Dissolve 4-bromo-2-chloro-1-methylsulfanyl-benzene (4.8 g, 20 mmol) and mCPBA (20 g, 80 mmol) in dichloromethane (100 mL). Stir for 2 hours. Dilute with dichloromethane (300 mL) and water (100 mL). Separate the organic layer and wash with aqueous saturated NaHCO$_3$ (2×100 mL) and brine (100 mL). Dry with MgSO$_4$, filter and concentrate in vacuo. Wash the solid with ether (2×14011) and dichloromethane (10 mL) to give 1.7 g of the title compound (31%).

EXAMPLE 28

1-(2-{4-[2-(3-Chloro-4-methanesulfonyl-phenyl)-6-methoxy-naphthalen-1-yloxy]-phenoxy}-ethyl)-piperidine

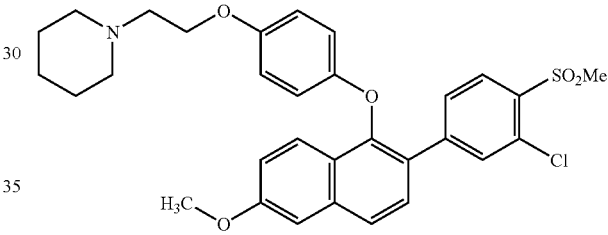

Combine palladium (I) acetate (32 mg, 0.14 mmol), tricyclohexylphosphine (67 mg, 0.24 mmol), cesium fluoride (1.3 g, 8.6 mmol) and acetonitrile (20 mL). Stir for 5 minutes and add the compound of Preparation 1 (500 mg, 0.95 mmol) and bis(neopentylglycolato)diboron (322 mg, 1.42 mmol). Heat to 90° C. and add 4-bromo-2-chloro-1-methanesulfonyl-benzene in acetonitrile (2 mL). Stir at 90° C. for 10 minutes. Cool to room temperature and dilute the solution with ethyl acetate (20 mL) and wash with saturated aqueous NaHCO$_3$ (10 mL). Separate the layers, wash the organic layer with brine (10 mL), dry with MgSO$_4$, filter, and concentrate in vacuo. Chromatograph the residue on a SiO$_2$ column eluting with methanol in dichloromethane (0 to 5%) to give 180 mg of the title compound (33%): mass spectrum (ion spray): m/z=566.2 (M+H).

EXAMPLE 29

6-(3-Chloro-4-methanesulfonyl-phenyl)-5-[4-(2-piperidin-1-yl-ethoxy)-phenoxy]-naphthalen-2-ol Dissolve the product of Example 28 in ethyl acetate (10 mL) and diethyl ether (5 mL). Add 2M HCl in diethyl ether (0.6 mL, 1.2 mmol). Concentrate the slurry and dry in vacuo. Dilute the residue in dichloromethane (5.0 mL) and blanket with nitrogen. Cool the solution to 0° C. with external ice bath. Add BBr$_3$ (0.1 mL, 1.1 mmol). After 1 hour, add water (1.0 mL) and dichloromethane (10 mL). Separate the layers, wash the organic layer with saturated aqueous NaHCO$_3$ (10 mL), brine (10 mL), dry with MgSO$_4$, filter, and concentrate in vacuo. Chromatograph the residue on a SiO$_2$ column eluting with a step gradient of methanol/dichloromethane (0 to 5%) to give 120 mg of the title compound (68%): mass spectrum (ion spray): m/z=552.2 (M+H).

EXAMPLE 30

6-(3-Chloro-4-methanesulfonyl-phenyl)-5-[4-(2-piperidin-1-yl-ethoxy)-phenoxy]-naphthalen-2-ol Hydrochloride Dissolve the product of Example 29 in diethyl ether (5.0 mL), ethyl acetate (6.0 mL) and methanol (1.0 mL) and add 2M HCl in diethyl ether (0.6 mL, 1.2 mmol). Collect the precipitate on filter paper, rinse with diethyl ether and dry in vacuo (<2 mm of Hg) at 20° C. for 4 hours to give 16 mg of the title compound (26%): mass spectrum (ion spray): m/z=552.3 (M+H—HCl).

Preparation 10

4-Bromo-1-methanesulfonyl-2-trifluoromethyl-benzene

Dissolve 2-trifluoromethyl-benzenethiol (10 g; 56 mmol), potassium carbonate (25 g, 180 mmol), iodomethane (11 mL, 177 mmol) in DMF (100 mL). Stir for 12 hours. Filter the suspension through a pad of silica gel and elute with ethyl acetate (500 ne). Evaporate half of the solvent and wash the remaining solution with 10% aqueous LiCl (100 mL). Dry with MgSO$_4$ and evaporate solvent. Chromatograph the residue on a SiO$_2$ column eluting with hexane to give 9.5 g of 1-methylsulfanyl-2-trifluoromethyl-benzene (88%).

Combine 1-methylsulfanyl-2-trifluoromethyl-benzene (3.5 g, 18 mmol), iron (100 mg, 1.79 mmol), bromine (0.95 mL, 18 mmol), aluminum chloride (242 mg, 1.8 mmol) and dichloromethane (50 mL) and stir for 2 hours. Add water (10 mL), aqueous saturated sodium thiosulfate (100 mL) and ethyl acetate (100 mL). Separate the organic layer and wash with brine, dry with MgSO$_4$, filter and concentrate in vacuo. Chromatograph the residue on a SiO$_2$ column eluting with hexane to give 3.6 g of 4-bromo-1-methylsulfanyl-2-trifluoromethyl-benzene (83%).

Combine 4-bromo-1-methylsulfanyl-2-trifluoromethyl-benzene (3.6 g, 15 mmol), mCPBA (7.7 g, 30 mmol) and dichloromethane (100 mL). Stir for 2 hours. Dilute with dichloromethane (300 mL) and water (100 mL). Separate the organic layer and wash with aqueous, saturated NaHCO$_3$ (2×100 mL) and brine (100 mL). Dry with MgSO$_4$, filter and concentrate in vacuo. Wash the solid with diethyl ether (2×10 mL) and dichloromethane (10 mL) to give 2.06 g of the title compound (44%).

EXAMPLE 31

1-(2-{4-[2-(4-Methanesulfonyl-3-trifluoromethyl-phenyl)-1-(4-methoxy-phenyl)-propenyloxy]-phenoxy}-ethyl)-piperidine

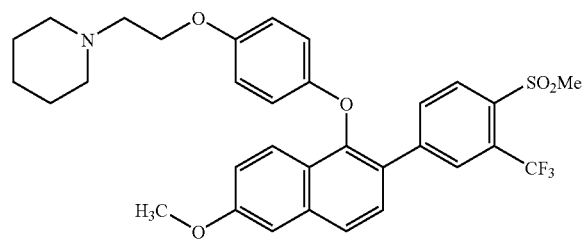

Combine palladium (II) acetate (6 mg, 0.029 mmol), tricyclohexylphosphine (13 mg, 0.047 mmol), cesium fluoride (258 mg, 1.7 mmol) and acetonitrile (1.0 mt). Stir for 5 minutes. Add the compound of Preparation 1 (92 mg, 0.18 mmol) and bis(neopentylglycolato)diboron (64 mg, 0.89 mmol) and heat to 90° C. Add 4-b0romo-1-methanesulfonyl-2-trifluoromethyl-benzene in acetonitrile (1 mL) and stir at 90° C., for 10 minutes. Cool to room temperature and dilute the solution with ethyl acetate (20 mL) and wash with saturated aqueous NaHCO$_3$ (10 mL). Separate the layers, wash the organic layer with brine (10 mL), dry with MgSO$_4$, filter, and concentrate in vacuo. Chromatograph the residue on a SiO$_2$ column eluting with methanol in dichloromethane (0 to 5%) to give 62 mg of the title compound (54%): mass spectrum (ion spray): m/z=600.3 (M+H).

EXAMPLE 32

6-(4-Methanesulfonyl-3-trifluoromethyl-phenyl)-5-[4-(2-piperidin-1-yl-ethoxy)-phenoxy]-naphthalen-2-ol Hydrochloride Dissolve the product of Example 31 in ethyl acetate (10 mL) and diethyl ether (5 mL). Add 2M HCl in diethyl ether (0.1 mL, 0.2 mmol). Concentrate the slurry and dry in vacuo. Dilute the residue in dichloromethane (5.0 mL) and blanket with nitrogen. Cool the solution to 0° C. with external ice bath. Add BBr$_3$ (0.1 mL, 1.1 mmol) and stir for 1 hour. Dilute with water (1.0 mL) and dichloromethane (10 mL). Separate the layers and wash the organic layer with saturated aqueous NaHCO$_3$ (10 mL) and brine (10 mL). Dry with MgSO$_4$, filter, and concentrate in vacuo. Chromatograph the residue on a SiO$_2$ column eluting the 6-(4-methanesulfonyl-3-trifluoromethyl-phenyl)-5-[4-(2-piperidin-1-yl-ethoxy)-phenoxy]-naphthalen-2-ol with a step gradient of methanol/dichloromethane (O to 5%). Dissolve the free base in diethyl ether (5.0 mL), ethyl acetate (6.0 mL) and methanol (1.0 mL) and, add 2M HCl in diethyl ether (0.1 mL, 0.2 mmol). Collect the precipitate on filter paper, rinse with diethyl ether and dry in vacuo (<2 mm of Hg) at 65° C., for 48 hours to give 34 mg of the title compound (53%).

Preparation 11

1-Bromo-2,3-dichloro-4-methanesulfonyl-benzene

Combine 4-bromo-2-chloro-1-methylsulfanyl-benzene (1.9 g, 20 mmol) and mCPBA (5.0 g, 80 mmol) in dichloromethane (30 mL). Stir for 2 hours. Dilute with dichloromethane (20 mL) and water (20 mL). Separate the organic layer and wash with aqueous saturated NaHCO$_3$ (2×100 mL) and brine (100 mL). Dry with MgSO$_4$, filter and concentrate in vacuo. Wash the solid with diethyl ether (2×10 mL) and dichloromethane (10 mL) to give 890 mg of the title compound (52%).

EXAMPLE 33

1-(2-{4-[2-(2,3-Dichloro-4-methanesulfonyl-phenyl)-6-methoxy-naphthalen-1-yloxy]-phenoxy}-ethyl)-piperidine

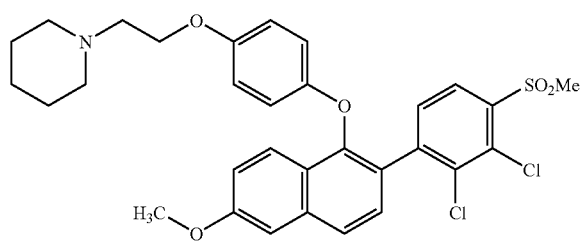

Combine palladium (II) acetate (32 mg, 0.14 mmol), tricyclohexylphosphine (67 mg, 0.24 mmol), cesium fluoride (1.3 g, 8.6 mmol) and acetonitrile (20 mL). Stir for 5 minutes. Add the compound of Preparation 1 (500 mg, 0.95 mmol) and bis(neopentylglycolato)diboron (322 mg, 1.42 mmol). Heat to 90° C. and add 1-bromo-2,3-dichloro-4-methanesulfonyl-benzene in acetonitrile (2 mL). Stir at 90° C. for 10 minutes. Cool to room temperature and dilute the solution with ethyl acetate (20 mL) and wash with saturated aqueous NaHCO$_3$ (10 mL). Separate the layers, wash the organic layer with brine (10 mL), dry with MgSO$_4$, filter, and concentrate in vacuo. Chromatograph the residue on a column eluting with methanol in dichloromethane (0 to 5%) to give 180 mg of the title compound (33%): mass spectrum (ion spray): m/z=566.2.

EXAMPLE 34

6-(2,3-Dichloro-4-methanesulfonyl-phenyl)-5-[4-(2-piperidin-1-yl-ethoxy)-phenoxy]-naphthalen-2-ol Hydrochloride Dissolve the product of Example 33 in ethyl acetate (10 mL) and diethyl ether (5 mL). Add 2M HCl in diethyl ether (0.5 mL, 1.0 mmol). Concentrate the slurry and dry in vacuo. Dilute the residue in dichloromethane (5.0 mL) and blanket with nitrogen. Cool the solution to 0° C. with external ice bath. Add BBr$_3$ (0.1 mL, 1.1 mmol) and stir for 1 hour. Quench with water (1.0 mL) and and dilute with dichloromethane (10 mL). Separate the layers, wash the organic layer with saturated aqueous NaHCO$_3$ (10 mL) and brine (10 mL). Dry with MgSO$_4$, filter, and concentrate in vacuo. Chromatograph the residue on a SiO$_2$ column eluting the 6-(2,3-dichloro-4-methanesulfonyl-phenyl)-5-[4-(2-piperidin-1-yl-ethoxy)-phenoxy]-naphthalen-2-ol with a step gradient of methanol/dichloromethane (0 to 5%). Dissolve the free base in diethyl-ether (5.0 mL), ethyl acetate (6.0 mL) and methanol (1.0 mL) and add 2M HCl in diethyl ether (0.5 mL, 1.0 mmol). Collect the precipitate on filter paper, rinse with diethyl ether to give 38 mg of the title compound (30%): mass spectrum (ion spray): m/z=586.2.

Preparation 12

4-Bromo-1,2-bis-methanesulfonyl-benzene

Combine 4-bromo-2-fluoro-1-methylsulfanyl-benzene (4.8 g, 22 mmol) and sodium methanethiolate (1.6 g, 22 mmol) in DMF (50 mL). Stir for 48 hours. Pour the reaction mixture into ice (10 g). Separate the layers and wash the organic layer with aqueous saturated NaHCO$_3$ and brine. Dry with MgSO$_4$, filter and concentrate in vacuo. Chromatograph the residue on a column eluting with diethyl ether in hexane (0 to 5%) to give 4.82 g of 4-bromo-1,2-bis-methylsulfanylbenzene (89%).

Combine 4-bromo-1,2-bis-methylsulfanylbenzene (1.4 g, 5.5 mmol) and mCPBA (8.6 g, 34 mmol) in dichloromethane (100 mL). Stir for 2 hours. Add dichloromethane (300 mL) and water (100 mL). Separate the organic layer and wash with aqueous saturated NaHCO$_3$ (2×100 mL) and brine (100 mL). Dry with MgSO$_4$, filter and concentrate in vacuo. Wash the solid with ether (2×10 mL) and dichloromethane (10 mL) to give 800 mg of 4-bromo-1,2-bis-methanesulfonylbenzene (46%).

EXAMPLE 35

1-(2-{4-[2-(3,4-Bis-methanesulfonyl-phenyl)-6-methoxy-naphthalen-1-yloxy]-phenoxy}-ethyl)-piperidine

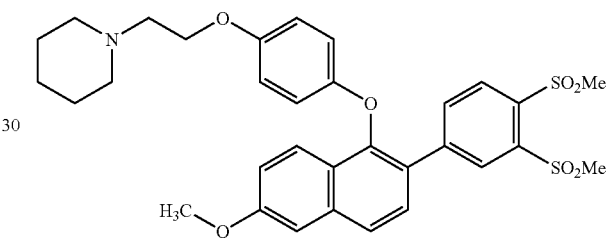

Combine palladium (II) acetate (13 mg, 0.058 mmol), tricyclohexylphosphine (27 mg, 0.096 mmol), cesium fluoride (518 mg, 3.4 mmol) and acetonitrile (20 mL). Stir for 5 minutes and add the compound of Preparation 1 (200 mg, 0.38 mmol) and bis(neopentylglycolato)diboron (130 mg, 0.58 mmol). Heat to 90° C., add 4-bromo-1,2-bis-methanesulfonyl-benzene in acetonitrile (2 mL), and stir for 10 minutes. Cool to room temperature and dilute the solution with ethyl acetate (20 mL) and wash with saturated aqueous NaHCO$_3$ (10 mL). Separate the layers, wash the organic layer with brine (10 mL), dry with MgSO$_4$, filter, and concentrate in vacuo. Chromatograph the residue on a column eluting with methanol in dichloromethane (0 to 5%) to give 130 mg of the title compound (56%).

EXAMPLE 36

6-(3,4-Bis-methanesulfonyl-phenyl)-5-[4-(2-piperidin-1-yl-ethoxy)-phenoxy]-naphthalen-2-ol Hydrochloride Dissolve the product of Example 35 in ethyl acetate (10 mL) and diethyl ether (5 mL). Add 2M HCl in diethyl ether (0.1 mL, 0.2 mmol). Concentrate the slurry and dry in vacuo. Dilute the residue in dichloromethane (5.0 mL) and blanket with nitrogen. Cool the solution to 0° C. with an external ice bath. Add BBr$_3$ (0.1 mL, 1.1 mmol) and stir for 1 hour. Quench with water (1.0 mL) and dilute with dichloromethane (10 mL). Separate the layers, wash the organic layer with saturated aqueous NaHCO$_3$ (10 mL) and brine (10 mL). Dry with MgSO$_4$, filter, and concentrate in vacuo. Chromatograph the residue on a column eluting the 6-(3,4-bis-methanesulfonyl-phenyl)-5-[4-(2-piperidin-1-yl-ethoxy)-phenoxy]-naphthalen-2-ol with a step gradient of methanol/dichloromethane (0 to 5%). Dissolve the free base in diethyl ether (5.0 mL), ethyl acetate (6.0 mL) and methanol (1.0 mL) and add 2M HCl in diethyl ether (0.1 mL, 0.2 mmol). Collect the precipitate on filter paper, rinse with diethyl ether and dry in vacuo (<2 mm of Hg) at 65° C. for 48 hours to give 61 mg of the title compound (45%): mass spectrum (ion spray): m/z: 594.9 (M+H—HCl).

Preparation 13

1-Bromo-4-(2,2,2-trifluoro-ethanesulfonyl)-benzene

Dissolve 4-bromo-benzenethiol (1.0 g, 5.3 mmol) in dry dimethylformamide (50 mL) and cool to 0° C. under nitrogen. Add dry sodium hydride (152 mg, 6.4 mmol), portionwise. After the vigorous gas evolution stops, add toluene-4-sulfonic acid 2,2,2-trifluoro-ethyl ester (2.0 g, 8.0 mmol) and stir the reaction overnight at room temperature. Slowly pour the reaction into water (400 mL) and extract with ethyl acetate (2×50 mL). Wash the combined organic layers with water (100 mL) and brine (100 mL). Dry the organic layer with sodium sulfate, filter and concentrate in vacuo. Chromatograph the resultant residue on a SiO$_2$ column with hexanes to yield 640 mg of 1-bromo-4-(2,2,2-trifluoro-ethylsulfanyl)-benzene (45%).

Dissolve 1-bromo-4-(2,2,2-trifluoro-ethylsulfanyl)-benzene (640 mg, 2.4 mmol) in dichloromethane (25 mL) and cool to 0° C.; Add mCPBA (1.8 g, 7.1 mmol, 68%) in portions and stir the reaction for 2 hours at room temperature. Filter the white precipitate and wash the filtrate with 1N aqueous NaOH. Dry the organic layer with sodium sulfate, filter and concentrate in vacuo to yield 700 mg of the title compound (98%).

EXAMPLE 37

1-[2-(4-{6-Methoxy-2-[4-(2,2,2-trifluoro-ethanesulfonyl)-phenyl]-naphthalen-1-yloxy}-phenoxy)-ethyl]-piperidine

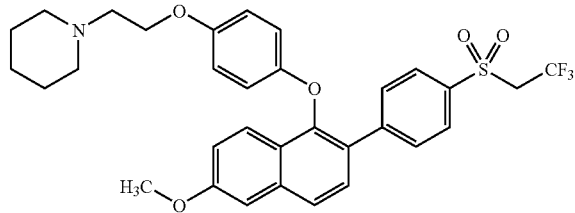

Charge a flame-dried flask with palladium (II) acetate (6.4 mg, 0.029 mmol), tricyclohexylphosphine (13.3 mg, 0.048 mmol) and cesium fluoride (260 mg, 1.71 mmol). Add dry acetonitrile (2 mL) and stir under nitrogen. Add the compound of Preparation 1 (100 mg, 0.19 mmol) followed by bis(neopentylgylcolato)diboron (64 mg, 0.29 mmol). Plunge the reaction into an 80° C. oil bath. Once the reaction turns black (~3 to 5 minutes) immediately add 1-bromo-4-(2,2,2-trifluoro-ethanesulfonyl)-benzene (116 mg, 0.38 mmol) and continue heating. After 45 minutes, cool the reaction to room temperature and filter through celite. Concentrate the filtrate in vacuo and purify on a SiO$_2$ column with methanol in dichloromethane (0 to 3%) to yield 26 mg of the title compound (23%): LRMS (ESI, positive ion) m/z=600.5 (M+H).

EXAMPLE 38

5-[4-(2-Piperidin-1-yl-ethoxy)-phenoxy]-6-[4-(2,2,2-trifluoro-ethanesulfonyl)-phenyl]-naphthalen-2-ol Dissolve the compound of Example 37 (26 mg, 0.043 mmol) in dichloromethane (1 mL) and add 2M HCl in diethyl ether (43 µL, 0.086 mmol). Remove the solvents in vacuo and place on a high vacuum pump for 10 minutes. Dissolve the resultant foam in dry dichloromethane (1 mL) and cool to 0° C. Add BBr$_3$ (20 µL, 0.22 mmol) dropwise and stir at 0° C. for 1 hour. Pour the reaction into cold saturated aqueous sodium bicarbonate (5 mL) and extract with dichloromethane (2×5 mL). Dry the combined organic phases with sodium sulfate, filter, and concentrate in vacuo. Purify the resultant oil on a SiO$_2$ column with methanol in dichloro methane (0 to 8%) to yield 16 mg of the title compound (64%): mass spectrum (ion spray) m/z=586.4 (M+H).

EXAMPLE 39

5-[4-(2-Piperidin-1-yl-ethoxy)-phenoxy]-6-[4-(2,2,2-trifluoro-ethanesulfonyl)-phenyl]-naphthalen-2-ol Hydrochloride Dissolve the compound of Example 38 (30 mg, 0.051 mmol) in dry dichloromethane (1 mL) and add 2M HCl in diethyl ether (0.10 mL, 0.20 mmol). Stir at room temperature for 1 minute. Remove the solvent by blowing nitrogen over the liquid. Place the residue on a high vacuum pump for 1 hour. Dry the product in a vacuum oven at 45° C. overnight to yield 30 mg of the title compound (97%): mass spectrum (ion spray) m/z=586.3 (M+H—HCl).

Preparation 14

2-(4-Isopropylsulfanyl-phenyl)-boronic acid

Dissolve 4-bromo-benzenethiol (1.0 g, 5.3 mmol) in dry dimethylformamide (50 mL) and cool to 0° C. under nitrogen. Add dry sodium hydride (153 mg, 6.4 mmol) in portions. After the vigorous gas evolution stops, add 2-bromo-propane (0.60 mL, 6.4 mmol) and stir the reaction overnight at room temperature. Slowly pour the reaction into water (300 mL) and extract with ethyl acetate (2×150 mL). Wash the combined organic layers with water (100 mL) and brine (100 mL). Dry the organic layer with sodium sulfate, filter and concentrate in vacuo. Chromatograph the resultant residue on a SiO$_2$ column with 5% ethyl acetate in hexanes to yield 1.1 g of 1-bromo-4-isopropylsulfanyl-benzene (92%).

Dissolve 1-bromo-4-isopropylsulfanyl-benzene (2.5 g, 10.8 mmol) in dry tetrahydrofuran (100 mL) and cool the solution to −78° C. Add 2.5 M n-butyllithium in hexanes (5.2 mL, 12.9 mmol) dropwise and allow the reaction to warm to −40° C. and stir for 30 minutes. Cool the reaction to −78° C. and add triisopropyl borate (7.4 mL, 32.4 mmol) and allow the reaction to slowly warm to room temperature. Add 10% aqueous potassium hydroxide (96 mL, 172 mmol) and stir overnight. Slowly pour the reaction into a mixture of concentrated HCl and ice. Extract the aqueous solution with dichloromethane, dry with sodium sulfate and concentrate in vacuo to yield 1.9 g. of the title compound (90%).

EXAMPLE 40

1-(2-{4-[2-(4-Isopropylsulfanyl-phenyl)-6-methoxy-naphthalen-1-yloxy]-phenoxy}-ethyl)-piperidine

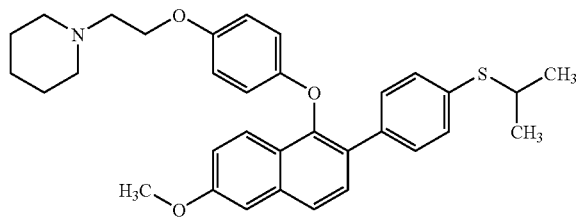

Combine 2-(4-isopropylsulfanyl-phenyl)-boronic acid (223 mg, 1.14 mmol), the compound of Preparation 1 (300 mg, 0.57 mmol) and cesium fluoride (433 mg, 2.85 mmol) in a flame-dried flask fitted with a reflux condenser and purge with nitrogen. In a separate dried flask combine palladium (II) acetate (13 mg, 0.06 mmol) and tricyclohexylphosphine (24 mg, 0.09 mmol). Add dry acetonitrile (5 mL) and sonicate for 10 minutes under nitrogen. Add the catalyst slurry to the solids and plunge the flask into a 90° C. oil bath. After 20 minutes cool the black suspension to room temperature and filter through celite, rinsing with dichloromethane. Concentrate the filtrate in vacuo. Chromatograph the resultant residue on a $SiO_2$ column with 3% methanol in dichloromethane with 0.2% ammonium hydroxide to give 300 mg of the title compound (95%): mass spectrum (ion spray) m/z=528.3 (M+H).

EXAMPLE 41

6-(4-Isopropylsulfanyl-phenyl)-5-[4-(2-piperidin-1-yl-ethoxy)-phenoxy]-naphthalen-2-ol Dissolve the compound of Example 43 (300 mg, 0.57 mmol) in dichloromethane (3 mL). Add 2M HCl in diethyl ether (0.51 mL, 1.14 mmol) and stir for 1 minute. Remove the solvent in vacuo and place on a high vacuum pump for 20 minutes. Dissolve the foam in dry dichloromethane (6 mL) and cool to 0° C. Add $BBr_3$ (0.21 mL, 2.3 mmol), dropwise. Stir for 45 minutes and quench by adding methanol (1 mL). Slowly pour the reaction mixture into saturated aqueous sodium bicarbonate (10 mL) and extract with dichloromethane (2×10 mL). Dry the combined organic layers with sodium sulfate and concentrate in vacuo. Chromatograph the residue on a $SiO_2$ column with 5% methanol in dichloromethane with 0.2% ammonium hydroxide to yield 236 mg of the title compound (81%): mass spectrum (ion spray) m/z=514.3 (M+H).

EXAMPLE 42

5-[4-(2-Piperidin-1-yl-ethoxy)-phenoxy]-6-[4-(propane-2-sulfonyl)-phenyl]-naphthalen-2-ol Dissolve the compound of Example 41 (236 mg, 0.46 mmol) in glacial acetic acid (5 mL) and add sodium perborate (92 mg, 0.92 mmol). Stir the reaction overnight and pour the mixture into saturated aqueous sodium bisulfite (20 mL). Extract with dichloromethane (2×20 mL) and wash the combined organic layers with saturated aqueous sodium bicarbonate (10 mL). Dry the organic layer with sodium sulfate, filter and concentrate in vacuo. Chromatograph the residue on a $SiO_2$ column with 4% methanol in dichloromethane with 0.2% ammonium hydroxide to yield 197 mg of the title compound (79%): mass spectrum (ion spray) m/z=546.3 (M+H).

EXAMPLE 43

5-[4-(2-Piperidin-1-yl-ethoxy)-phenoxy]-6-[4-(propane-2-sulfonyl)-phenyl]-naphthalen-2-ol Hydrochloride Dissolve the compound of Example 42 (123 mg, 0.36 mmol) in dry dichloromethane (0.5 mL). Dilute the solution with diethyl ether (4 mL) and add 2M HCl in diethyl ether (0.36 mL, 0.72 mmol). Stir at room temperature for 10 minutes. Filter the white precipitate through paper and dry the solids in a vacuum oven at 50° C. overnight to yield 102 mg of the title compound (78%): mass spectrum (ion spray) m/z=546.3 (M+H—HCl).

Preparation 15

2-Methyl-4-methylthiophenylboronic acid

Add 1M 3'-methyl-phenylmagnesium bromide in THF (25 mL, 25 mmol) to −30° C. diethyl ether (50 mL). Add dimethyl disulfide (1.8 mL, 20 mmol) to the reaction over 3 minutes allowing the reaction to warm to room temperature. Dilute the reaction in $H_2O$ (75 mL) and diethyl ether (50 mL). Separate and extract the cloudy aqueous layer with diethyl ether (25 mL). Combine the organic layers and wash with $H_2O$ (25 mL). Dry the organic layer with $Na_2SO_4$ (30 g), filter over Celite 501 (10 g) and concentrate in vacuo to give 3.0 g of crude material. Combine with another batch of crude title compound that yielded 6.0 g crude. Chromatograph the entire 9.0 g crude on a $SiO_2$ column in hexanes to give 7.2 g (70%) of 1-methyl-3-methylsulfanyl-benzene.

Combine iron (25 mg, 0.45 mmol) and 1-methyl-3-methylsulfanyl-benzene (204 mg, 1.47 mmol) in dichloromethane (DCM, 2 mL). Cool the slurry to 3° C. and add $Br_2$ (74 μL, 1.44 mmol) over 5 minutes. Stir at 3° C. for 10 minutes and remove the external cooling bath. Stir at room temperature for 4 hours, then quench with 10% aqueous $Na_2S_2O_3$ solution. Dilute the reaction with dichloromethane (10 mL) and separate. Wash the organic layer with brine, concentrate and chromatograph with dichloromethane in hexanes (0 to 5%) to give 125 mg of 1-bromo-2-methyl-4-methylsulfanyl-benzene (53%).

Add 1-bromo-2-methyl-4-methylsulfanyl-benzene (608 mg, 2.80 mmol) to diethyl ether (60 mL) and cool to −78° C. under a nitrogen blanket. Add t-BuLi (3.4 mL, 5.78 mmol) over a 15 minute period, stir for 2 minutes, add trimethyl borate (($MeO)_3B$, 340 μL, 2.99 mmol) over 2 minutes, stir for 15 minutes at −78° C. and then let warm to room temperature. Quench the reaction with saturated aqueous $NH_4Cl$ (7 mL), stir for 15 minutes, add 1M aqueous HCl (6 mL), stir for another 2 minutes and separate. Dry with $Na_2SO_4$, filter (wash the drying agent with ethyl acetate (3×20 mL)), and concentrate. Chromatograph the crude material on a $SiO_2$ column with 20% ethyl acetate in hexanes to 5% methanol in ethyl acetate to give 267 mg of the title compound (52%).

EXAMPLE 44

1-(2-{4-[6-Methoxy-2-(2-methyl-4-methylsulfanyl-phenyl)-naphthalen-1-yloxy]-phenoxy}-ethyl)-piperidine Hydrochloride

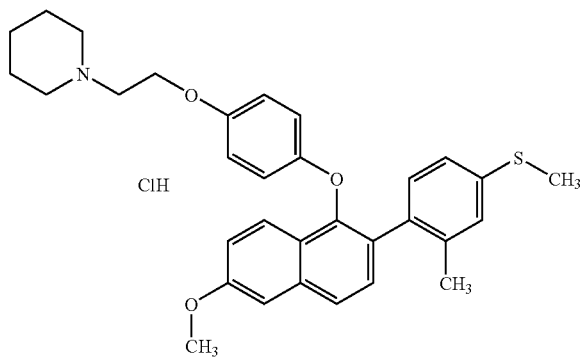

Add the compound of Preparation 1 (300 mg, 0.57 mmol), 2-methyl-4-methylthiophenylboronic acid (267 mg, 1.47 mmol) and cesium fluoride (672 mg, 4.42 mmol) into acetonitrile (3.0 mL) in a flame-dried flask fitted with a reflux condenser. In a separate dried flask combine palladium (II) acetate (14.5 mg, 0.06 mmol) and tricyclohexylphosphine (27.5 mg, 0.10 mmol). Add dry acetonitrile (2.5 mL) and sonicate for 10 minutes under nitrogen. Add the catalyst suspension to the reaction slurry and plunge the flask into a 90° C. oil bath. After 40 minutes, cool the black suspension to room temperature, filter and wash the solids with acetonitrile (3×10 mL). Concentrate the filtrate in vacuo. Partition the residue between ethyl acetate (25 mL) and 5% aqueous sodium carbonate (10 mL). Separate the layers and wash the organic layer with saturated aqueous $NH_4Cl$ (10 mL) and brine (10 mL). Concentrate the organic layer in vacuo and chromatograph the residue on a $SiO_2$ column with methanol in dichloromethane (−0 to 2.5%) to give 331 mg of 1-(2-{4-[6-methoxy-2-(2-methyl-4-methylsulfanyl-phenyl)-naphthalen-1-yloxy]-phenoxy}-ethyl)-piperidine (94%). Dissolve the free base material in ethyl acetate (10' mL), add 2M HCl in diethyl ether (350 µL) and concentrate in vacuo to give the title compound: mass spectrum (ion spray) m/z=514.3 (M+H).

EXAMPLE 45

6-(2-Methyl-4-methylsulfanyl-phenyl)-5-[4-(2-piperidin-1-yl-ethoxy)-phenoxy]-naphthalen-2-ol Dissolve 1-(2-{4-[6-methoxy-2-(2-methyl-4-methylsulfanyl-phenyl)-naphthalen 1-yloxy]-phenoxy}-ethyl)-piperidine hydrochloride (331 mg, 0.603 mmol) in dichloromethane (15 mL) and cool to 5° C. Add $BBr_3$ (285 µL, 3.02 mmol) to the light suspension over 5 minutes. Quench the reaction after 1 hour with saturated aqueous $NaHCO_3$ (15 mL). Separate the layers and extract the aqueous layer with dichloromethane (2×10 mL). Pour the solution onto a $SiO_2$ plug (20 g) and elute with methanol in dichloromethane (5 to 15%). Concentrate the fractions in vacuo to give 301 mg of the title compound (100%): mass spectrum (ion spray) m/z=500.3 (M+H).

EXAMPLE 46

6-(4-Methanesulfonyl-2-methyl-phenyl)-5-[4-(2-piperidin-1-yl-ethoxy)-phenoxy]-naphthalen-2-ol Trifluoroacetate Dissolve the compound of Example 45 (301 mg, 0.060 mmol) in glacial acetic acid (5 mL) and add $NaBO_3.H_2O$ (120 mg, 1.20 mmol). Concentrate the reaction after 14 hours and partition between 10% aqueous $NaHSO_3$ (30 mL), MeOH (3 mL) and dichloromethane (50 mL). Separate the layers and extract the aqueous layer with dichloromethane (10 mL). Combine the organic layers and wash with saturated aqueous $NaHCO_3$ (10 mL) and $H_2O$ (10 mL). Dry with $Na_2SO_4$, filter, and concentrate in vacuo. Chromatograph on a $SiO_2$ column with methanol in dichloromethane (0 to 10%) to obtain impure product. This crude material is purified by preparative HPLC to give 97 mg of the title compound (23%): mass spectrum (ion spray) m/z=532.3 (M+H-TFA).

EXAMPLE 47

1-(2-{4-[6-Methoxy-2-(3-methyl-4-methylsulfanyl-phenyl)-naphthalen-1-yloxy]-phenoxy}-ethyl)-piperidine

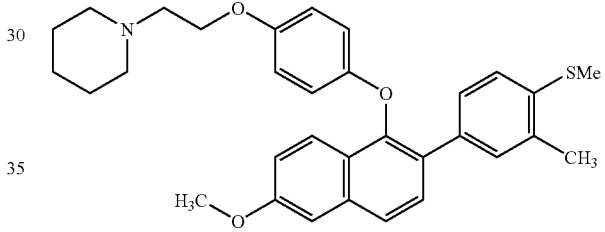

Combine palladium (II) acetate (21 mg, 0.094 mmol), tricyclohexylphosphine (53 mg, 0.19 mmol), the compound of Preparation 1 (500 mg, 0.95 mmol), cesium fluoride (1.00 g, 6.62 mmol) 3-methyl-4-(methylthio)benzene boronic acid (U.S. Pat. No. 6,307,047; 520 mg, 2.86 mmol) and acetonitrile (40 mL). Heat to 90° C. for 1 hour. Cool to room temperature and dilute the solution with ethyl acetate (20 mL) and wash with saturated aqueous $NaHCO_3$ (10 mL). Separate the layers, wash the organic layer with brine (10 mL), dry with $MgSO_4$, filter, and concentrate in vacuo. Chromatograph the residue on a $SiO_2$ column eluting the material with methanol in dichloromethane (2 to 4%) to give 371 mg of the title compound (75%): mass spectrum (ion spray): m/z=514.3 (M+H).

EXAMPLE 48

6-(3-Methyl-4-methylsulfanyl-phenyl)-5-[4-(2-piperidin-1-yl-ethoxy)-phenoxy]-naphthalen-2-ol Dissolve the product of Example 47 in ethyl acetate (10 mL) and diethyl ether (5 mL). Add 2M HCl in diethyl ether (5 mL, 10.0 mmol). Concentrate the slurry and dry in vacuo. Dilute the residue in dichloromethane (5.0 mL) and blanket with nitrogen. Cool the solution to 0° C. with external ice bath and add $BBr_3$ (0.3 mL, 3.2 mmol). After 1 hour, add water (1.0 mL) and ethyl acetate (10 mL). Separate the layers, wash the organic layer with saturated aqueous $NaHCO_3$ (10 mL) and brine (10 mL). Dry with MgSO₄, filter, and concentrate in vacuo. Chromatograph the residue on a column eluting the material with a step gradient of methanol in dichloromethane (0 to 0.5%) to give 330 mg of the title compound (92%): mass spectrum (ion spray): m/z=500.3 (M+H).

EXAMPLE 49

6-(4-Methanesulfonyl-3-methyl-phenyl)-5-[4-(2-piperidin-1-yl-ethoxy)-phenoxy]-naphthalen-2-ol Hydrochloride Combine the compound of Example 48 and sodium perborate (162 mg, 1.62 mmol) in acetic acid (4 mL). After 2 days, add dichloromethane (20 mL) and water (5 mL). Separate the layers, wash the organic layer with saturated aqueous NaHCO₃ (10 mL), brine (10 mL), dry with MgSO₄, filter, and concentrate in vacuo. Chromatograph the residue on a SiO₂ column eluting the 6-(4-methanesulfonyl-3-methyl-phenyl)-5-[4-(2-piperidin-1-yl-ethoxy)-phenoxy]-naphthalen-2-ol with a step gradient of methanol in dichloromethane (0 to 5%). Dissolve the free base in diethyl ether (5.0 mL), ethyl acetate (6.0 mL) and methanol (1.0 mL) and add 2M HCl in diethyl ether (1 mL, 2.0 mmol). Collect the precipitate on filter paper, rinse with diethyl ether and dry in vacuo (<2 mm of Hg) at 65° C. for 48 hours to give 40 mg of the title compound (11%): mass spectrum (ion spray): m/z=537.0 (M+H—HCl).

Preparation 16

2-Benzo[b]thiophen-5-yl-4,4,5,5-tetramethyl-[1,3,2]dioxaborolane

Dissolve 5-bromo-benzo[b]thiophene (*J. Mater. Chem.*, 10:2069-2081, 2000; 49 g, 7.0 mmol) in DMSO (40 mL). Add bis(pinacolato)diboron (7 mmol), PdCl₂(dppf).CH₂Cl₂ (0.33 mmol), and KOAc (20 mmol). Flush the flask with N₂, and then heat the reaction mixture to 80° C. with stirring. Continue to heat the reaction mixture for 3 hours, and then cool to room temperature. Add water (66 mL) and extract the aqueous layer with EtOAc (3×66 mL). Combine the organic layers and dry with Na₂SO₄, filter, concentrate and purify by flash column chromatography (silica gel, 0-5% Et₂O/pentane) to give 1.56 g of the title compound (86%).

EXAMPLE 50

1-{2-[4-(2-Benzo[b]thiophen-5-yl-6-methoxy-naphthalen-1-yloxy)-phenoxy]-ethyl}-piperidine

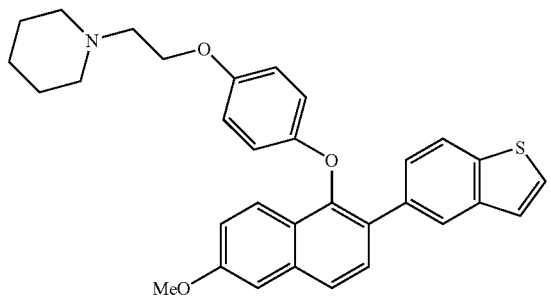

Dissolve 2-benzo[b]thiophen-5-yl-4,4,5,5-tetramethyl-[1,3,2]dioxaborolane (400 mg, 1.54 mmol) and the compound of Preparation 1 (270 g, 0.51 mmol) in CH₃CN (24 mL). Add Pd(OAc)₂ (0.05 mmol), tricyclohexylphosphine (0.075 mmol), and CsF (4.5 mmol). Flush the flask with N₂, then heat the reaction mixture to 90° C. with stirring. Continue to heat the reaction mixture for 6 hours, and then cool to room temperature. Add water (50 mL), and extract the aqueous layer with CH₂Cl₂ (3×25 mL). Combine the organic layers and dry with Na₂SO₄, filter, concentrate and purify by flash column chromatography (silica gel, 0-4% MeOH—NH₄OH (10/1, v/v) in CH₂Cl₂) to give 240 mg of the title compound (93%): ¹H NMR (CDCl₃) δ 7.99 (d, J=1.2 Hz, 1H), 7.88 (d, J=9.2 Hz, 1H), 7.82 (d, J=8.4 Hz, 1H), 7.72 (d, J=8.4 Hz, 1H), 7.58 (dd, J=8.4, 1-2 Hz, 1H), 7.41 (d, J=5.6 Hz, 1H), 7.31 (d, J=5.6 Hz, 1H), 7.21 (d, J=2.8 Hz, 1H), 7.11 (dd, J=9.2, 2.8 Hz, 1H), 6.73 (d, J=5.6 Hz, 1H), 6.60-6.63 (m, 4H), 4.04 (t, J=5.0 Hz, 2H), 3.94 (s, 3H), 2.93 (t, J=5.0 Hz, 2H), 2.67-2.79 (m, 4H), 1.66-1.75 (m, 4H), 1.44-1.55 (m, 2H).

EXAMPLE 51

6-Benzo[b]thiophen-5-yl-5-[4-(2-piperidin-1-yl-ethoxy)-phenoxy]-naphthalen-2-ol Trifluoroacetate Dissolve the compound of Example 50 (240 mg, 0.48 mmol) in dimethylformamide (DMF, 7 mL), add sodium ethanethiolate (EtSNa, 100 mg, 1.19 mmol). Flush the flask with N₂ and then heat the reaction mixture to 150° C. Continue to heat the reaction mixture for 0.5 hours, cool to room temperature. Add water (15 mL), and extract the aqueous layer with CH₂Cl₂ (3×15 mL). Combine the organic layers and dry with Na₂SO₄, filter, concentrate and purify by flash column chromatography (silica gel, 0-8% MeOH—NH₄OH (10/1, v/v) in CH₂Cl₂) to give 140 mg of crude 6-benzo[b]thiophen-5-yl-5-[4-(2-piperidin-1-yl-ethoxy)-phenoxy]-naphthalen-2-ol. Purify the impure product by preparative HPLC (Gilson) to give 95 mg of the title compound (55%): mass spectrum (ion spray): m/z=496.3 (M+H-TFA).

EXAMPLE 52

Acetic acid 6-(1,1-dioxo-1H-1λ⁶-benzo[b]thiophen-5-yl)-5-[4-(2-piperidin-1-yl-ethoxy)-phenoxy]-naphthalen-2-yl ester Dissolve 6-benzo[b]thiophen 5-yl-5-[4-(2-piperidin-1-yl-ethoxy)-phenoxy]-naphthalen-2-ol (560 mg, 1.13 mmol) in CH₂Cl₂ (20 mL), and cool the solution to 0° C. Add DMAP (28 mmol), triethylamine (Et₃N, 8 mmol) and acetic anhydride (Ac₂O, 1.9 mmol). Stir the reaction mixture for 3 hours at 0° C. and then add water (40 mL). Extract the aqueous layer with CH₂Cl₂ (3×40 mL). Combine the organic layers and dry with Na₂SO₄, filter, concentrate and purify by flash column chromatography (silica gel, 0-5% MeOH in CH₂Cl₂) to give 360 mg of the acylated product (59%): mass spectrum (ion spray): m/z=538.3 (M+H). Dissolve the acylated product (110 mg, 0.2 mmol) in acetic acid (AcOH, 1.1 mL) and add H₂O₂ (110 mg, 1.0 mmol, 30% wt). Heat the reaction mixture to 90° C. for one hour and then cool to room temperature. Add 1M aqueous bisulfite solution (1 mL) and stir the reaction mixture for 10 minutes. Add saturated aqueous NaHCO₃ solution (20 mL) and extract the aqueous layer with CH₂Cl₂ (3×20 mL). Combine the organic layers and dry with Na₂SO₄, filter, concentrate and purify by flash column chromatography (silica gel, 0-5% MeOH in CH₂Cl₂) to give 51 mg of the title compound (44%): mass spectrum (ion spray): m/z=570.3 (M+H).

EXAMPLE 53

6-(1,1-Dioxo-1H-1λ⁶-benzo[b]thiophen-5-yl)-5-[4-(2-piperidin-1-yl-ethoxy)-phenoxy]-naphthalen-2-ol Trifluoroacetate Dissolve the compound of Example 52 (51 mg, 0.089 mmol) in MeOH (2 mL). Add NaHCO$_3$ (0.10 mmol) and stir the reaction mixture for 3 hours at room temperature. Remove the solids by filtration. Concentrate the filtrate and purify the residue by flash column chromatography (silica gel, 2-10% MeOH—NH$_4$OH (10/1, v/v) in CH$_2$Cl$_2$). Dry the pooled materials at 40° C. for overnight in vacuo to give 67 mg of the deprotected product (85%). Dissolve the deprotected product (67 mg, 0.13 mmol) in CH$_2$Cl$_2$ (10 mL) and cool it to −78° C. Add CF$_3$CO$_2$H (0.13 mL, 1.0 M in CH$_2$Cl$_2$) and then remove the solvent under reduced pressure to give a solid. Dry the solid at room temperature overnight in vacuo to give 82 mg of the title compound (100%): mass spectrum (ion spray): m/z=528.3 (M+H-TFA).

Preparation 17

6-(3,5-Difluoro-phenyl)-5-[4-(2-piperidin-1-yl-ethoxy)-phenoxy]-naphthalen-2-ol

Combine the compound of Preparation 1 (440 mg, 0.84 mmol), 3,5-difluoro-benzeneboronic acid (400 mg, 2.50 mmol), palladium(II)acetate (19 mg, 0.083 mmol), tricyclohexylphosphine (35 mg, 0.125 mmol), cesium fluoride (1.14 g, 7.52 mmol), acetonitrile (10 mL) and heat at 90° C. After 10 minutes, cool to ambient temperature, dilute with dichloromethane, load onto a 10 g SCX cartridge, wash with dichloromethane, methanol, water, methanol, elute with ammonia solution (2N NH$_3$ in methanol, 80 mL) and remove solvent under vacuum. Dissolve in dichloromethane, chromatograph on silica gel with dichloromethane/methanol mixtures and add 1M hydrogen chloride in diethyl ether (0.8 mL) to give 41.0 mg of 1-(2-{4-[2-(3,5-difluoro-phenyl)-6-methoxy-naphthalen-1-yloxy]-phenoxy}-ethyl)-piperidine hydrochloride (93%).
Dissolve 1-(2-{4-[2-(3,5-difluoro-phenyl)-6-methoxy-naphthalen-1-yloxy]-phenoxy}-ethyl)-piperidine hydrochloride (410 mg, 0.76 mmol) in dichloromethane (10 mL) and cool in an ice bath. Add boron tribromide (0.22 mL, 2.28 mmol) and stir for 2.5 hours. Add methanol (5 mL), warm to ambient temperature, dilute with dichloromethane and wash with saturated aqueous sodium bicarbonate, dry with solid magnesium sulfate, filter and remove solvent under vacuum. Chromatograph on silica gel with dichloromethane/methanol mixtures to give 350 mg of the title compound (96%).

EXAMPLE 54

6-(3,5-Bis-ethylsulfanyl-phenyl)-5-[4-(2-piperidin-1-yl-ethoxy)-phenoxy]-naphthalen-2-ol

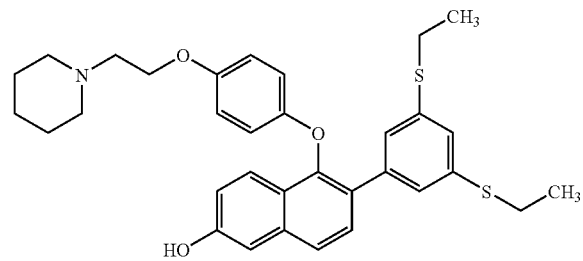

Combine 6-(3,5-difluoro-phenyl)-5-[4-(2-piperidin-1-yl-ethoxy)-phenoxy]-3-naphthalen-2-ol (300 mg, 0.63 mmol), sodium ethane thiol (530 mg, 6.33 mmol) and 1-methyl-2-pyrrolidinone (10 mL) and heat to 130° C. for 4.5 hours. Cool to ambient temperature, dilute with dichloromethane, wash with brine and a saturated sodium bicarbonate solution. Load organic phase onto a 10 g SCX cartridge, wash with dichloromethane, methanol, elute with ammonia solution (2N NH$_3$ in methanol, 80 mL) and remove solvent under vacuum. Dissolve in dichloromethane and chromatograph on silica gel with dichloromethane/methanol mixtures to give 260 mg of the title compound (74%). Mass spectrum (ion spray): m/z=560 (M+H).

EXAMPLE 55

6-(3,5-Bis-ethanesulfonyl-phenyl)-5-[4-(2-piperidin-1-yl-ethoxy)-phenoxy]-naphthalen-2-ol Dissolve the compound of Example 54 (160 mg, 0.29 mmol) in glacial acetic acid (5 mL). Add an acetic acid solution of 77% mCPBA (300 mg, 1.31 mmol theoretical) dropwise over 10 minutes and stir at ambient temperature for 1 hour. Remove solvent under reduced pressure. Partition with dichloromethane and saturated sodium bicarbonate solution, dry with solid magnesium sulfate, filter and chromatograph on silica gel with dichloromethane/methanol mixtures to give 130 mg of the title compound (72%). Mass spectrum (ion spray): m/z=624 (M+H).

EXAMPLE 56

6-(3,56-Bis-ethanesulfonyl-phenyl)-5-[4-(2-piperidin-1-yl-ethoxy)-phenoxy]-naphthalen-2-ol Hydrochloride Dissolve the compound of Example 55 in dichloromethane and add 1N HCl in Et$_2$O (0.180 mL). Evaporate to dryness to give the title compound.

Preparation 18

{4-[2-(4-Methanesulfonyl-phenyl)-6-methoxy-naphthalen-1-yloxy]-phenyl}-carbamic acid tert-butyl ester Heat a solution of 6-methoxytetralone (9.6 g, 54 mmol), 4-bromothioanisole (25 mL, 123 mmol), sodium tert-butoxide (20.9 g, 217 mmol), palladium (II) acetate (610 mg, 2.72 mmol), racemic 2,2'-bis(diphenylphosphino)-1,1'-binaphthyl (1.8 g, 2.72 mmol) and toluene (150 mL) at reflux for 18 hours, then cool to ambient temperature and evaporate to dryness under reduced pressure. Dissolve the residue in dichloromethane and wash with aqueous hydrochloric acid (1N), filter through celite and chromatograph twice on silica gel with hexane/ethyl acetate mixtures to give 2.41 g of 6-methoxy-2-(4-methylsulfanyl-phenyl)-naphthalen-1-ol (15%).
Stir a solution of 6-methoxy-2-(4-methylsulfanyl-phenyl)-naphthalen-1-ol (1.98 g, 6.68 mmol), 4-fluoro-nitrobenzene (0.78 mL, 7.34 mmol) and phosphazene base P$_4$-t-butyl (6.7 mL of 1M in hexane, 6.7 mmol) in N,N-dimethylformamide (30 mL) at ambient temperature for 4 hours. Dilute the reaction with dichloromethane, wash with 1N aqueous hydrochloric acid, water, dry with solid magnesium sulfate and chromatograph on silica gel with hexane/ethyl acetate mixtures to give 2.18 g of 6-methoxy-2-(4-methylsulfanyl-phenyl)-1-(4-nitro-phenoxy)-naphthalene (78%)
Add 77% mCPBA (340 mg, 2.00 mmol) to a solution of 6-methoxy-2-(4-methylsulfanyl-phenyl)-1-(4-nitro-phenoxy)-naphthalene (270 mg, 0.66 mmol) in dichloromethane (10 mL). Stir the reaction for 30 minutes, wash with saturated sodium carbonate solution, dry with solid magnesium sulfate and filter through a 1 inch pad of silica gel to give 290 mg of 2-(4-methanesulfonyl-phenyl)-6-methoxy-1-(4-nitro-phenoxy)-naphthalene (98%).

Heat a solution of 2-(4-methanesulfonyl-phenyl)-6-methoxy-1-(4-nitro-phenoxy)-naphthalene (1.67 g, 3.7 mmol), ammonium formate (4.7 g, 74 mmol), wet 20% palladium hydroxide on carbon (420 mg, 25 wt %) and absolute ethanol (80 mL) at reflux for 1 hour, then cool to ambient temperature, filter and evaporate to dryness under reduced pressure. Partition the residue with dichloromethane/water. Dry the organic layer with solid magnesium sulfate and chromatograph on silica gel with dichloromethane/methanol mixtures to give 1.15 g of 4-[2-(4-methanesulfonyl-phenyl)-6-methoxy-naphthalen-1-yloxy]-phenylamine (75%).

Heat a solution of 4-[2-(4-methanesulfonyl-phenyl)-6-methoxy-naphthalen-1-yloxy]-phenylamine (170 mg, 9.41 mmol) and di-tert-butyl dicarbonate (140 mg, 0.66 mmol) in tetrahydrofuran (10 mL) at reflux for 4 hours, then cool to ambient temperature and evaporate to dryness under reduced pressure. Chromatograph the residue on silica gel with dichloromethane/ethyl acetate mixtures to give 210 mg of {4-[2-(4-methanesulfonyl-phenyl)-6-methoxy-naphthalen-1-yloxy]-phenyl}-carbamic acid tert-butyl ester (97%).

EXAMPLE 57

{4-[2-(4-Methanesulfonyl-phenyl)-6-methoxy-naphthalen-1-yloxy]-phenyl}-(2-piperidin-1-yl-ethyl)-carbamic acid tert-butyl ester

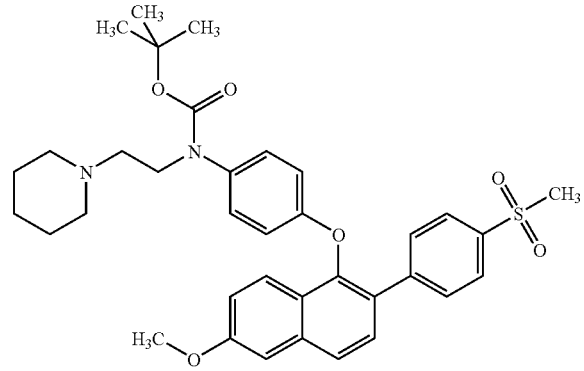

Heat a solution of {4-[2-(4-methanesulfonyl-phenyl)-6-methoxy-naphthalen-1-yloxy]-phenyl}-carbamic acid tert-butyl ester (200 mg, 0.38 mmol), 2-chloroethyl-1-piperidine hydrochloride (100 mg, 0.57 mmol) and 60% sodium hydride (38 mg, 0.94 mmol) in N,N-dimethylformamide to 60° C. and stir for 18 hours. Add potassium tert-butoxide (760 mg, 0.67 mmol) and 2-chloroethyl-1-piperidine hydrochloride (46 mg, 0.25 mmol) and stir for an additional 2 hours, then cool to ambient temperature. Dilute the reaction with dichloromethane, wash with saturated sodium bicarbonate, dry with magnesium sulfate and chromatograph on silica gel with dichloromethane/methanol mixtures to give 120 mg of the title compound (50%). Mass spectrum (ion spray): m/z=631.3 (M+H).

EXAMPLE 58

6-(4-Methanesulfonyl-phenyl)-5-[4-(2-piperidin-1-yl-ethylamino)-phenoxy]-naphthalen-2-ol Dihydrochloride Add 4M HCl/dioxane (3 mL, 12 mmol) to a solution of the compound of Example 57 (10 mg, 0.17 mmol) in dichloromethane (3 mL) and stir the reaction for 40 minutes, then evaporate to dryness under reduced pressure. Dissolve the residue in dichloromethane (4 mL) and add boron tribromide (0.068 mL, 0.72 mmol). Stir the reaction for 3.5 hours, then add aqueous saturated sodium bicarbonate (5 mL) and allow the phases to separate. Dry the organic layer with solid magnesium sulfate and chromatograph on silica gel with dichloromethane/methanol mixtures. Evaporate the fractions containing product to dryness and redissolve in 5% methanol/dichloromethane (3 mL). Add 1M hydrogen chloride in diethyl ether (0.28 mL) then evaporate the solution under reduced pressure to give 82 mg of the title compound (77%). Mass spectrum (ion spray): m/z=517.5 (M+H).

EXAMPLE 59

5-[4-(2-Azepin-1-yl-ethylamino)-phenoxy]-6-(4-methanesulfonyl-phenyl)-naphthalen-2-ol Dihydrochloride

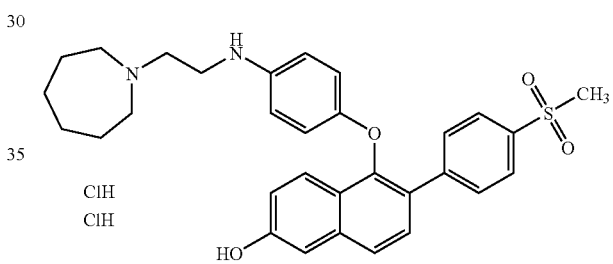

Using procedures similar to Preparation 18 and Example 58, convert {4-[2-(4-methanesulfonyl-phenyl)-6-methoxy-naphthalen-1-yloxy]-phenyl}-carbamic acid tert-butyl ester (200 mg, 0.39 mmol) and 2-(hexamethyleneimino)-ethyl chloride hydrochloride (140 mg, 0.70 mmol) to 77 mg of the title compound (37%). Mass spectrum (ion spray): m/z=531 (M+H).

Preparation 19

4-[2-(4-Methanesulfonyl-phenyl)-6-methoxy-naphthalen-1-yloxy]-phenol

Add 4-fluoro-benzaldehyde (2.20 mL, 20.3 mmol) to a solution of 6-methoxy-2-(4-methylsulfanyl-phenyl)-naphthalen-1-ol (3.0 g, 10.1 mmol) and 60% sodium hydride (400 mg, 10.1 mmol) in 1-methyl-2-pyrolidinone (30 mL). Heat the reaction to 170° C. for 70 minutes, then cool to ambient temperature. Dilute the reaction with ethyl acetate (200 mL) and wash twice with 5% aqueous lithium chloride (500 mL), brine, 1N aqueous hydrochloric acid, dry with solid magnesium sulfate and chromatograph on silica gel with dichloromethane/hexane mixtures to give 1.29 g of 4-[6-methoxy-2-(4-methylsulfanyl-phenyl)-naphthalen-1-yloxy]-benzaldehyde (32%).

Combine 4-[6-methoxy-2-(4-methylsulfanyl-phenyl)-naphthalen-1-yloxy]-benzaldehyde (970 mg, 2.49 mmol), sodium perborate monohydrate (2.5 mmol) and glacial acetic acid (16 mL). Stir for 4 hours at ambient temperature, then evaporate to dryness under reduced pressure. Partition with dichloromethane/50% saturated aqueous sodium bicarbonate solution. Wash the organic layer with brine, dry with solid magnesium sulfate, filter and chromatograph on silica gel with dichloromethane/methanol mixtures to give 280 mg of the title compound (27%). Mass spectrum (ion spray): m/z=419 (M−1).

EXAMPLE 60

1-(2-{4-[2-(4-Methanesulfonyl-phenyl)-6-methoxy-naphthalen-1-yloxy]-phenoxy}-ethyl)-azepine Hydrochloride

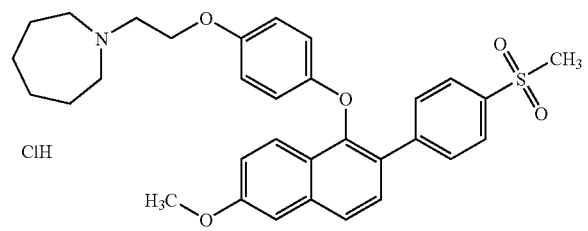

Stir a solution of 4-[2-(4-methanesulfonyl-phenyl)-6-methoxy-naphthalen-1-yloxy]-phenol (160 mg, 0.39 mmol), 2-(hexamethyleneimino)-ethyl chloride hydrochloride (140 mg, 0.69 mmol), 60% sodium hydride (47 mg, 1.18 mmol) and N,N-dimethylformamide (2 mL) for 18 hours at ambient temperature, then evaporate under reduced pressure. Dissolve the residue in dichloromethane and wash with water, dry with solid magnesium sulfate and chromatograph on silica gel with dichloromethane/methanol mixtures. Combine the fractions containing product and add 1N hydrogen chloride in diethyl ether (0.30 mL). Concentrate the resulting solution under reduced pressure to give 160 mg of the title compound (69%). Mass spectrum (ion spray): m/z=546 (M+H).

EXAMPLE 61

5-[4-(2-Azepin-1-yl-ethoxy)-phenoxy]-6-(4-methanesulfonyl-phenyl)-naphthalen-2-ol Hydrochloride Convert the compound of Example 60 (160 mg, 0.27 mmol) to 5-[4-(2-azepin-1-yl-ethoxy)-phenoxy]-6-(4-methanesulfonyl-phenyl)-naphthalen-2-ol using a procedure similar to Preparation 15 (85%). Dissolve the free base in dichloromethane, add 1N HCl in Et₂O (0.250 mL) then concentrate to give 140 mg of the title compound. Mass spectrum (ion spray): m/z=532 (M+H).

Preparation 20

N-tert-Butyl-4-(4,4,5,5-tetramethyl-[1,3,2]dioxaborolan-2-yl)-benzenesulfonamide Place t-butylamine (4.32 mL, 41.1 mmol), triethylamine (8.15 mL, 58.7 mmol) and dichloromethane (75 mL) in a 3-neck round bottom flask. Cool this stirring solution to 0° C. and add a solution of 4-bromobenzenesulfonyl chloride (10.0 g, 39.1 mmol) in dichloromethane (50 mL). Add additional dichloromethane (25 mL) and stir the reaction overnight, allowing it to warm to ambient temperature. Evaporate the reaction in vacuo. Suspend the resulting white solid in ethyl acetate and filter it. Concentrate the filtrate in vacuo and purify the resulting residue by flash chromatography (silica gel; 50%-80% gradient CH₂Cl₂ in hexanes) to provide 9.85 g of 4-bromo-N-tert-butyl-benzenesulfonamide (86%).

Place 4-bromo-N-tert-butyl-benzenesulfonamide (2.00 g, 6.84 mmol), bis(pinacolato)diboron (2.09 g, 8.21 mmol), PdCl₂(dppf)₂⁻CH₂Cl₂ (175 mg, 0.24 mmol), potassium acetate (2.02 g, 20.5 mmol) and anhydrous dimethyl sulfoxide (25 mL) in a round bottom flask. Put the reaction in an oil bath and stir it at 90° C. for 7.5 hours. Cool the purple colored reaction to ambient temperature, quench with ample water and extract the resulting aqueous mixture into dichloromethane. Wash the combined extracts with water and brine; then dry (sodium sulfate) and evaporate them in vacuo. Purify the resulting dark solid on a flash column (silica gel; 0%-5% gradient of EtOAc in CH₂Cl₂) to provide 2.00 g of the title compound (86%).

EXAMPLE 62

N-tert-Butyl-4-{6-methoxy-1-[4-(2-piperidin-1-yl-ethoxy)-phenoxy]-naphthalen-2-yl}-benzenesulfonamide

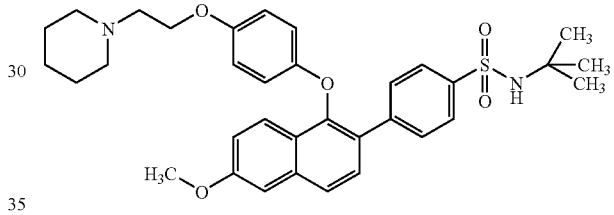

Add the compound of Preparation 1 (335 mg, 0.64 mmol), N-tert-butyl-4-(4,4,5,5-tetramethyl-[1,3,2]dioxaborolan-2-yl)-benzenesulfonamide (650 mg, 1.92 mmol) and acetonitrile (6 mL) to a round bottom flask containing cesium fluoride (875 mg, 5.79 mmol) and acetonitrile (6 mL). To this mixture, add a sonicated suspension of palladium (II) acetate (14 mg, 0.064 mmol) and tricyclohexylphosphine (27 mg, 0.096 mmol) in acetonitrile (2 mL). Add additional acetonitrile (2 mL) and place the reaction in an oil bath at 90° C. Stir the reaction for 20 minutes at 90° C. Cool the reaction'to ambient temperature and then filter it through a pad of Celite (rinse with ample, hot ethyl acetate). Wash the filtrate with 50% aqueous sodium carbonate, saturated aqueous ammonium chloride, water and brine; then dry (sodium sulfate) and evaporate the filtrate in vacuo. Purify the resulting solid on a 25M silica colunm (2%-4% MeOH gradient in CH₂Cl₂) to provide 315 mg of the title compound (84%). MS (IS+) m/e 589 (M+1).

EXAMPLE 63

N-tert-Butyl-4-{6-hydroxy-1-[4-(2-piperidin-1-yl-ethoxy)-phenoxy]-naphthalen-2-yl}-benzenesulfonamide Hydrochloride Place the product of Example 62 (30 mg, 0.051 mmol), sodium ethanethiolate (43 mg, 0.51 mmol) and dimethylformamide (2 mL) in a round bottom flask, at room temperature. Place the reaction in a 90° C. oil bath and stir it for 3 hours, then cool it to ambient temperature. Quench the room temperature reaction with brine and extract it into ethyl acetate.

Wash the combined extracts with saturated aqueous sodium bicarbonate, water and brine; then dry (sodium sulfate) and concentrate the extracts in vacuo. Purify the crude material on a Chromatotron (silica gel; 6%-10% MeOA gradient in $CH_2Cl_2$). Dissolve the purified solid in methanol (4 mL) and add a 1.0 M hydrochloric acid in diethyl ether solution (0.10 mL) to it. Shake the resulting solution for two minutes at room temperature and then evaporate it in vacuo to give 25 mg of the title compound (80%); MS (IS+) m/e 575 (M+1-HCl).

Preparation 21

N,N-Dimethyl-4-(4,4,5,5-tetramethyl-[1,3,2]dioxaborolan-2-yl)-benzenesulfonamide Place dimethylamine (5.25 mL of a 2.0 M solution in THF, 10.4 mmol), triethylamine (2.04 mL, 14.68 mmol) and dichloromethane (30 mL) in a round bottom flask. Cool this solution to 0° C., while stirring, and add a solution of 4-bromobenzenesulfonyl-chloride (2.5 g, 9.78 mmol) in dichloromethane (30 mL); Add additional dichloromethane (10 mL) and stir the reaction overnight, letting it warm to ambient temperature. Concentrate the reaction in vacuo. Take up the resulting solid in ethyl acetate and filter. Evaporate the filtrate in vacuo and dry the resulting solid by vacuum to give 2.50 g of 4-bromo-N,N-dimethyl-benzenesulfonamide (97%).

Place 4-bromo-N,N-dimethyl-benzenesulfonamide (1.00 g, 3.77 mmol); bis(pinacolato)diboron (1.15 g, 4.53 mmol), $PdCl_2(dppf)_2 \cdot CH_2Cl_2$ (97 mg, 0.13 mmol), potassium acetate (1.11 g, 11.32 mmol) and anhydrous dimethyl sulfoxide (12 mL) in a round bottom flask. Put the reaction in an oil bath and stir at 90° C. for 8 hours. Cool the purple colored reaction to ambient temperature, quench with ample water and extract the resulting aqueous mixture into dichloromethane. Wash the combined extracts with water and brine; then dry (sodium sulfate) and evaporate the extracts in vacuo. Purify the resulting solid on a flash column (silica gel; 2%-5% gradient of EtOAc in $CH_2Cl_2$, load material in $CH_2Cl_2$) to provide 900 mg of the title compound (77%).

EXAMPLE 64

4-{6-Methoxy-1-[4-(2-piperidin-1-yl-ethoxy)-phenoxy]-naphthalen-2-yl}-N,N-dimethyl-benzenesulfonamide

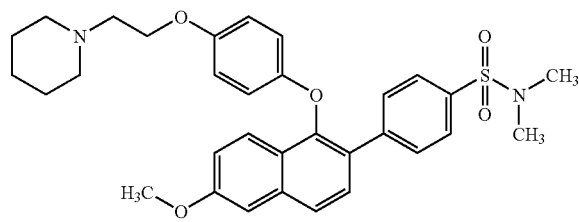

In a round bottom flask add the compound of Preparation 1 (175 mg, 0.33 mmol), N,N-dimethyl-4-(4,4,5,5-tetramethyl-[1,3,2]dioxaborolan-2-yl)-benzenesulfonamide (311 mg, 0.99 mmol), acetonitrile (7 mL) and cesium fluoride (455 mg, 2.99 mmol). To this mixture add a sonicated suspension of palladium (II) acetate (8 mg, 0.033 mmol) and tricyclohexylphosphine (14 mg, 0.050 mmol) in acetonitrile (1 mL), followed by additional acetonitrile (3 mL). Place the reaction in a 90° C. oil bath and stir for 10 minutes, then add more acetonitrile (3 mL). Heat the reaction at 90° C., with stirring, for 10 more minutes. Cool the reaction to ambient temperature and filter it through a pad of Celite (rinse with ample, hot ethyl acetate). Wash the filtrate with 50% aqueous sodium carbonate, saturated aqueous ammonium chloride and brine; then dry (sodium sulfate) and evaporate it in vacuo. Purify the resulting solid on a Chromatotron (silica gel; 3%-8% MeOH gradient in $CH_2Cl_2$) to obtain 160 mg of the title compound (87%). MS (IS+) 7 m/e 561 (M+1).

EXAMPLE 65

4-{6-Hydroxy-1-[4-(2-piperidin-1-yl-ethoxy)-phenoxy]-naphthalen-2-yl}-N,N-dimethyl-benzenesulfonamide Hydrochloride In a round bottom flask place the product of Example 64 (120 mg, 0.214 mmol), dichloromethane (5 mL) and a 1.0 M hydrochloric acid in diethyl ether solution (0.43 mL, 0.43 mmol). Shake this solution at ambient temperature for 2 minutes then evaporate it in vacuo. After drying on vacuum, add dichloromethane (10 mL) and place this solution in an ice bath with stirring. Add a solution of 1.0 M boron tribromide in dichloromethane (0.750 mL, 0.750 mmol) and stir the reaction for 3-4 hours, keeping the temperature between 0° C.-10° C. Quench the reaction over saturated aqueous sodium bicarbonate then extract it into ethyl acetate. Wash the combined extracts with saturated aqueous sodium bicarbonate, water and brine; then-dry (sodium sulfate) and evaporate them in vacuo. Purify the crude solid on a Chromatotron (silica gel; 5%-11% MeOH gradient in $CH_2Cl_2$; loaded with 7% MeOH/$CHCl_3$). Dissolve the purified material in methanol (5 mL) and add a 1.0 M hydrochloric acid in diethyl ether solution (0.43 mL). Shake the resulting solution for two minutes at room temperature then evaporate it in vacuo to give 96 mg of the title compound (77%). MS (IS+) m/e 547 (M+1-HCl).

Preparation 22

4-(4,4,5,5-Tetramethyl-[1,3,2]dioxaborolan-2-yl)-benzenesulfonic acid 2,2-dimethyl-propyl ester Add 4-bromobenzenesulfonyl chloride (2.20 g, 8.61 mmol) and pyridine (30 mL) to a round bottom flask. At ambient temperature, with stirring, add neopentyl alcohol (1.39 mL, 12.91 mmol). After stirring the reaction overnight at ambient temperature quench the reaction with saturated aqueous sodium bicarbonate and extract it with ethyl acetate. Wash the combined extracts with saturated aqueous sodium bicarbonate, 0.05 N aqueous hydrochloric acid and brine, then dry (sodium sulfate), and concentrate in vacuo. Purify the resulting-material on a flash column (silica gel; 30%-50% gradient of $CH_2Cl_2$ in hexanes) to provide 2.24 g of 4-bromobenzenesulfonic acid 2,2-dimethyl-propyl ester (85%).

Place 4-bromo-benzenesulfonic acid 2,2-dimethyl-propyl ester (1.00 g, 3.26 mmol), bis(pinacolato)diboron (1.07 g, 4.23 mmol), $PdCl_2(dppf)_2 \cdot CH_2Cl_2$ (90 mg, 0.12 mmol), potassium acetate (1.04 g, 10.6 mmol) and anhydrous dimethyl sulfoxide (12 mL) in a round bottom flask. Put the reaction in an oil bath and stir at 90° C. for 1 to −1.5 hours. Cool the reaction to ambient temperature, quench with ample water and extract the resulting aqueous mixture into dichloromethane. Wash the combined extracts with water and brine; then dry (sodium sulfate) and evaporate them in vacuo. Purify the resulting solid on a flash column (silica gel; gradient 10% hexane/$CH_2Cl_2$ to 100% $CH_2Cl_2$ to 5% EtOAc/$CH_2Cl_2$) to provide 950 mg of the title compound (82%).

EXAMPLE 66

4-{6-Benzyloxy-1-[4-(2-piperidin-1-yl-ethoxy)-phenoxy]-naphthalen-2-yl}-benzenesulfonic acid 2,2-dimethyl-propyl ester

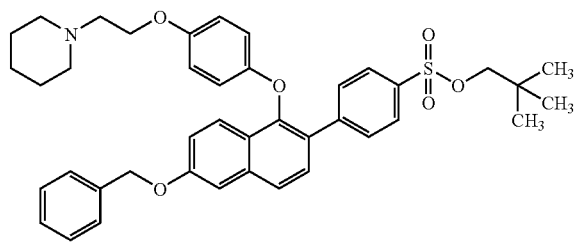

In a round bottom flask add the compound of Preparation 3 (50 mg, 0.078 mmol), 4-(4,4,5,5-tetramethyl-[1,3,2]dioxaborolan-2-yl)-benzenesulfonic acid 2,2-dimethyl-propyl ester (83' mg, 0.24 mmol) and acetonitrile (2 mL). To this solution add a sonicated suspension of palladium (II) acetate (2 mg, 0.008 mmol) and tricyclohexylphosphine (3 mg, 0.012 mmol), cesium fluoride (107 mg, 0.71 mmol) in acetonitrile (1 mL). Place the reaction in an oil bath at 90° C., and stir for 20 minutes. Then cool the reaction to ambient temperature and filter it through a pad of Celite (rinse with ample, hot ethyl acetate). Wash the filtrate with 50% aqueous sodium carbonate, saturated aqueous ammonium chloride and brine; then dry (sodium sulfate) and evaporate it in vacuo. Purify the resulting solid on a Chromatotron (silica gel; 2%-6% MeOH gradient in $CH_2Cl_2$) to obtain 320 mg of the title compound (60%). MS (IS+) m/e 680 (M+1).

EXAMPLE 67

4-{6-Hydroxy-1-[4-(2-piperidin-1-yl-ethoxy)-phenoxy]-naphthalen-2-yl}-benzenesulfonic acid 2,2-dimethyl-propyl ester Hydrochloride

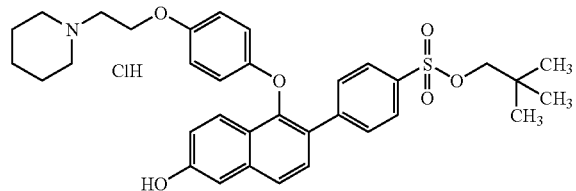

To a round bottom flask add the product from Example 66 (42 mg, 0.062 mmol), ammonium formate (29 mg, 0.464 mmol), 10% Pd/C (6 mg, 15% by weight) and MeOH (5 mL). Heat the mixture at reflux for 35 minutes. Cool the reaction to ambient temperature and filter it through a pad of Celite, then rinse the Celite with hot ethyl acetate and hot methanol. Evaporate the filtrate in vacuo and purify the resulting residue by radial chromatography over silica (2-5% MeOH gradient in $CH_2Cl_2$) to provide 27 mg of 4-{6-hydroxy-1-[4-(2-piperidin-1-yl-ethoxy)-phenoxy]-naphthalen-2-yl}-benzenesulfonic acid 2,2-dimethyl-propyl ester (74%). Dissolve the free base (6.7 mg) in $CH_2Cl_2$ (3 mL) and add 0.023 mL (2 equivalents (eq.)) of a 1.0M solution of hydrochloric acid in diethyl ether. Shake this solution for 1-2 minutes at ambient temperature and evaporate it in vacuo to provide 7.1 mg of the title compound. MS (IS+) m/e 590 (M+1-HCl).

EXAMPLE 68

N-tert-Butyl-4-{6-methoxy-1-[4-(2-piperidin-1-yl-ethoxy)-phenoxy]-naphthalen-2-yl}-N-methyl-benzenesulfonamide To a stirring room temperature solution of the product of Example 62 (79 mg, 0.013 mmol) in dimethylformamide (5 mL) add 60% sodium hydride (6 mg, 0.15 mmol). Stir this mixture at ambient temperature for 10 minutes and then add iodomethane (0.014 mL, 0.15 mmol). Stir the reaction for 30 minutes at ambient temperature then quench it with brine. Extract the resulting aqueous mixture into ethyl acetate. Wash the combined extracts with brine; dry (sodium sulfate) and concentrate them in vacuo. Purify the resulting material on a Chromatotron (silica gel; 3%-10% MeOH gradient in $CH_2Cl_2$) to obtain 47 mg of the title compound (68%). MS (IS+) m/e 603 (M+1).

EXAMPLE 69

4-{6-Methoxy-1-[4-(2-piperidin-1-yl-ethoxy)-phenoxy]-naphthalen-2-yl}-N-methyl-benzenesulfonamide

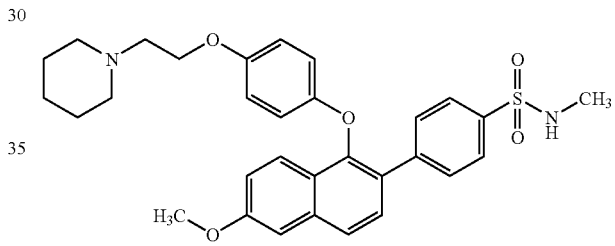

In a round bottom flask place the product of Example 68 (80 mg, 0.13 mmol) and trifluoroacetic acid (5 mL). Heat this solution at reflux for 15-20 minutes then cool to ambient temperature. Quench the reaction mixture by pouring it over saturated aqueous sodium bicarbonate then extract into ethyl acetate. Wash the combined extracts with saturated aqueous sodium bicarbonate, water and brine; then dry (sodium sulfate) and evaporate in vacuo. Purify the resulting material on a Chromatotron (silica gel; 4%-8% MeOH gradient in $CH_2Cl_2$) to obtain 63 mg of the title compound (89%). MS (IS+) m/e 547 (M+1).

EXAMPLE 70

4-{6-Hydroxy-1-[4-(2-piperidin-1-yl-ethoxy)-phenoxy]-naphthalen-2-yl}-N-methyl-benzenesulfonamide Hydrochloride In a round bottom flask place the product of Example 69 (85 mg, 0.146 mmol), dichloromethane (5 mL) and a solution of 1.0 M hydrochloric acid in diethyl ether (0.150 mL, 0.150 mmol). Shake this solution at ambient temperature for 2 minutes and then evaporate it in vacuo. After drying in vacuo, add dichloromethane (6 mL) and place this solution in an ice bath with stirring. Add a solution of 1.0 M boron tribromide in dichloromethane (0.32 mL, 0.32 mmol) and stir the reaction for 2-3 hours, keeping the temperature between 0° C.-10° C.

Quench the reaction over saturated aqueous sodium bicarbonate then extract it into ethyl acetate. Wash the combined extracts with saturated aqueous sodium bicarbonate, water and brine; then dry (sodium sulfate) and evaporate in vacuo. Purify the crude solid on a Chromatotron (silica gel; 6%-10% MeOH gradient in CH$_2$Cl$_2$). Dissolve the purified material in methanol (5 mL) and add a solution of 1.0 M hydrochloric acid in diethyl ether (0.30 mL). Shake the resulting solution for two minutes at room temperature then evaporate in vacuo to give 71 mg of the title compound (85%). MS (IS+) m/e 533 (M+1-HCl).

EXAMPLE 71

Isobutyric acid 6-(4-methanesulfonyl-phenyl)-5-[4-(2-piperidin-1-yl-ethoxy)-phenoxy]-naphthalen-2-yl ester Hydrochloride

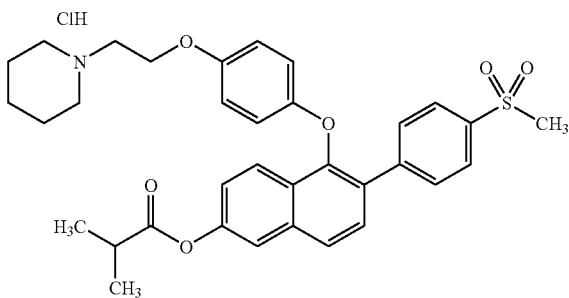

Add triethylamine (80 μL, 0.574 mmol) to a solution of the compound of Example 3 (103 mg, 0.186 mmol) in THF (5 mL). Cool the solution to 0° C. and add 4-dimethylaminopyridine (10 mg, 0.082 mmol) followed by dropwise addition of isobutyric anhydride (40 μL, 0.241 mmol). Allow the solution to warm to room temperature over 2 hours. Add additional isobutyric anhydride (200 μL, 1.206 mmol) and stir overnight at room temperature. Dilute the solution with EtOAc (20 mL), and wash with 1N HCl, saturated NaHCO$_3$, and brine. Dry the organic layer over Na$_2$SO$_4$, filter and concentrate in vacuo. Purify the crude residue by radial chromatography (80% CH$_2$Cl$_2$:18% EtOAc: 2% EtOH) to yield 82 mg of isobutyric acid 6-(4-methanesulfonyl-phenyl)-5-[4-(2-piperidin-1-yl-ethoxy)-phenoxy]-naphthalen-2-yl ester. Dissolve the free base in THF (5 mL) and add HCl (1.0M in Et$_2$O, 0.4 mL, 0.4 mmol) to the solution. Concentrate the solution in vacuo and crystallize the residue from Et$_2$O/EtOH to afford 53 mg of the title compound. MS (ion spray): 588 (M+H—HCl).

EXAMPLE 72

6-(4-Methanesulfonyl-phenyl)-5-[4-(2-piperidin-1-yl-ethoxy)-phenoxy]-naphthalen-2-ol Methanesulfonate Heat approximately 1.0 g of the compound of Example 3 in a solvent mixture consisting of 3 mL of 3A-ethanol and 5 mL ethyl acetate to provide a thin slurry. Add methanesulfonic acid (185 mg) in 1 mL of 3A-ethanol to the hot slurry. Cool and stir for approximately 1 hour upon reaching room temperature. Filter the slurry and rinse with ethyl acetate. Vacuum dry the filter cake at 45° C. over 2-3 days to recover approximately 1.11 g of the title compound.

EXAMPLE 73

6-(4-Methanesulfonyl-phenyl)-5-[4-(2-piperidin-1-yl-ethoxy)-phenoxy]-naphthalen-2-ol Succinate Heat approximately 1.0 g of the compound of Example 3 in a solvent mixture consisting of 10 mL of ethyl acetate and 1 mL 3A-ethanol. Add succinic acid (228 mg) to the hot slurry to provide a thin slurry. Add 2 mL of additional 3A-ethanol. Briefly re-heat the slurry back to reflux, then cool to room temperature and allow the mixture to stir 15-30 minutes before filtering. Rinse the filter cake with ethyl acetate and vacuum dry at 45° C. over 2-3 days to recover approximately 1.23 g of the title compound.

Preparation 23

Trifluoromethanesulfonic acid 6-methoxy-1-[4-(2-piperidin-1-yl-ethoxy)-benzoyl]-naphthalen-2-yl ester Dissolve 2,6-dimethoxynaphthalene (1.0 eq.) in CH$_2$Cl$_2$ (5 volume eq.) at ambient temperature in a dry round bottom flask equipped with stir bar, temperature probe and N$_2$ line. Cool the solution to 0° C. with an ice bath, and add 4-(2-piperidin-1-yl-ethoxy)-benzoyl chloride (1.1 eq.). Add aluminum chloride (2.0 eq.). Once the reaction is determined to be complete, quench the reaction slowly with 1 N NaOH and dilute with additional water and CH$_2$Cl$_2$. Wash the aqueous layer with CH$_2$Cl$_2$ (20 mL). Combine the organic extracts and wash with brine and dry (Na$_2$SO$_4$). Recrystallize the crude product from methanol to give (2,6-dimethoxy-naphthalen-1-yl)-[4-(2-piperidin-1-yl-ethoxy)-phenyl]-methanone.

Dissolve (2,6-dimethoxy-naphthalen-1-yl)-[4-(2-piperidin-1-yl-ethoxy)-phenyl]-methanone in CH$_2$Cl$_2$ (10 volume eq.) in a 3-neck round bottom flask equipped with a pressure equalizing addition funnel, stirbar, and N$_2$ source. Cool the flask in an ice/brine bath and add 1.0 M BCl$_3$ solution in CH$_2$Cl$_2$ (1.2 eq.) dropwise. The reaction solution turns dark red and the temperature initially increases to 5° C. After about 1 hour, quench the reaction with methanol (5 eq.) and allow to warm to room temperature. Dilute the organic solution with CH$_2$Cl$_2$ (one volume eq.) and add a 1.0 M NaHCO$_3$ solution (5 volume eq.) and stir for one hour. Separate the aqueous and organic layers. Wash the aqueous layer with CH$_2$Cl$_2$ (one volume) and combine the organic layers. Wash with saturated NH$_4$Cl and dry over Na$_2$SO$_4$. Purify the product via column chromatography (50/1 silica gel) eluting with CH$_2$Cl$_2$/hexanes (3/1) to yield (2-hydroxy-6-methoxy-naphthalen-1-yl)-[4-(2-piperidin-1-yl-ethoxy)-phenyl]-methanone.

Dissolve (2-hydroxy-6-methoxy-naphthalen-1-yl)-[4-(2-piperidin-1-yl-ethoxy)-phenyl]-methanone in CH$_2$Cl$_2$ (10 volumes) in a three neck round bottom flask equipped with a stir bar and N$_2$ source and chill to 0° C. in an ice/brine bath. Add pyridine (1.3 eq.). Add trifluoromethanesulfonyl chloride (1.2 eq.) via syringe over 15 minutes. After about 15 minutes, quench the reaction with H$_2$O (10 volumes), wash with 1 N aqueous HCl (5 volumes) and 1.0 N aqueous NaHCO$_3$, and dry over Na$_2$SO$_4$. Obtain the title compound in quantitative yield after concentration.

EXAMPLE 74

[2-(4-Methanesulfonyl-phenyl)-6-methoxy-naphthalen-1-yl]-[4-(2-piperidin-1-yl-ethoxy)-phenyl]-methanone

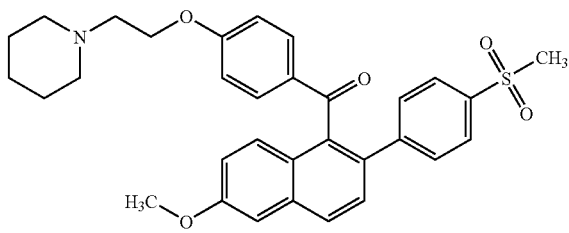

Dissolve trifluoro-methanesulfonic acid 6-methoxy-1-[4-(2-piperidin-1-yl-ethoxy)-benzoyl]-naphthalen-2-yl ester (555 mg, 1.0 mmol), 4-methansulfonylphenylboronic acid (310 mg, 1.55 mmol), Pd(OAc)$_2$ (23.9 mg, 0.11 mmol), Ph$_3$P (54.2 mg, 0.21 mmol) and Na$_2$CO$_3$ (2.5 mL, 2M in water) in ethyleneglycol dimethyl ether (DME, 30 mL). Reflux the mixture for 2 hours and add additional Pd(OAc)$_2$ (25.2 mg) and Ph$_3$P (58.9 mg). Reflux for 2 hours then dilute the reaction mixture with water and extract with chloroform. Dry the organic phase over Na$_2$SO$_4$, filter and concentrate. Purify the crude material by loading on an SCX column and eluting with 2M NH$_3$/MeOH to afford 569 mg of the title compound (101%). LCMS: m/z=544 (M+H)$^+$

EXAMPLE 75

[6-Hydroxy-2-(4-methanesulfonyl-phenyl)-naphthalen-1-yl]-[4-(2-piperidin-1-yl-ethoxy)-phenyl]-methanone Hydrochloride Add pyridine hydrochloride (4.0 g) to the compound of Example 74 (100 mg, 0.18 mmol). Purge the vessel with nitrogen, cap it, and heat to 200° C. for 4 hours. Cool to room temperature and dilute with saturated aqueous NaHCO$_3$. Extract with 25% isopropanol (i-PrOH) in CHCl$_3$, dry over Na$_2$SO$_4$ and concentrate in vacuo. Purify using an SCX column (eluting with 2M NH$_3$/MeOH) followed by flash chromatography (0-10% MeOH/CHCl$_3$). Dissolve the product in 1:1 CH$_3$CN/1M aqueous HCl and lyophilize to yield 70.3 mg of the title compound (68%). LCMS: m/z=530 (M+H)$^+$.

EXAMPLE 76

[2-(4-Methanesulfonyl-phenyl)-6-methoxy-naphthalen-1-yl]-[4-(2-piperidin-1-yl-ethoxy)-phenyl]-methanol Dissolve the compound of Example 74 (200 mg, 0.37 mmol) in THF (30 mL). Add lithium aluminum hydride (LAH, 70.3 mg). Quench with ice and water. Acidify with 1M aqueous HCl and make the solution slightly basic with aqueous NaHCO$_3$. Extract with 25% i-PrOH in CHCl$_3$. Purify the crude product using an SCX column eluting with 2M NH$_3$/MeOH to afford 185 mg of the title compound (92%) LCMS: m/z=546 (M+H)+

EXAMPLE 77

[2-(4-Methanesulfonyl-phenyl)-6-methoxy-naphthalen-1-yl]-[4-(2-piperidin-1-yl-ethoxy)-phenyl]-methane Dissolve the compound of Example 76 (185.2 mg, 0.33 mmol), Et$_3$SiH (0.3 mL, 1.88 mmol) and TFA (0.3 mL, 3.8 mmol) in CH$_2$Cl$_2$ (30 mL). Stir at room temperature for 1 hour. Quench with saturated aqueous NaHCO$_3$ and extract with 25% i-PrOH in CH$_2$Cl$_2$. Dry over Na$_2$SO$_4$, filter and concentrate. Purify the crude material by flash chromatography (0-5% MeOH/CH$_2$Cl$_2$ to afford 1.18 g of the title compound (63%). LCMS: m/z=530 (M+H)+

EXAMPLE 78

6-(4-Methanesulfonyl-phenyl)-5-[4-(2-piperidin-1-yl-ethoxy)-benzyl]-naphthalen-2-ol Hydrochloride Add pyridine hydrochloride (4 g) to the compound of Example 77 (110 mg, 0.21 mmol). Purge with nitrogen, cap the vessel and heat to 200° C. for 2 hours. Cool the reaction mixture and dilute with saturated aqueous NaHCO$_3$. Extract with CH$_2$Cl$_2$, dry over Na$_2$SO$_4$, filter and concentrate. Purify the crude product by flash chromatography (0-10% MeOH/CH$_2$Cl$_2$). Dissolve the product in 1:1 CH$_3$CN/1M aqueous HCl and lyophilize to afford 92 mg of the title compound (80%). LCMS: m/z=516 (M+H)$^+$—HCl.

Preparation 24

5-Bromo-1,3-difluoro-2-methanesulfonyl-benzene

Dissolve 1,3-difluorobenzene (3.5 g, 30.7 mmol) into THF (100 mL). Cool the mixture to −78° C. and add n-butyl lithium (19 mL, 30.7 mmol). Stir for 20 minutes and add dimethyldisulfide (3 mL, 3.38 mmol). Remove the cooling bath and warm to room temperature. Pour the reaction mixture into ice (10 g) and add diethyl ether (100 mL). Separate the layers and wash the organic layer with brine (20 mL). Dry with MgSO$_4$, filter, and concentrate in vacuo to give 4.3 g of 1,3-difluoro-2-methylsulfanyl-benzene (88%).

Combine 1,3-difluoro-2-methylsulfanyl-benzene (4.3 g, 27 mmol), iron (300 mg, 5.4 mmol), bromine (1.4 mL, 27 mmol), aluminium chloride (400 mg, 3.0 mmol) and dichloromethane (100 mL), at 0° C. Stir the reaction mixture at room temperature for 2 hours. Add saturated sodium thiosulfate solution (20 mL) and diethyl ether (100 mL). Separate the layers and wash the organic layer with brine (20 mL). Dry with MgSO$_4$, filter and concentrate in vacuo. Chromatograph the residue on a column eluting the material with diethyl ether in hexane (0 to 5%) to give 1.1 g of 5-bromo-1,3-difluoro-2-methylsulfanyl-benzene (17%).

Combine 5-bromo-1,3-difluoro-2-methylsulfanyl-benzene (1.1 g, 4.6 mmol), oxone (11 g, 18.4 mmol) and methanol (20 mL). Stir for 12 hours. Filter the suspension and evaporate the filtrate. Dissolve the residue in dichloromethane (100 mL) and add water (100 mL). Separate the organic layer and wash with brine (50 mL). Dry with MgSO$_4$, filter and concentrate in vacuo. Chromatograph the residue on a column eluting the material with diethyl ether in hexane (0 to 5%) to give 497 mg of the title compound (40%).

EXAMPLE 79

1-(2-{4-[2-(3,5-Difluoro-4-methanesulfonyl-phenyl)-6-methoxy-naphthalen 1-yloxy]-phenoxy}-ethyl)-piperidine

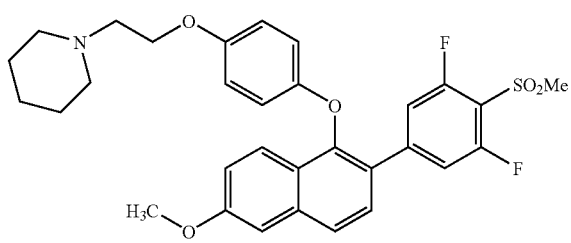

Combine palladium (II) acetate (13 mg, 0.06 mmol), tricyclohexylphosphine (27 mg, 0.10 mmol), cesium fluoride (518 mg, 3.4 mmol) and acetonitrile (10 mL). Stir for 5 minutes. Add the compound of Preparation 1 (200 mg, 0.38 mmol) and bis(neopentylglycolato)diboron (129 mg, 0.57 mmol). Heat to 90° C. for 1 minute and add 5-bromo-1,3-difluoro-2-methanesulfonyl-benzene (113 mg, 0.42 mmol) in acetonitrile (4 mL). Stir at 90° C. for 10 minutes. Cool to room temperature and dilute the solution with ethyl acetate (20 mL) and wash with saturated aqueous NaHCO₃ (10 mL). Separate the layers, wash the organic layer with brine (10 mL), dry with MgSO₄, filter, and concentrate in vacuo. Chromatograph the residue on a column eluting the material with methanol in dichloromethane (0 to 5%) to give 150 mg of the title compound (69%): mass spectrum (ion spray): m/z=568.3 (M+H).

EXAMPLE 80

6-(3,5-Difluoro-4-methanesulfonyl-phenyl)-5-[4-(2-piperidin-1-yl-ethoxy)-phenoxy]-naphthalen-2-ol Hydrochloride Dissolve the compound of Example 79 in ethyl acetate (10 mL) and diethyl ether (5 mL). Add 2M HCl in diethyl ether (0.1 mL, 0.2 mmol). Concentrate the slurry and dry int vacuo. Dilute the residue in dichloromethane (5.0 mL) and blanket with nitrogen. Cool the solution to 0° C. with an external ice bath. Add BBr₃ (0.1 mL, 1.1 mmol) and stir for 1 hour. Quench with water (1.0 mL) and dilute with dichloromethane (10 mL). Separate the layers, wash the organic layer with saturated aqueous NaHCO₃ (10 mL) and brine (10 mL). Dry with MgSO₄, filter, and concentrate in vacuo. Chromatograph the residue on a column eluting the 6-(3,5-difluoro-4-methanesulfonyl-phenyl)-5-[4-(2-piperidin-1-yl-ethoxy)-phenoxy]-naphthalen-2-ol with a step gradient of methanol/dichloromethane (0 to 5%). Dissolve the free base in diethyl ether (5.0 mL) and ethyl acetate (6.0 mL). Add 2M HCl in diethyl ether (0.1 mL, 0.2 mmol). Collect the precipitate on filter paper and rinse with diethyl ether to give 31 mg of the title compound (20%): mass spectrum (ion spray): m/z: 554.3 (M+H—HCl).

Preparation 25

Acetic acid 5-[4-(2-piperidin-1-yl-ethoxy)-phenoxy]-6-trifluoromethanesulfonyloxy-naphthalen-2-yl ester Dissolve the compound of Preparation 2 (800 mg, 1.33 mmol) in CH₂Cl₂ (20 mL) under N₂ and cool to 0° C. Add Et₃N (670 mg, 6.63 mmol) and Ac₂O (200 mg, 1.99 mmol) dropwise to the reaction mixture. Stir the solution for 3 hours. Add water (100 mL) and extract the aqueous layer with CH₂Cl₂ (3×100 mL). Combine the organic layers and dry with Na₂SO₄. Filter and concentrate to give 860 mg of the title compound as colorless oil (100%).

EXAMPLE 81

Acetic acid 6-(4-methanesulfonyl-3-methoxy-phenyl)-5-[4-(2-piperidin-1-yl-ethoxy)-phenoxy]-naphthalen-2-yl ester

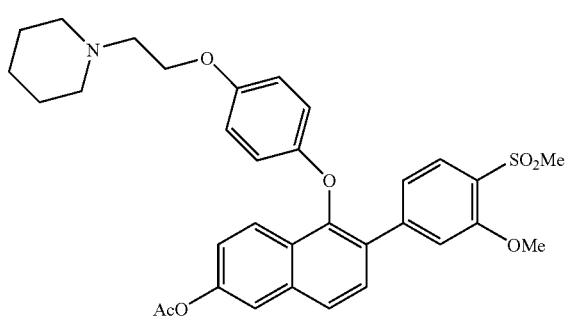

Combine Pd(OAc)₂ (46 mg, 0.20 mmol), tricyclohexylphosphine (95 mg, 0.34 mmol), and CsF (1.85 g, 12.26 mmol) in CH₃CN (20 mL) under N₂. Stir the reaction mixture for 5 minutes. Add acetic acid 5-[4-(2-piperidin-1-yl-ethoxy)-phenoxy]-6-trifluoromethanesulfonyloxy-naphthalen-2-yl ester (730 mg, 1.36 mmol) and bis(neopentyl glycolato)diboron (460 mg, 2.04 mmol) to the reaction mixture. Heat to 90° C. and stir for about 5 minutes. Add trifluoromethanesulfonic acid 4-methanesulfonyl-3-methoxy-phenyl ester (500 mg, 1.5 mmol) and continue to heat the mixture for two hours. Cool to room temperature, add water (100 mL), and extract the aqueous layer with CH₂Cl₂ (3×100 mL). Combine the organic layers and dry with Na₂SO₄, filter and concentrate. Purify by flash column chromatography (silica gel, 0 to 5% MeOH/CH₂Cl₂) to give 260 mg of the title compound (33%): mass spectrum: (ion spray): m/z=590.4 (M+H).

EXAMPLE 82

6-(4-Methanesulfonyl-3-methoxy-phenyl)-5-[4-(2-piperidin-1-yl-ethoxy)-phenoxy]-naphthalen-2-ol Hydrochloride Dissolve the compound of Example 81 (210 mg, 0.36 mmol) in MeOH (4 mL). Add NaHCO₃ (60 mg, 0.72 mmol) and stir the reaction mixture for 12 hours at room temperature. Filter and remove the solvent under reduced pressure. Purify the residue by flash column chromatography (silica gel, 2 to 10% MeOH—NH₄OH (10/1, v/v)/CH₂Cl₂) to give 150 mg of 6-(4-methanesulfonyl-3-methoxy-phenyl)-5-[4-(2-piperidin-1-yl-ethoxy)-phenoxy]-naphthalen-2-ol (75%). Dissolve the free base (150 mg, 0.27 mm iol) in CH₂Cl₂ (5 mL) and cool to −78° C. Add 2M HCl in diethyl ether (0.2 mL) and stir the solution for 5 minutes. Remove the solvent under reduced pressure to give a solid. Dry the solid at room temperature overnight in vacuo to give 140 mg of the title compound (87%): mass spectrum (ion spray): m/z=548.1 (M+H—HCl).

Preparation 26

2-(4-propylsulfanyl-phenyl)-boronic acid

Dissolve 4-bromo-benzenethiol (2.0 g, 10.6 mmol) in dry dimethylformamide (50 mL) and cool to 0° C. under nitrogen. Add sodium hydride (305 mg, 12.7 mmol) in portions. After the vigorous gas evolution stops, add 1-bromo-propane (1.4 mL, 15.9 mmol) and stir the reaction mixture overnight at room temperature. Slowly pour the reaction into water (400 mL) and extract with diethyl ether (2×150 mL). Wash the combined organic layers with water (100 mL). Dry the organic layer with sodium sulfate, filter and concentrate in vacuo to yield 2.7 g of 1-bromo-4-propylsulfanyl-benzene (quantitative yield).

Dissolve 1-bromo-4-propylsulfanyl-benzene (2.7 g, 11.6 mmol) in dry tetrahydrofuran (100 mL) and cool the solution to −78° C. Add 2.5 M butyllithium in hexanes (5.1 mL, 12.8 mmol) dropwise and allow the reaction mixture to warm to −40° C. Stir for 30 minutes and cool the reaction to −78° C. Add triisopropyl borate (8.0 mL, 34.8 mmol) and allow the reaction mixture to slowly warm to room temperature. Add 10% aqueous potassium hydroxide (100 mL, 179 mmol) and stir overnight. Slowly pour the reaction mixture into a mixture of concentrated HCl and ice. Extract the aqueous solution with dichloromethane, dry with sodium sulfate and concentrate in vacuo to yield 1.9 g of the title compound (86%).

EXAMPLE 83

1-(2-{4-[2-(4-propylsulfanyl-phenyl)-6-methoxy-naphthalen-1-yloxy]-phenoxy}-ethyl)-piperidine

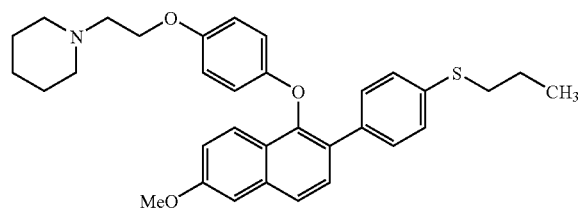

Combine 2-(4-propylsulfanyl-phenyl)-boronic acid (168 mg, 0.85 mmol), the compound of Preparation 1 (150 mg, 0.28 mmol) and cesium fluoride (214 mg, 1.4 mmol) in a flame-dried flask fitted with a reflux condenser and purge with nitrogen. In a separate dried flask combine palladium (II) acetate (6.2 mg, 0.03 mmol) and tricyclohexylphosphine (12 mg, 0.04 mmol). Add dry acetonitrile (3 mL) and sonicate for 10 minutes under nitrogen. Add the catalyst mixture to the solids and plunge the flask into a 90° C. oil bath. After 30 minutes cool the suspension to room temperature and filter through celite. Concentrate the filtrate in vacuo. Chromatograph the resultant residue on a SiO$_2$ column with methanol in dichloromethane (2%) to give 77 mg of the title compound (51%): mass spectrum (ion spray): m/z=528.3 (M+H).

EXAMPLE 84

6-(4-propylsulfanyl-phenyl)-5-[4-(2-piperidin-1-yl-ethoxy)-phenoxy]-naphthalen-2-ol Dissolve the compound of Example 83 (77 mg, 0.15 mmol) in dichloromethane (2 mL). Add 2M HCl in diethyl ether (0.15 mL, 0.29 mmol) and stir for 1 minute. Remove the solvent in vacuo and place on a high vacuum pump for 20 minutes. Dissolve the foam in dry dichloromethane (2 mL) and cool to 0° C. Add BBr$_3$ (70 µL, 0.73 mmol) dropwise. Stir for 30 minutes, quench by pouring into saturated aqueous sodium bicarbonate (10 mL) and extract with dichloromethane (2×10 mL). Dry the combined organic layers with sodium sulfate and concentrate in vacuo. Chromatograph the residue on a SiO$_2$ column with methanol in dichloromethane (5%) to yield 58 mg of the title compound (78%): mass spectrum (ion spray): m/z=514.3 (M+H).

EXAMPLE 85

5-[4-(2-Piperidin-1-yl-ethoxy)-phenoxy]-6-[4-(propane-1-sulfonyl)-phenyl]-naphthalen-2-ol Dissolve the compound of Example 84 (58 mg, 0.11 mmol) in glacial acetic acid (1.1 mL) and add sodium perborate (33 mg, 0.33 mmol). Stir the reaction mixture overnight and pour into saturated aqueous sodium bisulfite (10 mL). Extract with dichloromethane (2×10 mL) and wash the combined organic layers with saturated aqueous sodium bicarbonate (10 mL). Dry the organic layer with sodium sulfate, filter and concentrate in vacuo. Chromatograph the residue on a SiO$_2$ column with methanol in dichloromethane (5%) to yield 28 mg of the title compound (47%): mass spectrum (ion spray) m/z=546.3 (M+H).

EXAMPLE 86

5-[4-(2-Piperidin-1-yl-ethoxy)-phenoxy]-6-[4-(propane-1-sulfonyl)-phenyl]-naphthalen-2-ol Hydrochloride Dissolve the compound of Example 85 (28 mg, 0.05 mmol) in dry dichloromethane (1 mL) and add 2M HCl in diethyl ether (0.10 mL, 0.20 mmol). Stir at room temperature for 10 minutes. Remove the solvent with a stream of nitrogen and dry the solids in a vacuum oven at 50° C. overnight to yield 27.9 mg of the title compound (93%): mass spectrum (ion spray) m/z=546.3 (M+14-HCl).

Preparation 27

1-{2-[4-(6-Benzyloxy-2-bromo-benzo[b]thiophen-3-yloxy)-phenoxy]-ethyl}-piperidine Dissolve 6-methoxy-benzo[b]thiophene (*J. Med. Chem.* 32:2548, 1989; 26.1 g, 146 mmol) in DMF (500 mL). Add ethanethiol sodium salt (37 g, 440 mmol) and heats to 150° C. with stirring overnight. Add additional ethanethiol sodium salt (112.8 g, 152 mmol) and continue to heat at 150° C. overnight. Concentrate in vacuo to ¼ volume. Partition reaction mixture between ethyl acetate (500 mL) and water (500 mf), separate layers, wash organic layer with water (2×500 mL), brine (500 mL), and dry with magnesium sulfate. Filter and concentrate in vacuo to give 8 g of benzo[b]thiophen-6-ol. Back extract aqueous layers with ethyl acetate (3×1000 mL) wash organics with brine, and dry with magnesium sulfate. Concentrate in vacuo to obtain an additional 15 grams of benzo[b]thiophen-6-ol. Distill off remaining DMF to yield 22.7 g (100%) of benzo[b]thiophen-6-ol.

Dissolve benzo[b]thiophen-6-ol (10 g, 67 mmol) in pyridine (300 mL). Add 2,2-dimethyl-propionyl chloride (38 mL, 308 mmol) dropwise, and stir at room temperature for 8 hours. Concentrate in vacuo to ¼ Volume, partition between ethyl acetate (250 mL) and water (250 mL). Separate layers, wash organic layer with water (250 mL) and brine (200 mL). Dry with magnesium sulfate, filter, and concentrate in vacuo to give 15 g of 2,2-dimethyl-propionic acid benzo[b]thiophen-6-yl ester (98%).

Dissolve 2,2-dimethyl-propionic acid benzo[b]thiophen-6-yl ester (22.0 g, 94.0 mmol) in dichloromethane (500 mL). Add bromine (112.6 mL, 244 mmol), dropwise, and stir at room temperature for 2 hours. Add the reaction mixture into saturated aqueous sodium thiosulfate (500 mL). Separate the layers and extract the aqueous layer with dichloromethane (500 mL). Combine the organic layers and wash with brine (1100 mL). Dry with magnesium sulfate, filter, and concentrate in vacuo to give the crude solid material. Wash the solid with hexane (20 mL), diethyl ether (20 mL) and dichloromethane (20 mL). Dry in vacuo to give 30 g (81%) of 2,2-dimethyl-propionic acid 2,3-dibromo-benzo[b]thiophen-6-yl ester.

Dissolve 2,2-dimethyl-propionic acid 2,3-dibromo-benzo[b]thiophen-6-yl ester (32 g, 82 mmol) in ethanol (725 mL), add 50% aqueous solution of potassium hydroxide (39 mL, 328 mmol) and heat to reflux for 4 hours. Concentrate in vacuo to ½ volume, partition between ethyl acetate (500 mL) and saturated aqueous ammonium chloride (500 mL), separate layers, wash organic with saturated aqueous ammonium chloride (2×500 mL), and brine (300 mL). Dry with sodium sulfate, filter, and concentrate in vacuo to give 25.5 g of 2,3-dibromo-benzo[b]thiophen-6-ol (100%).

Add a solution of 2,3-dibromo-benzo[b]thiophen-6-ol (43.9 g, 143 mmol) in DMF (1000 mL), dropwise, to a suspension of sodium hydride in DMF (1.5 L) at 0° C. Stir for 20 minutes, add benzyl bromide (17 mL, 143 mmol). Remove ice bath, and stir at room temperature for 2 hours. Pour reaction mixture into water (8 L) and ethyl acetate (4 L) and stir overnight. Separate layers and wash organic layer with water (3×800 mL) and brine (800 mL). Dry with sodium sulfate, filter, and concentrate in vacuo to give 52.4 g of 6-benzyloxy-2,3-dibromo-benzo[b]thiophene (92%).

Dissolve 6-benzyloxy-2,3-dibromo-benzo[b]thiophene (20 g, 50 mmol) in dichloromethane (88 mL) and add trifluoroacetic acid (88 mL). Stir for 10 minutes, then add 30% aqueous solution of hydrogen peroxide (5.1 mL, 50 mmol) and stir for 4 hours. Add solid sodium bisulfite (2.2 g, 21 mmol), dilute with water (30 mL), stir for 15 minutes, and then concentrate in vacuo. Partition residue between dichloromethane (150 mL) and saturated aqueous sodium bicarbonate (150 mL), separate layers, wash organic layer with additional saturated aqueous sodium bicarbonate (150 mlT) and brine (100 mL). Dry with sodium sulfate, filter, and concentrate in vacuo; Chromatograph on a SiO₂ column eluting with 100% dichloromethane to give 12.8 g of 6-benzyloxy-2,3-dibromo-benzo[b]thiophene 1-oxide (62%).

Dissolve 6-benzyloxy-2,3-dibromo-benzo[b]thiophene 1-oxide (5.9 g, 14.2 mmol) in THF (120 mL). Add a suspension of 4-(2-piperidin-1-yl-ethoxy)-phenol (3.14 g, 14.2 mmol) and potassium tert-butoxide (1.75 g, 15.6 mmol) in THF (120 mL) and stir at 45° C. for 1 hour. Partition reaction mixture between dichloromethane (400 mL) and saturated aqueous NH₄Cl (400 mL) and separate. Wash the organic layer with saturated aqueous NH₄Cl (400 mL) and brine. Dry with sodium sulfate, filter, and concentrate in vacuo. Chromatograph the residue on a SiO₂ column eluting with methanol in dichloromethane (0 to 5%) to give 6.9 g of 1-{2-[4-(6-benzyloxy-2-bromo-1-oxo-1H-1λ⁴-benzo[b]thiophen-3-yloxy)-phenoxy]-ethyl}-piperidine (88%).

Dissolve 1-{2-[4-(6-benzyloxy-2-bromo-1-oxo-1H-1λ⁴-benzo[b]thiophen-3-yloxy)-phenoxy]-ethyl}-piperidine (22.36 g, 40.3 mmol) in methanol (160 mL) and chloroform (80 mL). Add a 30% solution of titanium trichloride in aqueous HCl (31.4 mL, 80.6 mmol) and stir at ambient temperature for 2 hours. Quench reaction mixture with saturated aqueous sodium bicarbonate (500 mL) and dilute with dichloromethane (500 mL). Separate layers and wash the organic layer with saturated aqueous sodium bicarbonate (500 mL), water (500 mL), and brine (500 mL). Dry with sodium sulfate, filter and concentrate in vacuo. Chromatograph the residue on a SiO₂ column eluting with methanol (containing 10% NH₄OH) in dichloromethane (0 to 2%) to give 19.2 g of the title compound (88%).

EXAMPLE 87

1-(2-{4-[6-Benzyloxy-2-(4-ethanesulfonyl-phenyl)-benzo[b]thiophen-3-yloxy]-phenoxy}-ethyl)-piperidine

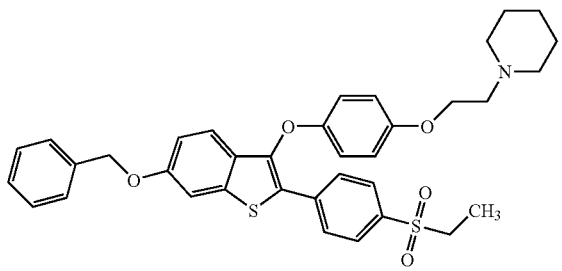

Dissolve 1-{2-[4-(6-benzyloxy-2-bromo-benzo[b]thiophen-3-yloxy)-phenoxy]-ethyl}-piperidine (700 mg, 1.3 mmol) in dioxane (13 mL) and 10% aqueous sodium carbonate (6.9 mL, 6.5 mmol) and add 4-(ethanesulphonyl)benzene boronic acid (430 mg, 2 mmol) and Pd(PPh₃)₄ (150 mg, 0.13 mmol). Heat to 70° C. and stir overnight. Dilute with diethyl ether (25 mL) and water (25 mL), filter through Celite, and separate layers. Extract the aqueous layer with diethyl ether (50 mL). Combine the organic layers and wash with water (50 mL) and brine (50 mL). Dry with sodium sulfate, filter, and concentrate in vacuo. Chromatograph residue on a SiO₂ column eluting with methanol in dichloromethane (0 to 5%) to give 400 mg of the title compound (49%): mass spectrum (ion spray): m/z=628.3 (M+H).

EXAMPLE 88

2-(4-Ethanesulfonyl-phenyl)-3-[4-(2-piperidin-1-yl-ethoxy)-phenoxy]-benzo[b]thiophen-6-ol Dissolve the compound of Example 87 (400 mg, 0.64 mmol) in methanol (7 mL) and ethyl acetate (7 mL). Add ammonium formate (521 mg, 8.3 mmol) and palladium hydroxide (240 mg) and heat to reflux for 5 hours. Filter the reaction mixture and concentrate in vacuo to give 300 mg of the title compound (86%): mass spectrum (ion spray): m/z=538 (M+H).

EXAMPLE 89

2-(4-Ethanesulfonyl-phenyl)-3-[4-(2-piperidin-1-yl-ethoxy)-phenoxy]-benzo[b]thiophen-6-ol Hydrochloride Dissolve the compound of Example 88 (300 mg, 0.56 mmol) in dichloromethane (10 mL) and methanol (0.5 mL).

Add 2M HCl in diethyl ether (0.4 mL) and stir for 10 minutes. Concentrate in vacuo and dry the solids in a vacuum oven at 50° C. overnight to give 224 mg of the title compound (71%): mass spectrum (ion spray): m/z=538 (M+H).

EXAMPLE 90

1-(2-{4-[6-Benzyloxy-2-(4-methanesulfonyl-phenyl)-benzo[b]thiophen-3-yloxy]-phenoxy}-ethyl)-piperidine Trifluoroacetate

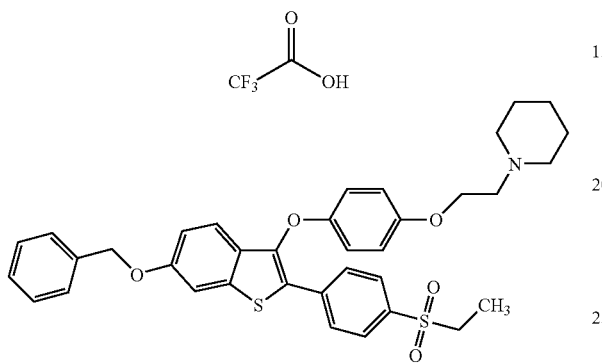

Sonicate a suspension of palladium (I) acetate (103 mg, 0.46 mmol) and tricyclohexylphosphine (193 mg, 0.69 mmol) in acetonitrile (3 mL) for 10 minutes. In a separate flask, add a solution of 1-{2-[4-(6-benzyloxy-2-bromo-benzo[b]thiophen-3-yloxy)-phenoxy]-ethyl}-piperidine (containing a 2,7-dibrominated impurity; 250 mg, 0.46 mmol) and 4-(methanesulphonyl)benzene boronic acid (276 mg, 1.38 mmol) in acetonitrile (6 mL) to cesium fluoride (629 mg, 4.14 mmol). Add the sonicated catalyst mixture, and heat to 90° C. for 1 hour. Concentrate in vacuo and partition the residue between ethyl acetate (20 mL) and saturated aqueous sodium bicarbonate (20 mL). Wash the organic layer with saturated aqueous ammonium chloride (30 mL) and brine (20 mL). Dry with sodium sulfate, concentrate in vacuo, and chromatograph the residue on a SiO₂ column eluting with methanol in dichloromethane (0 to 5%) to give 220 rmg of the title compound contaminated with the byproduct arising from cross-coupling at both the 2- and 7-positions. Separate this mixture by preparative HPLC to yield 85 mg of the title compound (30%): mass spectrum (ion spray): m/z=614 (M+H).

EXAMPLE 91

2-(4-Methanesulfonyl-phenyl)-3-[4-(2-piperidin-1-yl-ethoxy)-phenoxy]-benzo[b]thiophen-6-ol Dissolve the compound of Example 90 (85 mg, 0.14 mmol) in methanol (14 mL) and ethyl acetate (14 mL). Add ammonium formate (262 mg, 4.2 mmol) and palladium hydroxide (90 mg) and heat to reflux for 1 hour. Filter the reaction mixture and concentrate in vacuo. Partition the residue between ethyl acetate:methanol (5:1, 6 mL) and saturated aqueous sodium bicarbonate:brine (1:1, 6 mL). Wash the organic layer with brine, and dry with sodium sulfate. Concentrate in vacuo to give 50 mg of the title compound (68%): ¹H NMR (CDCl₃): δ 7.85 (s, 4H), 7.18 (d, J=8.2 Hz, 1H), 7.14-7.12 (m, 1H), 6.78-6.74 (m, 3H), 6.59-6.55 (m, 2H), 4.07 (t, J=5.4 Hz, 2H), 3.05 (s, 3H), 2.92-2.88 (m, 2H), 2.69 (bs, 4H), 1.74-1.68 (m, 4H), 1.50 (bs, 2H).

EXAMPLE 92

2-(4-Methanesulfonyl-phenyl)-3-[4-(2-piperidin-1-yl-ethoxy)-phenoxy]-benzo[b]thiophen-6-ol Hydrochloride Dissolve the compound of Example 91 (50 mg, 0.09 mmol) in ethyl acetate (1 mL), dilute with diethyl ether (5 mL), and immediately place into an ice bath and add 2M HCl in diethyl ether (0.07 mL). Collect the precipitate on filter paper and rinse with diethyl ether. Dry the solid in a vacuum oven overnight at 60° C. to give 19 mg of the title compound (38%): mass spectrum (ion spray): m/z=524 (M+H).

EXAMPLE 93

1 (2-{4-[6-Benzyloxy-2-(3-fluoro-4-methanesulfonyl-phenyl)-benzo[b]thiophen-3-yloxy]-phenoxy}-ethyl)-piperidine

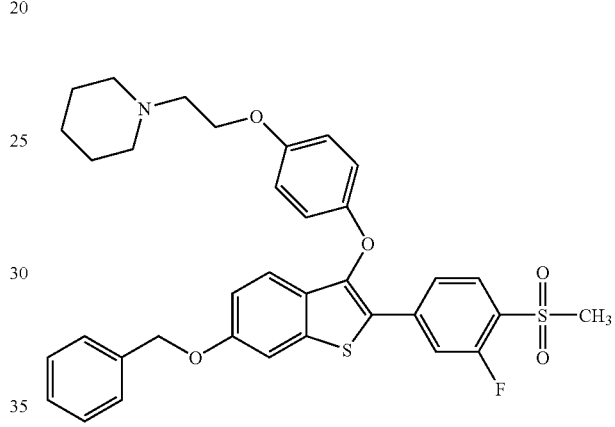

Dissolve 1-{2-[4-(6-benzyloxy-2-bromo-benzo[b]thiophen-3-yloxy)-phenoxy]-ethyl}-piperidine (350 mg, 0.65 mmol) and 3-fluoro-4-methanesulfonyl-phenyl-boronic acid (213 mg, 0.98 mmol) in dioxane (10 mL) and add 10% aqueous sodium carbonate (9 mL) and Pd(PPh₃)₄ (75 mg, 0.065 mmol). Heat to reflux for 3 hours. Partition the reaction mixture between dichloromethane (20 mL) and saturated aqueous ammonium chloride (20 mL). Wash the organic layer with brine (30 mL), dry with sodium sulfate, and concentrate in vacuo. Chromatograph the residue on a SiO₂ column eluting with methanol in dichloromethane (0 to 5%) to give 150 mg of the title compound contaminated with a 2-H reduced byproduct. Take the mixture on to the next step without further purification.

EXAMPLE 94

2-(3-Fluoro-4-methanesulfonyl-phenyl)-3-[4-(2-piperidin-1-yl-etho xy)-phenoxy]-benzo[b]thiophen-6-ol Trifluoroacetate Dissolve the compound of Example 93 (150 mg, 0.24 mmol) in methanol (2 mL) and ethyl acetate (2 mL). Add ammonium formate (300 mg, 4.8 mmol) and palladium hydroxide (150 mg) and heat to reflux overnight. Filter the reaction mixture and concentrate in vacuo. Chromatograph the residue on a SiO₂ column eluting with methanol in dichloromethane (0 to 10%) to give 80 mg of the title compound, contaminated with the debenzylated 2-H reduced byproduct from the previous step. Separate this mixture by preparative HPLC to yield 13 mg of the title compound (8%): mass spectrum (ion spray): m/z=542 (M+H).

EXAMPLE 95

1-(2-{4-[6-Benzyloxy-2-(4-trifluoromethanesulfonyl-phenyl)-benzo[b]thiophen-3-yloxy]-phenoxy}-ethyl)-piperidine

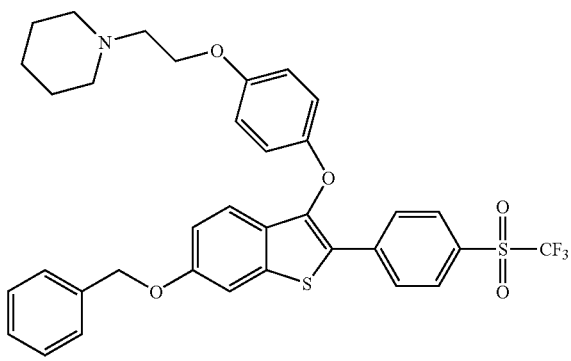

Sonicate a suspension of palladium (II) acetate (146 mg, 0.65 mmol) and tricyclohexylphosphine (273 mg, 0.98 mmol) in acetonitrile (4 mL) for 10 minutes. In a separate flask, add a solution of 1-{2-[4-(6-benzyloxy-2-bromo-benzo[b]thiophen-3-yloxy)-phenoxy]-ethyl}-piperidine (350 mg, 0.65 mmol) and 4,4,5,5-tetramethyl-2-(4-trifluoromethanesulfonyl-phenyl)-[1,3,2]dioxaborolane (531 mg, 2.0 mmol) in acetonitrile (9 mL) to cesium fluoride (889 mg, 5.9 mmol). Add the sonicated catalyst mixture, and heat to 90° C. for 2 hours. Concentrate in vacuo and partition the residue between ethyl acetate (20 mL) and saturated aqueous sodium bicarbonate (20 mL). Combine the organic layer with saturated aqueous ammonium chloride (20 mL) and filter. Wash the organic layer with brine (20 mL), dry with sodium sulfate, and concentrate in vacuo. Chromatograph the residue on a $SiO_2$ column eluting with methanol in dichloromethane (0 to 3%) to give 240 mg of the title compound (55%) contaminated with tricyclohexylphosphine oxide. $^1$H NMR (CDCl$_3$): δ 8.03-7.95 (m, 4H), 7.45-7.33 (m, 5H), 7.32 (d, J=2.3 Hz, 1H), 7.29 (d, J=8.9 Hz, 1H), 6.96 (dd, J=9.0, 2.2 Hz, 1H), 6.89-6.79 (m, 4H), 5.13 (s, 2H), 4.03 (t, J=6.0 Hz, 2H), 2.73 (t, J=6.0 Hz, 2H), 2.48 (bs, 4H), 1.96-1.18 (complex multiplet obscured by P(O)Cy$_3$, 6H).

EXAMPLE 96

3-[4-(2-Piperidin-1-yl-ethoxy-phenoxy]-2-(4-trifluoromethanesulfonyl-phenyl)-benzo[b]thiophen-6-ol Dissolve the compound of Example 95 (contaminated with P(O)Cy$_3$; 240 mg, 0.36 mmol) in methanol (4 mL) and ethyl acetate (4 mL). Add ammonium formate (113 mg, 1.8 mmol) and palladium hydroxide (60 mg) and heat to reflux for 3 hours. Filter and concentrate in vacuo. Chromatograph the residue on a $SiO_2$ column eluting with methanol in dichloromethane (0 to 4%) to give 100 mg of the title compound (47%): $^1$H NMR (CDCl$_3$): δ 7.94 (s, 4H), 7.20 (d, J=8.8 Hz, 1H), 7.14 (d, J=2.2 Hz, 1H), 6.79-6.76 (m, 1H), 6.75 (dd, J=8.8, 2.2 Hz, 1H), 6.63-6.58 (m, 2H), 4.03 (t, J=5.8 Hz, 2H), 2.80 (t, J=5.8 Hz, 2H), 2.57 (bs, 4H), 1.68-1.61 (m, 4H), 1.49-1.44 (m, 2H).

EXAMPLE 97

3-[4-(2-Piperidin-1-yl-ethoxy)-phenoxy]-2-(4-trifluoromethanesulfonyl-phenyl)-benzo[b]thiophen-6-ol Trifluoroacetate Dissolve the compound of Example 96 (100 mg, 0.17 mmol) in ethyl acetate (2 mL), dilute with diethyl ether (10 mL) and place in an ice bath. Immediately add 2M HCl in diethyl ether (0.13 mL) and collect the solids on filter paper. Purify by preparative HPLC to yield 37 mg of the title compound (29%): mass spectrum (ion spray): m/z=578 (M+H).

Preparation 28

6-Methoxy-2-(4-methanesulfonylphenyl)-1-(4-iodophenoxy)naphthalene

Place 6-methoxy-1-tetralone (1 eq.), 4-bromothioanisole (2.5 eq.), palladium acetate (0.01 eq.), 2-dicyclohexylphosphino-2'-(N,N-dimethylamino)biphenyl (0.02 eq.) and toluene in a 3 neck flask equipped with a mechanical stirrer, reflux condenser, nitrogen purge and a temperature probe. Add sodium tert-butoxide (4 eq.) and heat the slurry to reflux. After about 2-4 hours, cool the reaction to room temperature and add 3M aqueous HCl along with tetrahydrofuran. Stir the biphasic reaction mixture for 30 minutes before filtration and separation of the layers. Concentrate the organic layer to isolate 6-methoxy-2-(4-methylthiophenyl)naphthalene-1-ol by filtration.

Place sodium hydride (1.05 eq.) in dry dimethylformamide in a 3 neck flask equipped with a mechanical stirrer, addition funnel with nitrogen purge, and a temperature probe under nitrogen. Charge the addition funnel with 6-methoxy-2-(4-methylthiophenyl)naphthalene-1-ol (1 eq.) dissolved in dry dimethylformamide. Add this solution dropwise to the stirred sodium hydride solution at a rate that holds the temperature below 35° C. Stir the reaction mixture for 30 minutes before adding 4-fluoronitrobenzene with additional dry dimethylformamide. Heat the solution to 60° C. Once the reaction is complete, cool the flask and add water slowly to cause precipitation of the product. Filter the crude product and wash with water and then methyl tert-butyl ether. Dry the filter cake in a vacuum oven to give 6-methoxy-2-(4-methylthiophenyl)-1-(4-nitrophenoxy)naphthalene.

Place meta-chloroperbenzoic acid (2.5 eq.) and methylene chloride in a 3 neck flask equipped with a mechanical stirrer, addition funnel with nitrogen purge, and a temperature probe. Charge the addition funnel with 6-methoxy-2-(4-methylthiophenyl)-1-(4-nitrophenoxy)naphthalene (1 eq.) dissolved in methylene chloride. Add this solution dropwise to the stirred slurry of perbenzoic acid at 10° C. Upon completion of the addition, stir the solution for 30 minutes. Upon reaction completion, add 1N aqueous NaOH slowly holding the temperature at or below 25° C. Separate the layers and concentrate the organic layer. Purify the crude reaction concentrate on silica gel eluting with methylene chloride to afford 6-methoxy-2-(4-methanesulfonylphenyl)-1-(4-nitrophenoxy)naphthalene.

Place 6-methoxy-2-(4-methanesulfonylphenyl)-1-(4-nitrophenoxy)naphthalene in a hydrogenation vessel with 3 volumes of dimethylformamide and 5% Pd/C catalyst. Pressurize the vessel with hydrogen and once the reaction is

63 deemed complete, remove the catalyst by filtering over Hyflo. To the filtrate add 1N aqueous HCl to precipitate the crude product. Filter the precipitate, wash with 1N aqueous HCl and place the filter cake in a vacuum drying oven to give 6-methoxy-2-(4-methanesulfonylphenyl)-1-(4-aminophenoxy) naphthalene hydrochloride.

Place 6-methoxy-2-(4-methanesulfonylphenyl)-1-(4-aminophenoxy)naphthalene hydrochloride (1 eq.), iodine (0.6 eq.), copper iodide (1.05 eq.) and acetonitrile in a 3 neck flask equipped with a mechanical stirrer, addition funnel, nitrogen purge and temperature probe. Charge the addition funnel with isoamylnitrite (1.1 eq.) in acetonitrile and add this mixture dropwise at 20° C. or below. After the addition, stir the mixture for 1 hour. Once the reaction is complete, add saturated sodium thiosulfate and methylene chloride to the mixture and stir for 1 hour. Filter the reaction mixture and separate the layers. Concentrate the organic layer to form a solid. Purify the solid on silica gel to afford the title compound.

Alternative Preparation of the Compound of Example 1

Place 6-methoxy-2-(4-methanesulfonylphenyl)-1-(4-iodophenoxy)naphthalene (1 eq.), cesium carbonate (2 eq.), 1,10-phenanthroline (0.2 eq.), of copper iodide (0.1 eq.) and 1-piperidineethanol (5 volumes) in a 3 neck flask equipped with a mechanical stirrer, a reflux distillation head, and a temperature probe. Evacuate the system and back fill with nitrogen 3 times, then heat to 170° C. After the reaction is complete, cool the flask to 80° C. and place the system under vacuum to remove piperidineethanol by distillation. Release the vacuum and cool the flask to 50° C. at which time add 05N aqueous NaOH. Cool the flask to less than 35° C. and add methylene chloride. Separate the layers and add methyl tert-butyl ether to the organic layer. Concentrate the organic layer to form a precipitate. Filter the precipitate, wash it with methyl tert-butyl ether then dry it in a vacuum oven. Dissolve the precipitate in methylene choride and purify on silica gel to afford the title compound.

Preparation 29

5-Bromo-2-methanesulfonyl-1,3-dimethyl-benzene

Add 5-bromo-2-fluoro-1,3-dimethyl-benzene (3.5 g, 17.2 mmol) to dimethylformamide (DMF, 30 mL) at ambient temperature followed by sodium thiomethoxide (1.32 g, 17.9 mmol). Heat at 50° C. for 8 hours and dilute with water (10 mL) and diethyl ether (100 mL). Separate the layers, wash the organics with brine, and dry with magnesium sulfate before concentrating to a residue. Chromatograph the residue on a $SiO_2$ column eluting with diethyl ether (20%) in hexane to give 566 mg (14%) of 5-bromo-1,3-dimethyl-2-methylsulfanyl-benzene.

Dissolve 5-bromo-1,3-dimethyl-2-methylsulfanyl-benzene (555 mg, 2.42 mmol) in methanol (30 mL) and treat with oxone (6.0 g, 9.8 mmol). Stir the mixture at ambient temperature for 1 hour. Filter the suspension through silica gel and elute with $CH_2Cl_2$ (100 mL). Evaporate the filtrate to give 316 mg (50%) of the title compound.

64

EXAMPLE 98

1-(2-{4-[2-(3,5-Dimethyl-4-methylsulfonyl-phenyl)-6-methoxy-naphthalen-1-yloxy]-phenoxy}-ethyl)-piperidine

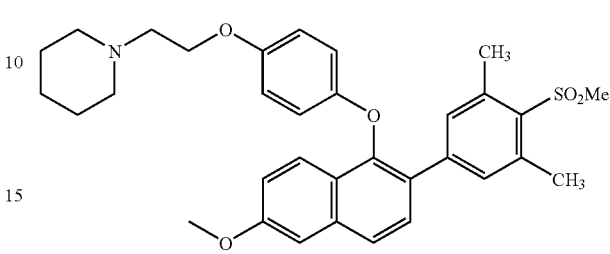

Combine palladium (II) acetate (13 mg, 0.06 mmol), tricyclohexylphosphine (27 mg, 0.10 mmol), cesium fluoride (518 mg, 3.4 mmol) and acetonitrile (10 mL). Stir for 5 minutes. Add the compound of Preparation 1 (200 mg, 0.38 mmol) and bis(neopentylglycolato)diboron (129 mg, 0.57 mmol). Heat to 90° C. for 1 minute and add 5-bromo-2-methanesulfonyl-1,3-dimethyl-benzene (110 mg, 0.42 mmol) in acetonitrile (4 mL). Stir at 90° C. for 10 minutes. Cool to room temperature and dilute the solution with ethyl acetate (20 mL) and wash with saturated aqueous $NaHCO_3$ (10 mL). Separate the layers, wash the organic layer with brine, dry with $MgSO_4$, filter, and concentrate in vacuo. Chromatograph the residue on a $SiO_2$ column eluting with methanol (4%) in dichloromethane to give 180 mg (76%) of the title compound. Mass spectrum (ion spray): m/z=560.3 (M+H).

EXAMPLE 99

6-(3,5-Dimethyl-4-methylsulfonyl-phenyl)-5-[4-(2-piperidin-1-yl-ethoxy)-phenoxy]-naphthalen-2-ol Hydrochloride Dissolve the compound of Example 98 (180 mg, 0.32 mmol) in dichloromethane (5 mL) and add 2.0 M hydrochloric acid in diethyl ether solution (0.4 mL, 0.8 mmol). Stir this solution at ambient temperature for 2 minutes then evaporate in vacuo. After drying under vacuum, add dichloromethane (5 mL) and place this solution in an ice bath with stirring. Add boron tribromide (0.1 mL, 1.1 mmol) and stir the reaction for 1 hour at ambient temperature. Add saturated aqueous sodium bicarbonate (1 mL) and dilute with $CH_2Cl_2$ (20 mL). Separate the layers and wash the organic layer with saturated aqueous sodium bicarbonate and brine; then dry (magnesium sulfate) and evaporate in vacuo. Chromatograph the residue on a $SiO_2$ column eluting with methanol (4%) in dichloromethane to give the free base (40 mg) of the title compound: mass spectrum (ion spray): m/z=560.3 (M+H). Dissolve the free base in EtOAc (2 mL) and $Et_2O$ (2 mL), and add 2M HCl in $Et_2O$ (0.40 mL, 0.80 mmol). Stir at room temperature for 10 minutes. Remove the solvent in vacuo and dry the solid under vacuum to yield 30 mg (18%) of the title compound. Mass spectrum (ion spray) m/z=546.4 (M+H—HCl).

Preparation 30

4-Bromo-1-methanesulfonyl-2-methylsulfanyl-benzene

Dissolve 4-bromo-2-fluoro-1-methanesulfonyl-benzene (340 mg, 1.34 mmol) into DMF (8 mL) and treat with sodium thiomethoxide (103 mg, 9.8 mmol). Stir at room temperature for 2 days. Add water (10 mL) and CH$_2$Cl$_2$ (20 mL). Separate the layers and wash the organic layer with aqueous lithium chloride (10%), then dry (magnesium sulfate) and evaporate in vacuo. Chromatograph the residue on a SiO$_2$ column eluting with EtOAc (20%) in hexane to give 286 mg (76%) of the title compound.

EXAMPLE 100

1-(2-{4-[2-(4-Methanesulfonyl-3-methylsulfanyl-phenyl)-6-methoxy-naphthalen-1-yloxy]-phenoxy}-ethyl)-piperidine

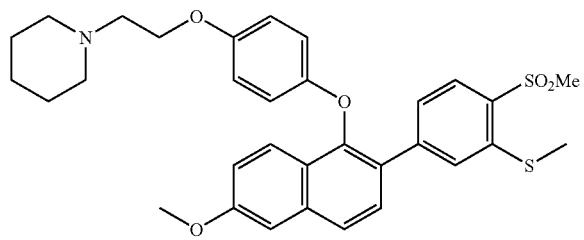

Combine palladium (II) acetate (13 mg, 0.06 mmol), tricyclohexylphosphine (27 mg, 0.10 mmol), cesium fluoride (518 mg, 3.4 mmol) and acetonitrile (10 mL). Stir for 5 minutes. Add the compound of Preparation 1 (200 mg, 0.38 mmol) and bis(neopentylglycolato)diboron (129 mg, 0.57 mmol). Heat to 90° C. for 1 minute and add 4-bromo-1-methanesulfonyl-2-methylsulfanyl-benzene (118 mg, 0.42 mmol) in acetonitrile (4 mL). Stir at 90° C. for 10 minutes. Cool to room temperature and dilute the solution with EtOAc (20 mL) and wash with saturated aqueous NaHCO$_3$ (10 mL). Separate the layers, wash the organic layer with brine (10 mL), dry with MgSO$_4$, filter, and concentrate in vacuo. Chromatograph the residue on a SiO$_2$ column eluting with methanol (4%) in dichloromethane to give 150 mg (64%) of the title compound. Mass spectrum (ion spray): m/z=578.3 (M+H).

EXAMPLE 101

6-(4-Methanesulfonyl-3-methylsulfanyl-phenyl)-5-[4-(2-piperidin-1-yl-ethoxy)-phenoxy]-naphthalen-2-ol Hydrochloride Dissolve the compound of Example 100 (150 mg, 0.26 mmol) in dichloromethane (3 mL) and add 2.0 M hydrochloric acid in diethyl ether (0.2 mL, 0.4 mmol). Stir this solution at ambient temperature for 2 minutes then evaporate in vacuo. After drying in vacuo, add dichloromethane (5 mL) and place this solution in an ice bath with stirring. Add boron tribromide (0.1 mL, 1.1 mmol) and stir the reaction for 1 hour at ambient temperature. Add saturated aqueous sodium bicarbonate (I mL) and dilute with CH$_2$Cl$_2$ (20 mL). Separate the layers and wash the organic layer with saturated aqueous sodium bicarbonate and brine; then dry (magnesium sulfate) and evaporate in vacuo. Chromatograph the residue on a SiO$_2$ column eluting with methanol (4%) in dichloromethane to give 40 mg of the free base of the title compound. Mass spectrum (ion spray): m/z=564.2 (M+H). Dissolve the free base in EtOAc (2 mL) and Et$_2$O (2 mL), and add 2M HCl in Et$_2$O (0.40 mL, 0.80 mmol). Stir at room temperature for 10 minutes. Remove the solvent in vacuo and dry the solid in a vacuum to yield 30 mg (19%) of the title compound. Mass spectrum (ion spray) m/z=564.3 (M+H—HCl).

Preparation 31

2-(4-Cyclopropanesulfonyl-phenyl)-4,4,5,5-tetramethyl-[1,3,2]dioxaborolane

Dissolve 4-bromo-benzenethiol (2.00 g, 10.6 mmol) in dry DMSO (50 mL) under a nitrogen atmosphere. Add potassium tert-butoxide (1.30 g, 11.7 mmol) and stir until dissolved. Add cyclopropyl bromide (2.6 mL, 31.8 mmol) and heat the reaction to 80° C. for 2 days. Cool to room temperature and pour the reaction into water (500 mL). Extract the aqueous layer with Et$_2$O (2×200 mL) and wash the combined organic layers with water (100 mL). Dry over sodium sulfate and concentrate in vacuo. Chromatograph the residue on a SiO$_2$ column eluting the material with hexanes to give 1.73 g of 1-bromo-4-cyclopropylsulfanyl-benzene (72%).

Dissolve 1-bromo-4-cyclopropylsulfanyl-benzene (1.73 g, 7.55 mmol) in dry methylene chloride (75 mL). Slowly add mCPBA (4.8 g, 18.8 mmol, 68%) in portions to control a mild exotherm. After stirring for 1 hour, filter the resultant precipitate. Wash the filtrate with 1N NaOH (50 mL) and dry the organic layer with sodium sulfate. Concentrate in vacuo to yield 2.0 g of 1-bromo-4-cyclopropanesulfonyl-benzene (100%).

Dissolve 1-bromo-4-cyclopropanresulfonyl-benzene (500 mg, 1.91 mmol), bis(pinacolato)diboron (577 mg, 2.29 mmol), potassium acetate (513 mg, 5.70 mmol) and PdCl$_2$(dppf)CH$_2$Cl$_2$ (46 mg, 0.057 mmol) in dry DMSO (10 mL) under a nitrogen atmosphere. Heat the mixture to 80° C. for four hours. Cool the reaction to room temperature and pour into water (100 mL). Extract the aqueous phase with Et$_2$O (2×50 mL) and wash the combined organic layers with water (50 mL). Dry over sodium sulfate and concentrate in vacuo. Chromatograph the residue on a SiO$_2$ column eluting the material with EtOAc in hexanes (10 to 40%) to give 200 mg of the title compound (34%).

EXAMPLE 102

1-(4-(2-(Piperidin-1-yl)ethoxy)phenoxy)-2-(4-cyclopropanesulfonylphenyl)-6-methoxy-naphthalene

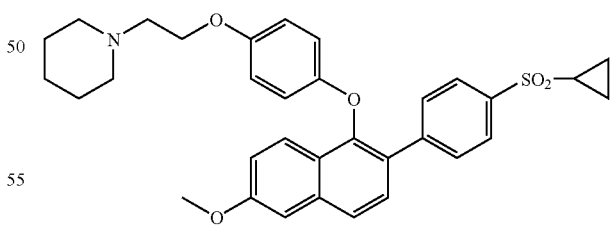

Combine 2-(4-cyclopropanesulfonyl-phenyl)-4,4,5,5-tetramethyl-[1,3,2]dioxaborolane (200 mg, 0.65 mmol), the compound of Preparation 1 (150 mg, 0.28 mmol) and cesium fluoride (214 mg, 1.4 mmol) in dried flask fitted with a reflux condenser. In a separate flask combine palladium (II) acetate (6.2 mg, 0.028 mmol) and tricyclohexylphosphine (11.7 mg, 0.042 mmol). Add acetonitrile (3.0 mL) and sonicate for 10 minutes under nitrogen. Add the catalyst solution to the solids and heat in an 80° C. oil bath for 20 minutes. Cool the suspension to room temperature and filter through packed celite. Rinse the celite with acetonitrile and evaporate. Chromatograph the residue on a SiO₂ column eluting the material with methanol in dichloromethane (0 to 5%) to give 120 mg of the title compound (77%). Mass spectrum (ion spray): m/z 558.3 (M+H).

EXAMPLE 103

6-(4-Cyclopropanesulfonyl-phenyl)-5-[4-(2-piperidin-1-yl-ethoxy)-phenoxy]-naphthalen-2-ol Hydrochloride Dissolve 1-(4-(2-(piperidin-1-yl)ethoxy)phenoxy)-2-(4-cyclopropanesulfonylphenyl)-6-methoxy-naphthalene (120 mg, 0.21 mmol) in methylene chloride (2 mL) and add 2M HCl in Et₂O (210 μL, 0.42 mmol) and concentrate. Dissolve the resultant foam in dry methylene chloride (3 mL) and cool to 0° C. under nitrogen. Add BBr₃ (99 μL, 1.05 mmol) dropwise and stir for 20 minutes. Pour the reaction into saturated sodium bicarbonate (10 mL) and extract with methylene chloride (2×10 mL). Dry the combined organic layers with sodium sulfate and concentrate to a yellow solid. Chromatograph the residue on a SiO₂ column eluting the material with methanol in dichloromethane (2 to 10%) to give 99 mg of the free base of the title compound (87%). Dissolve the free base in methylene chloride and add 2M HCl in Et₂O (200 μL, 0.40 mmol). Evaporate the solvent and dry at 45° C. (<2 mm of Hg) for 18 hours to give 84 mg of the title compound (69%): Mass spectrum (ion spray): m/z=544.3 (M+H—HCl).

Preparation 32

4-Bromo-3-(4-methanesulfonyl-phenyl)-7-methoxy-1,2-dihydro-naphthalene

Add 6-methoxytetralone (1.0 eq.), 4-bromophenyl-methyl-sulfone (1.02 eq.), Pd(OAc)₂ (0.025 eq.), DPEphos ligand [(Oxydi-2,1-phenylene)bis(diphenylphosphine)] (0.026 eq.) and toluene (12 vols) to a three-neck flask equipped with a reflux condenser and nitrogen vent purge. Then add sodium t-butoxide (2.5 eq.) in one portion. The reaction mixture exotherms to approximately 40° C. and forms a heterogeneous yellow mixture. Heat the heterogeneous yellow reaction mixture to 75-80° C. for 1-2 hours. Cool the yellow slurry to room temperature and slowly quench the reaction with water (12 vols), keeping the temperature below 40° C. Cool the aqueous slurry to room temperature and stir for 2 to 3 hours. Filter the slurry over polypropylene and wash the solids with water (3×2 vols). Dry the resulting filter cake in a vacuum overnight at 50° C. to provide crude 2-(4-methanesulfonyl-phenyl)-6-methoxy-3,4-dihydro-2H-naphthalen-1-one (91%).

Add 2-(4-methanesulfonyl-phenyl)-6-methoxy-3,4-dihydro-2H-naphthalen-1-one (1.0 eq.), hyflo (20 wt %), and toluene (7.5 vols) to a three neck flask with a reflux condenser and nitrogen vent purge. While stirring at room temperature, add PBr₃ (1.75 eq.) in one portion. Heat the reaction to reflux (~110° C.) overnight allowing it to vent through a caustic scrubber. After refluxing for 15 hours, cool the yellow solution to 45° C. and slowly add THF (20 vols). Stir this mixture for 30 minutes at 45° and filter it, while warm, over a pad of Hyflo. Wash the pad with 45° C. THF (2×2 vols). Concentrate the filtrate at reduced pressure to remove all of the THF. Carefully add water (7.5 vols) to the remaining mixture keeping the temperature below 40° C. Cool the slurry to room temperature and stir it for 2 to 3 hours. Filter the slurry over a polypropylene pad and wash it with water (2×2 vols). Dry the resulting filter cake in a vacuum oven overnight at 50° C. to provide the title compound (74%).

EXAMPLE 104

1-(2-{4-[2-(4-Methanesulfonyl-phenyl)-6-methoxy-3,4-dihydro-naphthalen-1-yloxy]-phenoxy}-ethyl)-piperidine

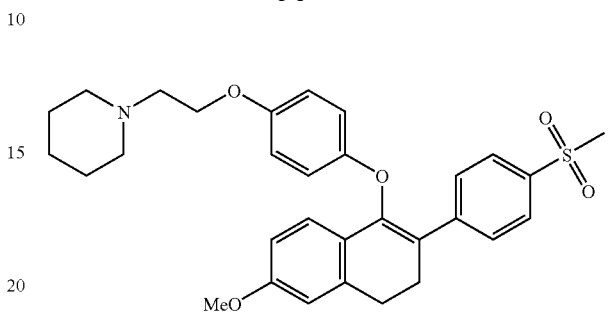

Place the compound of preparation 32 (1.0 eq.), 4-(2-piperidinylethoxy)phenol (1.5 eq.), Cs₂CO₃ (2.5 eq.) and CuCl (0.2 eq.) into a RB flask equipped with magnetic stirrer and condenser. Add toluene (7.5 vols) and de-gas the reaction mixture by vacuum and nitrogen alternation four times. Heat the reaction to reflux for 4-5 hours. Then cool the reaction to ambient temperature and pour it into a mixture of concentrated ammonia solution (1.0 vols), 1N NaOH (5.0 vols), and ethyl acetate (7.5 vols). Vigorously shake the mixture and after the layers separate, discard the aqueous layer and wash the organic layer again with a mixture of ammonia (1.0 vols) and 1N NaOH (5.0 vols), brine (5.0 vols). Dry the organic layer over MgSO₄, and then concentrate it. Dissolve the resulting solid in acetone (2.0 vols) and add hexanes (3.0 vols) as the anti-solvent. After allowing this mixture to stand for 1~2 hours, collect the precipitated material by filtration and allow it to dry, to provide the title compound (80%). MS (ES+) m/e 534 (M+H)⁺;

EXAMPLE 105

6-(4-Methanesulfonyl-phenyl)-5-[4-(2-piperidin-1-yl-ethoxy)-phenoxy]-7,8-dihydro-naphthalen-2-ol In a round bottom flask place the compound of Example 104 (50 mg, 0.094 mmol), sodium ethanethiolate (88 mg, 1.05 mmol) and dimethylformamide (4 mL) in a round bottom flask, at room temperature. Place the reaction in a 95° C. oil bath and stir it for 4 hours, then cool it to ambient temperature. Quench the room temperature mixture with brine and extract it into ethyl acetate. Wash the combined extracts with brine; then dry (sodium sulfate) and concentrate them in vacuo. Purify the crude material on a Chromatotron (silica gel; 5%-12% MeOH gradient in CH₂Cl₂) to give 7 mg of the title Compound (14%). MS (IS+) m/e 520 (M+1).

Preparation 33

1-Bromo-2-(4-methanesulfonylphenyl)-6-methoxynaphthalene

To a 3-neck flask equipped with a reflux condenser and nitrogen vent purge, add 6-methoxytetralone (1.0 eq.), 4-bromophenyl-methyl-sulfone (1.02~1.05 eq.), Pd(OAc)₂ (0.025 eq.), DPEphos ligand (0.026 eq.) and toluene 10-12 volumes.

Add sodium t-butoxide (2.5 eq.) in one portion and allow mixture to exotherm to −40° C. Heat to 75° to 80° C. Upon the reaction completion, as judged by HPLC analysis, cool to room temperature. Add 12 volumes water slowly keeping the temperature <40° C. Stir 2 to 3 hours. Filter over polypropylene pad and wash with water (3×2 volumes). Dry the filter cake overnight at 50° C. to give 2-(4-methanesulfonylphenyl)-6-methoxytetralone.

Combine 2-(4-methanesulfonylphenyl)-6-methoxytetralone (1.0 eq.), hyflo (20%/weight), and toluene (7.5 volumes). Add $PBr_3$ (1.5~1.75 eq.) in one portion while stirring at room temperature. Heat contents to reflux (~110° C.) overnight. Upon reaction completion, as judged by HPLC analysis (usually 15 hours), cool solution to 45° C. and slowly add 20 volumes THF. Stir for 30 minutes at 45° and filter warm over a pad of hyflo. The pad is washed with 2×2 volumes THF at 45° C. Concentrate filtrate to approximately 7 volumes. Add 7.5 volumes water to the remaining mixture keeping the temperature below 40° C. (NOTE: initial addition of water is very exothermic with large evolution of HBr). Cool slurry to room temperature and stir for 2 to 3 hours. Filter over a polypropylene pad and wash with 2×2 volumes water. Dry filter cake overnight at 60° C. under vacuum to give 1-bromo-2-(4-methanesulfonylphenyl)-3,4-dihydro-6-methoxynaphthalene.

Combine 1-bromo-2-(4-methanesulfonylphenyl)-3,4-dihydro-6-methoxynaphthalene and 2,3-dichloro-5,6-dicyano-1,4-benzoquinone (DDQ, 1.8 equiv.) in 10 volumes acetonitrile and 5 volumes of THF. Under nitrogen atmosphere, heat reaction contents to 73-75° C. Monitor reaction progress by GC analysis until reaction, completion. Additional DDQ (0.2-0.3 equiv.) may be required for reaction completion. Cool contents to ambient temperature and add 10 volumes 1 N sodium hydroxide. Stir for approximately 1 hour and filter. Rinse filter cake with 2 volumes water, 3×5 volumes 50% acetonitrile/water and finally 3 volumes methanol. Vacuum dry the filter cake at 65° C. to give the title compound.

Alternative Preparation of the Compound of Example 2

Charge 1-bromo-2-(4-methanesulfonylphenyl)-6-methoxynaphthalene, 4-(2-piperidinylethoxy)phenol (2.0 equiv), cesium carbonate (2.0-2.1 equiv.) and copper chloride (0.15 equiv.) to 12 volumes of diglyme. Evacuate flask for 2 minutes, then purge with nitrogen. Repeat evacuation/nitrogen purge 3 times. Heat the contents to 130° C. until reaction completion as judged by HPLC analysis. Upon reaction completion, cool contents to near ambient temperature and add 12 volumes of ammonium hydroxide and stir for approximately 30 minutes. Filter to remove solids and wash solids with 9 volumes of 30% MeOH/$NH_4OH$, slurrying the solids on the filter support. Wash solids with 2×9 volumes of 30% $NH_4OH$/MeOH, slurrying solids on filter support. Wash with 4 volumes methanol. Vacuum dry filter cake at 60° C. to give the free base of the title compound. Slurry the free base in 9 volumes of toluene and heat the slurry to 70-75° C. Dissolve 1.1 equivalents of hydrogen chloride gas in 2 volumes of ethanol. Add the ethanolic HCl solution to the hot toluene slurry. Cool solution to ambient temperature and stir 1-2 hours. Filter and wash with a small amount of toluene. Vacuum dry the filter cake at 65° C. to give the title compound.

Alternative Preparation of the Compound of Example 4

Combine 1-(2-{4-[2-(4-methanesulfonyl-phenyl)-6-methoxy-naphthalen-1-yloxyl]-phenoxy}-ethyl)-piperidine hydrochloride with 5 volumes 1,2-dichloroethane (DCE) and cool the mixture to <10° C. Add by subsurface addition 5 equivalents of boron trichloride. Stir at ambient temperature until reaction is complete, as judged by HPLC analysis. Quench reaction contents into 5.6 volumes 3A-ethanol (ethanol denatured with about 5% methanol) keeping the contents <50° C. Cool to ambient temperature and stir for 1-3 hours. Filter the solids and rinse the filter cake with 3A-ethanol. Vacuum dry the filter cake at 65° C. to give the title compound. This material may optionally be further purified by dissolving the isolated product in 9.8 volumes of 3A ethanol and 1.5 volumes of deionized water at about the reflux temperature of the mixture. Allow the solution to reflux for approx 30 minutes then allow the mixture to cool to ambient temperature. Once at ambient temperature, allow the resultant slurry to stir for 1-2 hours at ambient temperature, then filter and rinse the filter cake with 3A ethanol. This material may optionally be further purified by dissolving the filter cake in 19 volumes of acetonitrile and 1.4 volumes of deionized water at reflux. Azeotropically remove the water by distillation until a total of 12.1 volumes of distillate are removed. Cool the resulting slurry to ambient temperature, filter and rinse the filter cake with acetonitrile.

Formulation (Pharmaceutical Composition)

Because the compound of formula I contains a basic moiety (i.e., amino), said compound may be formulated as a pharmaceutical acid addition salt, e.g., as the hydrochloride salt or as a salt described in, "Handbook of Pharmaceutical Salts: Properties, Selection and Use", Weinheim, New York: VHCA; Wiley-VCH, 2002. The compound of formula I, or a pharmaceutical acid addition salt thereof, is preferably formulated in a dosage unit form, i.e., in an individual delivery vehicle, for example, a tablet or capsule, prior to administration to the recipient patient. The term "patient" includes female humans and non-human female animals such as companion animals (dogs, cats, horses and the like). The preferred patient of treatment is a female human. Another preferred patient of treatment is a pre-menopausal female human.

The present pharmaceutical compositions are prepared by known procedures using well-known and readily available ingredients. In making the formulations of the present invention, the active ingredient (a formula I compound, or a pharmaceutical salt thereof) will usually be mixed with a carrier, or diluted by a carrier, or enclosed within a carrier which may be in the form of a capsule, sachet, paper or other container. When the carrier serves as a diluent, it may be a solid, semi-solid or liquid material that acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, e.g., polysorbate 80 or lauryl sulfate, emulsifying and suspending agents, preserving agents, sweetening agents or flavoring agents. The compositions of the invention may be formulated so as to provide quick, sustained or delayed release of the active ingredient after administration to the recipient patient.

FORMULATION EXAMPLES 10 mg Capsules or Tablets

Add about 156 mg of a bulking agent (lactose, mannitol, or dextrose), about 20 mg of a disintegrant (microcrystalline cellulose, or starch), about 4 mg of a super disintegrant (crospovidone, or sodium starch glycollate) about 4 mg of a binder (hydroxy propyl methyl cellulose or hydroxy propyl cellulose) and about 10 mg of the active ingredient (e.g., the compound of Example 4) to a granulator and mix to uniformly distribute the powders. Spray an aqueous granulation solution consisting of povidone, hydroxy propyl methyl cellulose, or hydroxy propyl cellulose (sufficient to deliver about 2-4% by weight of dry powders) and wetting agent such as polysorbate 80 or sodium lauryl sulfate (sufficient to deliver between 0.5 and 3% by weight) at a uniform rate onto the powders while mixing. Wet sieve the granulated material through a screen to disrupt large agglomerates. Dry the filtered granulated powder by either fluid bed processing or in a convection oven. Reduce the dried granulated powder to a uniform size by passing through a co-mill or other suitable, apparatus and then transfer the material to a mixer. Uniformly blend the granulated powder with a lubricant (magnesium stearate, or sodium stearyl fumurate at about 1% by weight of the total formulation) and additional disintegrant (about 2-4% by weight in the outside powders). Fill the finished powders into hard gelatin capsules or compress said powder into tablets (followed by film coating the tablets as described below). The total weight of a capsule or tablet prepared in this manner is about 200 mg.

45 mg Capsules or Tablets

Add about 162 mg of a bulking agent (lactose, mannitol or starch), about 10 mg of a disintegrant (crospovidone or sodium starch glycollate), and about 45 mg of the active ingredient (e.g., the compound of Example 4) to a granulator and mix to uniformly distribute the powders. Spray an aqueous granulation solution consisting of povidone (about 35% by weight) and polysorbate 80 (about 10% by weight) at a uniform rate onto the powders while mixing. Wet sieve the granulated material through a screen to disrupt large agglomerates. Dry the filtered granulated powder by either fluid bed processing or in a convection oven. Pass the dried granulated powder through a co-mill or other suitable apparatus and then transfer the material to a mixer. Uniformly blend the granulated powder with a lubricant (magnesium stearate; about 1% by weight of the total formulation) and additional disintegrant (about 2% in the outside powders). Fill the finished powders into hard gelatin capsules or compress said powder into tablets (followed by film coating the tablets as described below). The total weight of a capsule or tablet prepared in this manner is about 230 mg.

Alternatively, to prepare a tablet, add the bulking agent, disintegrant, and the active ingredient to a mixer and blend to uniformly distribute the powders. Once the powders are uniformly distributed, add the lubricant and blend again. Transfer the blended material to a tablet compression machine to prepare the tablets which are subsequently film coated with an appropriate film forming agent.

Biological Assays

Estrogen Receptor Binding Assay: Representative compounds of the present invention are screened for binding affinity to both estrogen receptor types (ERα and ERβ). This competition binding assay measures the compound's ability to displace $^3$H-estradiol and generates $IC_{50}$ and $K_i$ values for both receptor types.

This competition binding assay is run in a buffer containing 50 mM Hepes, pH 7.5, 1.5 mM EDTA, 150 mM NaCl, 10% glycerol, 1 mg/mL ovalbumin and 5 mM DTT, using 0.025 µCi per well $^3$H-Estradiol (NEN #NET517 at 118 Ci/mmol, 1 mCi/mL), 10 ng/well ERα or ERβ receptor (PanVera). A compound of the present invention is added at 10 different concentrations. Non-specific binding is determined in the presence of 1 µM of 17-β Estradiol. The binding reaction (140 µl) is incubated for 4 hours at room temperature, then 70 µl of cold DCC buffer is added to each reaction (DCC buffer contains per 50 mL of assay buffer, 750 mg of charcoal (Sigma) and 250 mg of dextran (Pharmacia)). Plates are mixed 8 minutes on an orbital shaker at 4° C. Plates are then centrifuged at 3,000 rpm at 4° C. for 10 minutes. An aliquot of 120 µl of the mix is transferred to another 96-well, white flat bottom plate (Costar) and 175 µl of Wallac Optiphase "Hisafe 3" scintillation fluid is added to each well. Plates are sealed and shaken vigorously on an orbital shaker. After an incubation of 2.5 hours, the plates are read in a Wallac Microbeta counter. The data is used to calculate an IC50 and % Inhibition at 10 µM. The $K_d$ for $^3$H-Estradiol is determined by saturation binding to ERα and ERβ receptors. The $IC_{50}$ values for test-compounds are converted to $K_i$ using Cheng-Prusoff equation and the $K_d$ determined by saturation binding assay.

Ishikawa Cell Proliferation Assay: This assay measures cell proliferation (using an alkaline phosphatase readout) in both an agonist mode in the presence of a compound of the present invention alone, and in an antagonist mode in which the ability of a compound of the present invention to block estradiol stimulation of growth is measured.

Ishikawa human endometrial tumor cells are maintained in MEM (minimum essential medium, with Earle's salts and L-Glutamine, Gibco BRL, Gaithersburg, Md.), supplemented with 10% fetal bovine serum (FBS) (V/V), (Gibco BRL). One day prior to assay, growth media is changed to assay medium, DMEM/F-12 (3:1) (Dulbecco's Modified Eagle Medium: Nutrient Mixture F-12, 3:1 Mixture, phenol red-free, Gibco BRL) supplemented with 5% dextran coated charcoal stripped fetal bovine serum (DCC-FBS) (Hyclone, Logen, Utah), L-Gluaramine (2 mM), MEM sodium pyruvate (1 mM), HEPES (N-[2-hydroxyethyl]piperazine-N'-[2-ethanesulfonic acid] 2 mM) all from Gibco BRL). After an overnight incubation, Ishikawa cells are rinsed with Dulbecco's Phosphate Buffered Saline (1×) (D-PBS) without $Ca^{+2}$ and $Mg^{+2}$ (Gibco BRL), and trypsinized by a 3 minute incubation with 0.25% Trypsin/EDTA, phenol red-free (Gibco BRL). Cells are resuspended in assay medium and adjusted to 250,000 cells/mL. Approximately-25,000 cells in a 100 ul media are added to flat-bottom 96 wells microculture plates (Costar 3596) and incubated at 37° C. in a 5% $CO_2$ humidified incubator for 24 hours. The next day, serial dilutions of compounds are prepared in assay medium (at 6 times the final concentration in the assay). The assay is run in dual mode, agonist and antagonist modes.

For the agonist mode, plates receive 25 µl/well of assay medium followed by 25 µl/well of a diluted compound of the present invention (at 6× the final concentrations). For the antagonist mode, plates receive 25 µl/well of 6 nM $E_2$ (β-Estradiol, Sigma, St. Louis, Mo.) followed by 25 µl/well of a diluted compound of the present invention (at 6× the final concentrations). After an additional 48-hour incubation at 37° C. in a 5% $CO_2$ humidified incubator, media is aspirated from wells and 100 µl fresh assay medium is added to each microculture. Serial dilutions of compounds are prepared and added to the cells as described above. After an additional 72 hour incubation at 37° C. in a 5% $CO_2$' humidified incubator, the assay is quenched by removing media and rinsing plates twice in Dulbecco's Phosphate Buffered Saline (1×) (D-PBS) (Gibco BRL). The plates are dried for 5 minutes and frozen at −70-C for at least 1 hour. The plates' are then removed from the freezer and allowed to thaw at room temperature. To each well, 100 µl of 1 Step™ PNPP (Pierce Chemical Company, Rockford, Ill.) is added. After a 20-minute incubation, plates are read on a spectophotometer at 405 nm.

The data is fitted to a linear interpolation to derive EC50 (for agonist mode) or IC50 (for antagonist mode) values. For the antagonist mode, a % efficacy for each compound is calculated versus E2 (1 nM) alone. For the agonist mode, a % efficacy for each compound is calculated versus the response to tamoxifen.

In the agonist mode, the compounds of Examples 3-6, 8, 10, 12, 14, 16, 18, 21, 23, 25, 27, 29, 32, 34, 36, 39, 43, 46, 49, 53, 56, 58, 59, 61, 63, 65, 67, 70-73, 75, 78, 80, 82, 86, 89, 92, 94, 97, 99, 101, 103 and 105 were tested and were found to be less stimulatory than tamoxifen. For example, the compound of Example 56 had a relative % efficacy of 71.8%. In the antagonist mode, these same compounds inhibited greater than at least 70% of the 1 nM estradiol response. For example, the compound of Example 16 had an IC50 of 35.2 nM and a % efficacy of 106.7%.

MCF-7 Proliferation Assay: The MCF-7 cell line was derived from a human breast adenocarcinoma and is used as an indicator of potential antiproliferative activity in breast epithelium.

MCF-7 breast adenocarcinoma cells (ATCC HTB 22) are maintained in MEM (minimal-essential medium, phenol red-free, Gibco BRL) supplemented with 10% fetal bovine serum (FBS) (V/V), L-glutamine (2 mM), sodium pyruvate (1 mM), HEPES ((N-[2-hydroxyethyl]piperazine-N'-[2-ethanesulfonic acid]10 mM}, non-essential amino acids (0.1 mM) and Penicillin Streptomycin (1×). Seven days prior to assay, MCF-7 cells are switched to assay media which is the same as maintenance medium except supplemented with 10% dextran-coated charcoal-stripped fetal bovine serum (DCC-FBS) assay medium in place of 10% FBS. MCF-7 cells are removed from flasks using 10× Trypsin EDTA (phenol red free, Gibco BRL) and diluted to 1× in (Ca++/Mg++free HBSS (phenol red-free). Cells are adjusted to 80,000 cells/mL in assay medium. Approximately 8,000 cells (100 µl) are added to each wellin 96 well Cytostar T scintillation plates (Amersham) and incubated at 37° C. in a 5% $CO_2$ humidified incubator for 24 hours to allow cell adherence and equilibration after transfer.

Serial dilutions of a compound of the present invention are prepared in assay medium at 4× the final desired concentration). A 50 µl aliquot of test compound dilutions (at 4× the final assay concentration) is transferred to duplicate wells followed by 50 µl assay medium for the agonist mode or 50 µl of 40 µM of E2 for the antagonist mode to a final volume of 200 µl. For each of the agonist plates, a basal level (media) and a maximum stimulated level (with 1 µM E2) is determined. For each of the antagonist plates, a basal level (media) and an E2 (10 pM) alone control is determined. After an additional 48 hours at 37° C. in a 5% $CO_2$ humidified incubator, 20 µl of assay medium containing 0.01 µCi of $^{14}C$-thymidine (52 µCi/mmol, 50 µCi/ul, Amersham) is added to each well. The plates are incubated overnight in the same incubator and then counted on the Wallac Microbeta counter. The data is averaged to calculate an IC50 and % inhibition @ 1 µM for the antagonist mode. For the agonist mode, an EC50 and percent of maximum E2 stimulation and concentration of maximum stimulation is calculated.

3-Day Rat Uterus Antagonist Assay: This model for uterine antagonism utilizes immature (3 week old) female rats that are highly sensitive to estrogenic stimulation of the uterus given that their circulating estrogen levels are prepubertal. The uteri from immature rats are fully responsive to exogenous estrogen, yet are quiescent in the absence of exogenous estrogen. Administration of exogenous estrogen to immature rats produces a reliable elevation of uterine weight, which can be used to study uterine antagonist effects. The rats are treated with both estradiol and 4 different concentrations of a compound of the present invention for 3 days and then uterine wet weights are measured.

Nineteen to twenty-one day old (or 45-50 g) female rats are orally treated with E2 (0.1 mg/kg, a maximal stimulatory estrogenic stimulus for reliably increasing uterine weight) and 10, 1.0, 0.1 and 0.01 mg kg test compound for 3 days, 6 rats per group. Test compounds are dissolved in 20% β-hydroxycyclodextrin and administered via oral gavage in a volume of 0.2 mL daily (15 min. prior to the ethynyl estradiol gavage). A vehicle control, E2 alone and E2+ raloxifene are also done as controls. The animals are fasted overnight following the final dose. On the following morning, the animals are weighed, then euthanized (by carbon dioxide asphyxiation) and the uteri rapidly collected (via a mid-line ventral incision) and weighed.

Uterine weight/body weight ratios (UWR) are calculated for each animal. The percent inhibition of the estrogen-induced response is then calculated by the following formula: percent inhibition =100×($UWR_{estrogen}$−$UWR_{test\ compound}$/$UWR_{estrogen}$−$UWR_{control}$). $ED_{50}$ values are derived from a semi-log regression analysis of the linear aspect of the dose response curve. Both the UWR data and the percent inhibition data were statistically analyzed by one way analysis of variance (ANOVA) with post-hoc testing by Fisher's PLSD when indicated by a $p \leq 0.05$. Statistical analyses are performed using the Statview® 4.0 software package.

The compounds of Examples 4-6, 12, 14, 18, 21, 23, 27, 29, 32, 34, 39, 43, 46, 53, 56, 58, 59, 61, 65, 70, 78, 86, 89, 92, 99, 101 and 103 were tested in the above assay and were found to inhibit the estrogen-induced response when administered at 1.0 mg/kg; For example, the compound of Example 92 had an ED50 of 0.53 mpk and a % antagonism of 62.7%.

4-Day OVX Rat Uterine Agonist Assay: In order to assure that a test compound does not have any partial uterine agonist activity, compounds are administered to mature, ovariectomized rats.

Seventy-five day old rats are ovariectomized and treatment is started 14 days later when circulating estradiol levels have reached minimal levels. After 4 days of treatment with 3 doses of a compound of the present invention, (6 rats per group) body weight, uterine wet weight and uterine eosinophil peroxidase (EPO) activity are measured. Cholesterol levels are also measured to compare relative ability to lower cholesterol with other SERMs. If there is any question of uterine stimulation, histological examination will determine epithelial cell height.

The compounds of Examples 4 and 14 were tested in the above assay and did not cause dose-related statistically significant-increases in EPO activity.

10-Day Rat Hormone (Ovarian Stimulation) Screen: An initial, first screen for ovarian toxicity is conducted using a 10-day rat hormone study to measure estradiol and luteinizing hormone levels after compound administration. This screen is conducted by administering compound by oral gavage for 10 days to mature (9-10 week old) F344 female rats. Trunk blood is collected by rapid decapitation for evaluation of LH and estradiol levels approximately 2 hours after the $10^{th}$ dose. Serum, obtained by centrifugation, is removed and stored frozen below −60° C. until assayed. Serum levels of LH and estradiol are measured using radioimmunoassay (RIA) methods.

Rat LH primary antibody and reference preparations (rat LH:RP-3) were obtained from Dr. A. F. Parlow, Director, Pituitary Hormones and Antisera Center, Harbor-UCLA Medical Center, Torrance, Calif. The LH assay upper limits of detection were 30 ng/mL and the lower limits of detection were 0.1 ng/mL for the 100 μl samples.

E2 Clinical Assays. DiaSorin s.r.l., Saluggia (Vercelli), Italy. The upper limit of detection was 1000 pg/mL and the lower limit of detection was 5 pg/mL.

The compounds of Examples 4-6, 14, 21 and 103 were tested in the above assay and did not significantly elevate circulating estradiol or LH levels.

35-Day Ovary-Intact Rat Bone Assay: While previous SERMs, including raloxifene have shown efficacy in preventing bone loss in OVX rats, the possibility of interference with estrogen-regulated turnover in ovary-intact rats needs to be addressed.

This assay is done in mature rats with concentrations based on the demonstrated efficacy in the 3-day assay. Generally, at least three concentrations are chosen based on multiples of the ED50 generated therein. These multiples are generally 1×, 10× and 30× the ED50. A compound of the present invention is administered to an OVX rat for 35 days and is compared to control, ovariectomized, and/or GnRH-administered rats. Femurs, tibiae, uteri, ovaries and serum are taken for further analyses. DEXA (Dual Energy X-ray Absorptivity), CT (Computed Tomography) and histologic analysis are done on the long bones to assess any changes. CT scans of the distal femur are done to calculate BMD (bone mineral density), cross sectional area and BMC (bone mineral content). Bone strength measurements (load to failure) may also be done to determine consequences of any bone mass or material changes. Uterine and ovarian histology are examined to confirm long term dosing effects of uterine efficacy and potential ovarian stimulation. The serum is analyzed for LH and E2 levels as a possible indicator of ovarian effects.

Utilities

As an antagonist of estrogen in breast and uterine tissue, the compound of formula I, or a pharmaceutical acid addition salt thereof, is useful in treating conditions in which estrogen has been demonstrated to play a causal role therein. As an agonist of estrogen in skeletal and cardiovascular systems, the compound of formula I, or a pharmaceutical acid addition salt thereof, is useful in treating conditions in which estrogen has been demonstrated to play a beneficial role therein.

The terms "treating" and "treat" as used herein, include their generally accepted meanings, i.e., alleviating, ameliorating, managing, preventing, prohibiting, restraining, slowing, stopping, or reversing the progression or severity of a pathological condition, or sequela thereof, described herein. The term "preventing" refers to reducing the likelihood that the recipient of a compound of formula I, or a pharmaceutical acid addition salt thereof, will incur or develop any of the pathological conditions, or sequela thereof, described herein.

The diseases, disorders or conditions for which a compound of formula I. or a pharmaceutical acid addition salt thereof, is useful in treating include, but are not limited to, (1) uterine and/or breast cancer; (2) endometriosis; (3) treatment and management of uterine leiomyoma/leiomyomata and associated symptoms; and (4) osteoporosis. Treatment of uterine leiomyoma/leiomyomata as described herein, may also reduce associated symptoms such as pain, urinary frequency, and uterine bleeding.

Dose

As used herein, the term "effective amount" means an amount of a compound of formula I, or a pharmaceutical acid addition salt thereof, that is capable of treating conditions, or detrimental effects thereof, described herein.

The specific dose administered is determined by the particular circumstances surrounding each situation. These circumstances include, the route of administration, the prior medical history of the recipient, the pathological condition or symptom being treated, the severity of the condition/symptom being treated, and the age and sex of the recipient. The recipient patient's physician should determine the therapeutic dose administered in light of the relevant circumstances.

Generally, an effective minimum daily dose of a compound of the present invention will exceed about 5 mg. Typically, an effective maximum daily dose will not exceed about 350 mg. The exact dose may be determined, in accordance with the standard practice in the medical arts of "dose titrating" the recipient; that is, initially administering a low dose of the compound, and gradually increasing the dose until the desired therapeutic effect is observed.

Route of Administration

A compound of formula I, or a pharmaceutical acid addition salt thereof, may be administered by a variety of routes including the intramuscular, intranasal, intravaginal, intravenous, oral, rectal, subcutaneous, topical and transdermal routes. A preferred route of administration is the oral route.

Combination Therapy

The compound of formula I, or a pharmaceutical acid addition salt thereof, may be used in combination with other drugs that are used in the treatment of the diseases or conditions for which these compounds are useful. Such other drug(s) may be administered, by a route and in an amount commonly used therefore, contemporaneously or sequentially with a salt of the present invention. When a compound of the present invention is used contemporaneously with one or more other drugs, a pharmaceutical unit dosage form containing such other drugs in addition to the present compound is preferred. Accordingly, the pharmaceutical compositions of the present invention include those that contain one or more other active ingredients. One example of another other active ingredient that may be combined with a compound of the present invention, either administered separately or in the same pharmaceutical composition, includes agents employed in hormone replacement therapy (HRT).

We claim:

1. A compound which is:

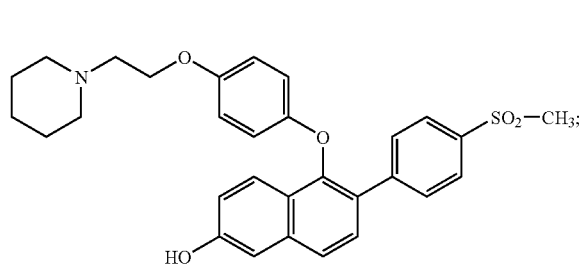

or a pharmaceutical acid addition salt thereof.

2. The copound of claim 1 which is the hydrochloride salt.

* * * * *